(12) United States Patent
Molnar

(10) Patent No.: US 11,051,682 B2
(45) Date of Patent: Jul. 6, 2021

(54) MEDICAL DEVICES WITH CAMERA AND METHODS OF PLACEMENT

(71) Applicant: WM & DG, Inc., Deerfield, IL (US)

(72) Inventor: Robert Molnar, Long Grove, IL (US)

(73) Assignee: WM & DG, INC., Deerfield, IL (US)

( * ) Notice: Subject to any disclaimer, the term of this patent is extended or adjusted under 35 U.S.C. 154(b) by 653 days.

(21) Appl. No.: 15/692,416

(22) Filed: Aug. 31, 2017

(65) Prior Publication Data

US 2019/0059710 A1    Feb. 28, 2019

(51) Int. Cl.
| | |
|---|---|
| A61B 1/05 | (2006.01) |
| A61M 16/04 | (2006.01) |
| A61B 1/267 | (2006.01) |
| A61B 1/06 | (2006.01) |
| A61B 1/00 | (2006.01) |
| A61B 1/01 | (2006.01) |
| A61B 7/02 | (2006.01) |
| A61B 7/00 | (2006.01) |

(52) U.S. Cl.
CPC .............. *A61B 1/05* (2013.01); *A61B 1/0014* (2013.01); *A61B 1/00103* (2013.01); *A61B 1/00105* (2013.01); *A61B 1/00154* (2013.01); *A61B 1/01* (2013.01); *A61B 1/0676* (2013.01); *A61B 1/267* (2013.01); *A61B 1/2676* (2013.01); *A61B 7/003* (2013.01); *A61M 16/04* (2013.01); *A61M 16/0409* (2014.02); *A61M 16/0434* (2013.01); *A61M 16/0465* (2013.01); *A61M 16/0486* (2014.02); *A61M 16/0488* (2013.01); *A61M 16/0495* (2014.02); *A61B 7/023* (2013.01); *A61M 16/0463* (2013.01); *A61M 2205/3375* (2013.01); *A61M 2205/8206* (2013.01);

(Continued)

(58) Field of Classification Search
CPC ........ A61B 1/05; A61B 1/267; A61B 1/00–32; A61M 16/0488; A61M 16/0434; A61M 16/04; A61M 16/0402; A61M 16/0463; A61M 16/0465; A61M 16/0486
See application file for complete search history.

(56) References Cited

U.S. PATENT DOCUMENTS

| | | | |
|---|---|---|---|
| 4,231,365 | A | 11/1980 | Scarberry |
| 4,360,008 | A | 11/1982 | Corazzelli, Jr. |

(Continued)

FOREIGN PATENT DOCUMENTS

| | | |
|---|---|---|
| EP | 0665029 A2 | 8/1995 |
| KR | 20120095385 | 8/2012 |

(Continued)

OTHER PUBLICATIONS

Bledsoe B., "The Disappearing Endotrachael Tube"., Clinical Professor of Emergency Medicine, University of Nevada School of Medicine, 2009, 84 pages.

(Continued)

*Primary Examiner* — Kendra D Carter
*Assistant Examiner* — Thao Tran
(74) *Attorney, Agent, or Firm* — Greer, Burns & Crain, Ltd.

(57) ABSTRACT

The present invention provides medical devices comprising a camera combined with a second device selected from an endotracheal tube, oral airway, supraglottic airway, tracheostomy tube, suction catheter, tubeless intubating device, tool tube and/or stylet. The present invention also provides methods for rapid and accurate placement of a medical device in a patient with a guidance of a bougie and continuous real-time monitoring, including a remote monitoring, of the patient after the placement.

7 Claims, 31 Drawing Sheets

(52) U.S. Cl.
CPC ... *A61M 2209/088* (2013.01); *A61M 2230/04* (2013.01); *A61M 2230/40* (2013.01)

(56) References Cited

U.S. PATENT DOCUMENTS

| | | | |
|---|---|---|---|
| 4,577,638 A | 3/1986 | Graham | |
| 4,584,998 A | 4/1986 | McGrail | |
| 4,607,643 A | 8/1986 | Bell et al. | |
| 4,846,153 A | 7/1989 | Berci | |
| 5,052,386 A | 1/1991 | Fischer, Jr. | |
| 5,025,778 A | 6/1991 | Silverstein et al. | |
| 5,174,283 A * | 12/1992 | Parker | A61M 16/0488 128/200.26 |
| 5,193,692 A | 3/1993 | Farley et al. | |
| 5,241,956 A | 9/1993 | Brain | |
| 5,353,787 A | 10/1994 | Price | |
| 5,372,131 A | 12/1994 | Heinen, Jr. | |
| 5,400,771 A | 3/1995 | Pirak et al. | |
| 5,499,625 A | 3/1996 | Frass et al. | |
| 5,511,916 A | 4/1996 | Farley et al. | |
| 5,513,627 A | 5/1996 | Flam | |
| 5,515,844 A | 5/1996 | Christopher | |
| 5,551,947 A | 9/1996 | Kaali | |
| 5,632,271 A | 5/1997 | Brain | |
| 5,665,052 A | 9/1997 | Bullard | |
| 5,682,880 A | 11/1997 | Brain | |
| 5,733,242 A | 3/1998 | Rayburn et al. | |
| 5,740,791 A | 4/1998 | Ayes | |
| 5,819,733 A | 10/1998 | Bertram | |
| 5,879,306 A | 3/1999 | Fontenot et al. | |
| 5,888,195 A | 3/1999 | Schneider | |
| 6,038,629 A | 3/2000 | Ogilvie et al. | |
| 6,115,523 A | 9/2000 | Choi et al. | |
| 6,142,144 A | 11/2000 | Pacey | |
| 6,189,533 B1 | 2/2001 | Simon et al. | |
| 6,196,225 B1 | 3/2001 | Allgeyer | |
| 6,349,720 B1 | 2/2002 | Clark | |
| 6,386,199 B1 | 5/2002 | Alfery | |
| 6,439,232 B1 | 8/2002 | Brain | |
| 6,440,061 B1 | 8/2002 | Wenner et al. | |
| 6,443,156 B1 | 9/2002 | Niklason et al. | |
| 6,527,704 B1 | 3/2003 | Chang et al. | |
| 6,543,447 B2 | 4/2003 | Pacey | |
| 6,626,169 B2 | 9/2003 | Gaitini | |
| 6,631,720 B1 | 10/2003 | Brain | |
| 6,634,354 B2 | 10/2003 | Christopher | |
| 6,655,377 B2 | 12/2003 | Pacey | |
| 6,860,264 B2 | 3/2005 | Christopher | |
| 6,860,270 B2 | 3/2005 | Sniadach | |
| 6,918,391 B1 | 7/2005 | Moore | |
| 6,929,600 B2 | 8/2005 | Hill | |
| 7,052,456 B2 | 5/2006 | Simon | |
| 7,128,509 B2 | 10/2006 | Farley et al. | |
| 7,156,091 B2 | 1/2007 | Koyama et al. | |
| 7,237,993 B2 | 7/2007 | Farley et al. | |
| 7,331,925 B2 | 2/2008 | McMorrow et al. | |
| 7,421,877 B2 | 9/2008 | Frenken | |
| 7,450,746 B2 | 11/2008 | Yang et al. | |
| 7,520,857 B2 | 4/2009 | Chalana et al. | |
| 7,527,601 B2 | 5/2009 | Dubey et al. | |
| 7,611,466 B2 | 11/2009 | Chalana et al. | |
| 7,654,970 B2 | 2/2010 | Dubey | |
| 7,713,189 B2 | 5/2010 | Hanke | |
| 7,713,216 B2 | 5/2010 | Dubey et al. | |
| 7,727,150 B2 | 6/2010 | Chalana et al. | |
| 7,744,534 B2 | 6/2010 | Chalana et al. | |
| 7,749,165 B2 | 7/2010 | McMorrow et al. | |
| 7,749,176 B2 | 7/2010 | Dubey | |
| 7,811,239 B2 | 10/2010 | Dubey et al. | |
| 7,819,806 B2 | 10/2010 | Yang et al. | |
| 7,854,324 B2 | 12/2010 | Farley et al. | |
| 7,896,007 B2 | 3/2011 | Brain | |
| 7,921,847 B2 | 4/2011 | Totz | |
| 7,942,813 B2 | 5/2011 | Mackin | |
| 7,976,458 B2 | 7/2011 | Stefanchik et al. | |
| 8,016,760 B2 | 9/2011 | Chalana et al. | |
| 8,038,629 B2 | 10/2011 | Solanki et al. | |
| 8,202,215 B2 | 6/2012 | Xiao et al. | |
| 8,215,307 B2 | 7/2012 | Nasir | |
| 8,297,275 B2 | 10/2012 | Ogilvie et al. | |
| 8,308,644 B2 | 11/2012 | McMorrow et al. | |
| 8,371,303 B2 | 2/2013 | Schaner et al. | |
| 8,529,442 B2 | 9/2013 | Pacey et al. | |
| 8,663,099 B2 | 3/2014 | Tydlaska | |
| 8,677,990 B2 | 3/2014 | Gabriel | |
| 8,863,746 B2 | 10/2014 | Totz | |
| 8,928,746 B1 | 1/2015 | Stevrin et al. | |
| 9,211,060 B2 | 12/2015 | Waldron et al. | |
| 9,415,179 B2 | 8/2016 | Molnar | |
| 9,427,142 B2 | 8/2016 | Terliuc | |
| 9,545,249 B2 | 1/2017 | Cole | |
| 9,579,012 B2 | 2/2017 | Vazales et al. | |
| 10,286,231 B2 | 5/2019 | Pederson | |
| 2002/0108610 A1 | 8/2002 | Christopher | |
| 2002/0195103 A1 | 12/2002 | O'Mara | |
| 2003/0220542 A1 | 11/2003 | Belson et al. | |
| 2005/0182297 A1 | 8/2005 | Gravenstein et al. | |
| 2005/0228226 A1 | 10/2005 | Muckner | |
| 2005/0244801 A1 | 11/2005 | DeSalvo | |
| 2005/0268917 A1 | 12/2005 | Boedeker et al. | |
| 2006/0004260 A1 | 1/2006 | Boedeker et al. | |
| 2006/0032505 A1 | 2/2006 | Alfery et al. | |
| 2006/0111633 A1 | 5/2006 | McMorrow et al. | |
| 2006/0149129 A1 | 7/2006 | Watts et al. | |
| 2006/0162730 A1 | 7/2006 | Glassenberg et al. | |
| 2006/0180155 A1 | 8/2006 | Glassenberg et al. | |
| 2006/0276694 A1 | 12/2006 | Acha Gandarias | |
| 2007/0017527 A1 * | 1/2007 | Totz | A61M 16/04 128/207.15 |
| 2007/0095351 A1 | 5/2007 | Globel | |
| 2007/0106121 A1 | 5/2007 | Yokota et al. | |
| 2007/0137651 A1 | 7/2007 | Glassenberg et al. | |
| 2007/0156068 A1 | 7/2007 | Dubey | |
| 2007/0175482 A1 | 8/2007 | Kimmel et al. | |
| 2007/0180887 A1 | 8/2007 | Frenken | |
| 2007/0203393 A1 | 8/2007 | Stefanchik | |
| 2007/0239197 A1 | 10/2007 | Dubey | |
| 2007/0255185 A1 | 11/2007 | Dubey | |
| 2008/0029100 A1 | 2/2008 | Glassenberg et al. | |
| 2008/0114268 A1 | 5/2008 | Dubey | |
| 2008/0115783 A1 | 5/2008 | Brain | |
| 2008/0146879 A1 | 6/2008 | Pacey | |
| 2008/0188774 A1 | 8/2008 | Dubey | |
| 2008/0276932 A1 | 11/2008 | Bassoul | |
| 2009/0090356 A1 | 4/2009 | Cook | |
| 2009/0194102 A1 | 8/2009 | Chen et al. | |
| 2009/0194114 A1 * | 8/2009 | Chen | A61M 16/0409 128/207.15 |
| 2009/0227835 A1 | 9/2009 | Terliuc | |
| 2009/0264708 A1 | 10/2009 | Pacey et al. | |
| 2009/0287050 A1 | 11/2009 | Barthel | |
| 2010/0051024 A1 | 3/2010 | Abrons | |
| 2010/0113916 A1 | 5/2010 | Kumar | |
| 2010/0147309 A1 | 6/2010 | Cuevas et al. | |
| 2010/0180737 A1 | 7/2010 | Klepper | |
| 2010/0204546 A1 | 8/2010 | Hassidov et al. | |
| 2010/0249639 A1 | 9/2010 | Bhatt | |
| 2010/0256451 A1 * | 10/2010 | McGrath | A61B 1/267 600/185 |
| 2010/0261967 A1 | 10/2010 | Pacey et al. | |
| 2010/0312069 A1 | 12/2010 | Sutherland et al. | |
| 2011/0030694 A1 | 2/2011 | Schaner et al. | |
| 2011/0130632 A1 | 6/2011 | McGrail et al. | |
| 2011/0137127 A1 | 6/2011 | Schwartz et al. | |
| 2011/0178372 A1 * | 7/2011 | Pacey | A61B 1/00142 600/188 |
| 2011/0201882 A1 | 8/2011 | Schwartz et al. | |
| 2011/0315147 A1 | 12/2011 | Wood et al. | |
| 2012/0059223 A1 * | 3/2012 | McGrath | A61M 16/0488 600/185 |
| 2012/0259173 A1 | 10/2012 | Waldron et al. | |
| 2012/0260921 A1 | 10/2012 | Sangwan | |
| 2012/0302833 A1 | 11/2012 | Hayman et al. | |
| 2013/0006051 A1 | 1/2013 | Stace et al. | |

(56) References Cited

U.S. PATENT DOCUMENTS

| | | |
|---|---|---|
| 2013/0030249 A1 | 1/2013 | Vazales et al. |
| 2013/0096379 A1 | 4/2013 | Goldberg |
| 2013/0109918 A1 | 5/2013 | Pagan |
| 2013/0158351 A1 | 6/2013 | Daher et al. |
| 2013/0197303 A1 | 8/2013 | Shun |
| 2013/0253368 A1 | 9/2013 | Are et al. |
| 2013/0319406 A1* | 12/2013 | Borrye ............... A61M 16/0488 128/200.26 |
| 2013/0324798 A1* | 12/2013 | Molnar .................. A61B 1/267 600/120 |
| 2014/0018626 A1 | 1/2014 | Lee |
| 2014/0073853 A1 | 3/2014 | Swisher et al. |
| 2014/0076309 A1 | 3/2014 | Takeda et al. |
| 2014/0096766 A1* | 4/2014 | Avitsian .................. A61B 1/267 128/200.26 |
| 2014/0109903 A1* | 4/2014 | Chaudhry ......... A61M 16/0488 128/202.15 |
| 2014/0166020 A1 | 6/2014 | Chang |
| 2014/0194694 A1* | 7/2014 | Chen .................. A61B 1/00052 600/188 |
| 2014/0309494 A1* | 10/2014 | Molnar .............. A61B 1/00128 600/109 |
| 2014/0323806 A1 | 10/2014 | Brain |
| 2014/0357951 A1 | 12/2014 | Muller et al. |
| 2015/0122251 A1 | 5/2015 | Azhir et al. |
| 2016/0038008 A1 | 2/2016 | Molnar |
| 2016/0038014 A1* | 2/2016 | Molnar .............. A61M 16/0003 600/109 |
| 2016/0114117 A1 | 4/2016 | Cook |
| 2016/0262603 A1 | 9/2016 | Molnar |
| 2016/0279365 A1 | 9/2016 | Esnouf |
| 2017/0072154 A1 | 3/2017 | Hoftman et al. |
| 2017/0196445 A1* | 7/2017 | Gardner .................. A61B 1/051 |
| 2017/0209022 A1 | 7/2017 | Molnar |
| 2018/0104427 A1* | 4/2018 | Avitsian ............ A61M 16/0459 |
| 2018/0169365 A1* | 6/2018 | Sawyer ............. A61M 16/0488 |
| 2019/0059710 A1 | 2/2019 | Molnar |

FOREIGN PATENT DOCUMENTS

| | | |
|---|---|---|
| WO | WO9405200 | 3/1994 |
| WO | 03/084719 A2 | 10/2003 |
| WO | 2008123934 A1 | 10/2008 |
| WO | 2009025843 A1 | 2/2009 |
| WO | WO2010120950 | 10/2010 |
| WO | 2012/080293 A2 | 6/2012 |
| WO | 2013/017535 A2 | 2/2013 |
| WO | 2015013172 | 1/2015 |

OTHER PUBLICATIONS

Bledso B., "Incubation Threatened by New Devices and Lack of Paramedic Practice", Patient Care, Jems.com; hittp://www.jems.com/article/patient-care/incubation-threatened-new-devi, printed Feb. 21, 2015, 8 pages.

Bledso B., "Incubation Threatened by New Devices and Lack of Paramedic Practice", Patient Care; http://www.jems.com/article/patient-care/intubation-threatened-new-devi, printed Mar. 20, 2015, 14 pages.

Vivasight, "Continuous Airway Control", http://surgery.utoronto.ca/Assets/Surgery+Digital+Assets/POS+Lectures/Surgical+Resident+Seminar.ppt, 7 pages.

Genzwuerker, MD. et al. "Laryngeal tube: a review of current literature" AJA-Online.com 2011:vol. 12, p. 22-33.

Kodali MD, "Capnography in emergency medicine-911" http://www.capnography.com/outside/922.htm., printed Feb. 21, 2015, 9 pages.

ETView Medical, Ltd., Announces the Appointment of David Amar, MD to Its Scientific Advisory Board, 2012; http://finance.yahoo.com/news/etview-medical-ltd-announces-appointment-104300770.html, Jun. 4, 2012, 3 pages.

ETView, "VivaSight-DL disposable dual lumen airway ventilation tube with integrated high resolution airway imaging system permitting airway control and lung isolation", http://www.etview.com/index_old.php, Jun. 21, 2012. 1 page.

ETView, VivaSight "Airway management for lung isolation—See the possibilities when you use the VivaSight product portfolio of fully integrated imaging/ventilations systems", 8 pages.

"How to Use a Jem Endotrachael Tube Changer," Endotrachael Tube Changers, Instrumentatio Industries, Inc., Bethal Park, PA, 2015, 2 pages.

ETView, VivaSight-SL, "Now, a major advance in continous visualization of the airways during the thoracic surgical procedures requiring lung isolation", 5 pages.

ETView Medical Ltd., "ETView Medical, Ltd., Announces Exclusive Patent License Agreement—Feb. 2, 2012", http://worldnetdaily.com.uk/markets/news/read/20671060/etview_medical, Jul. 5, 2012, 3 pages.

* cited by examiner

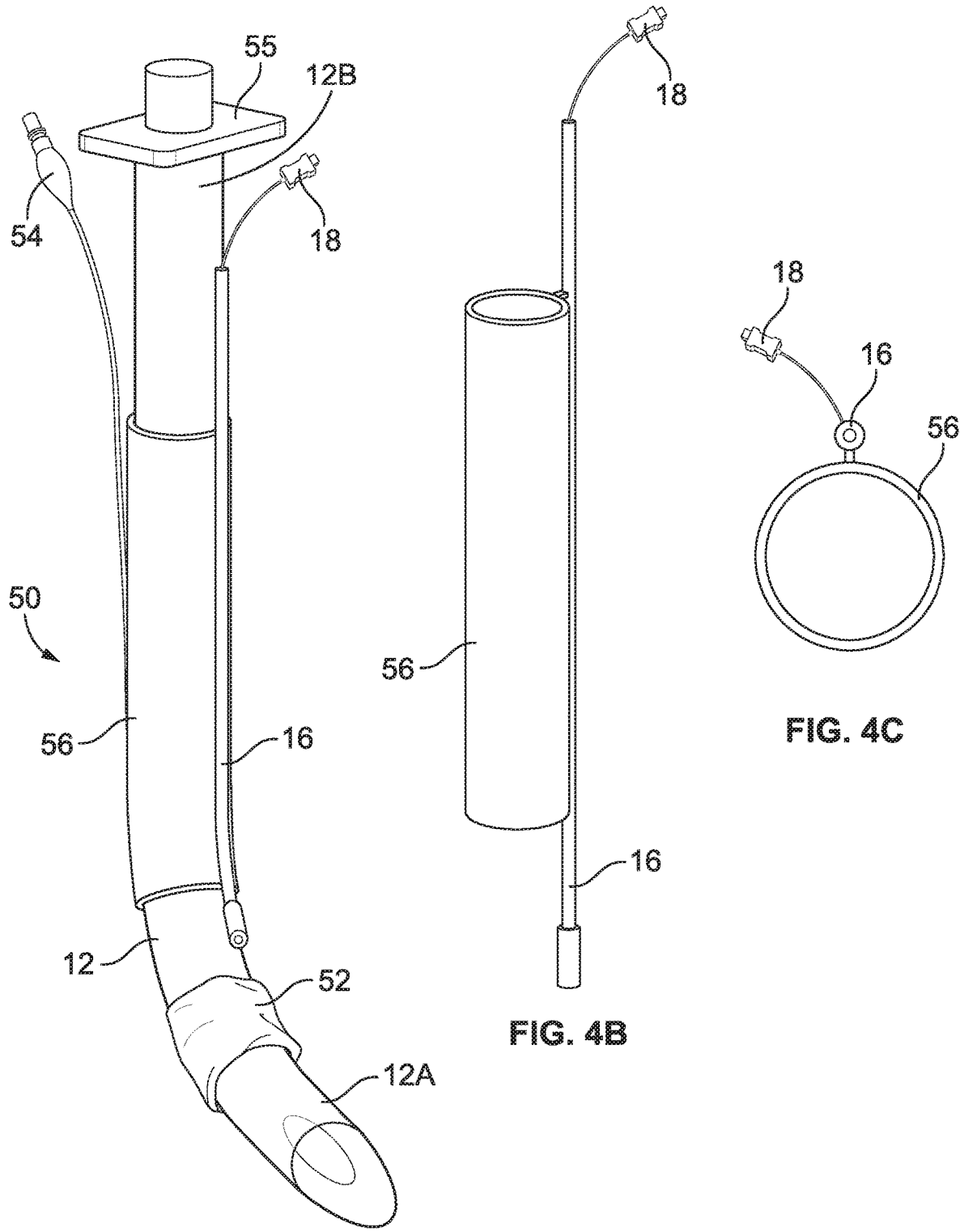

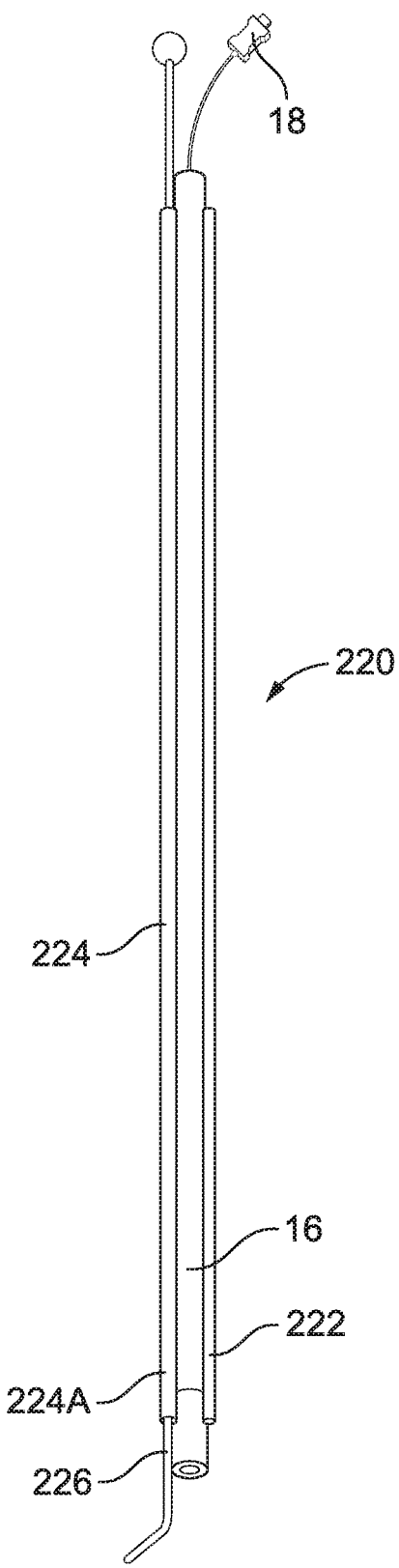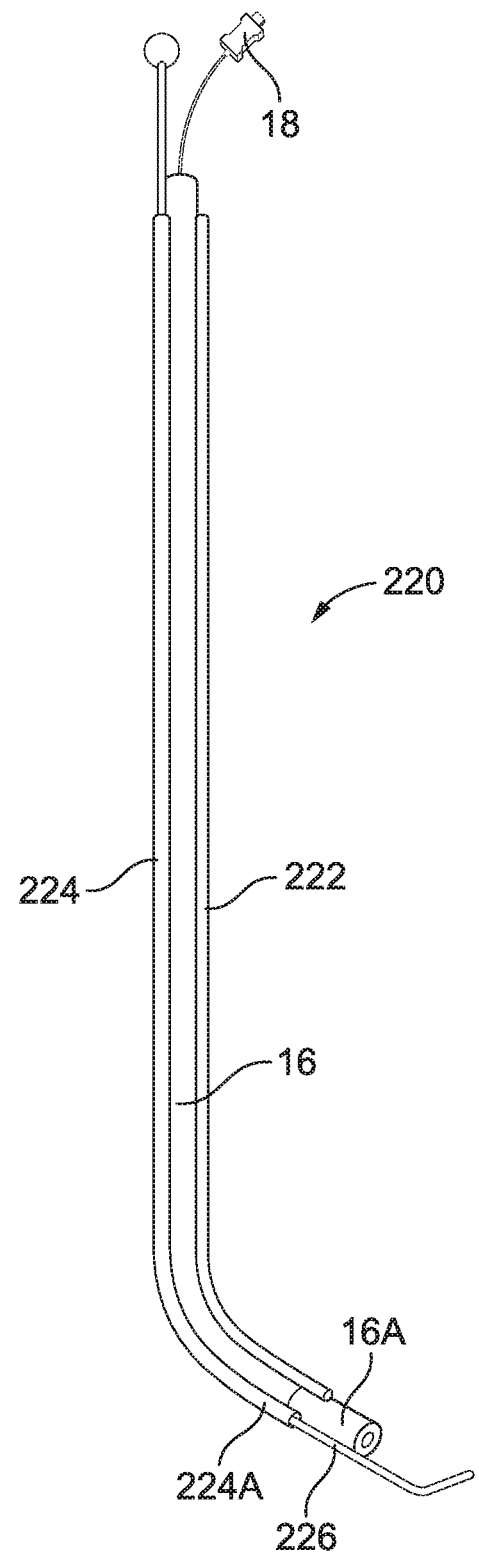
FIG. 12A  FIG. 12B

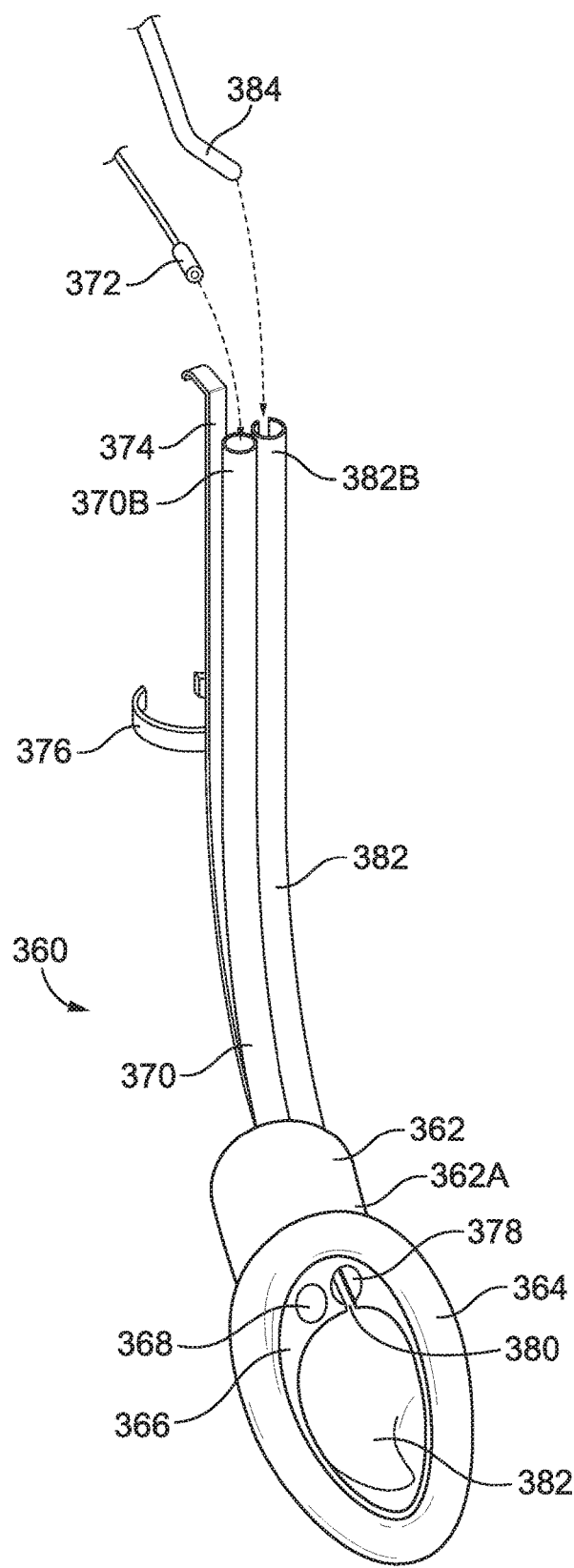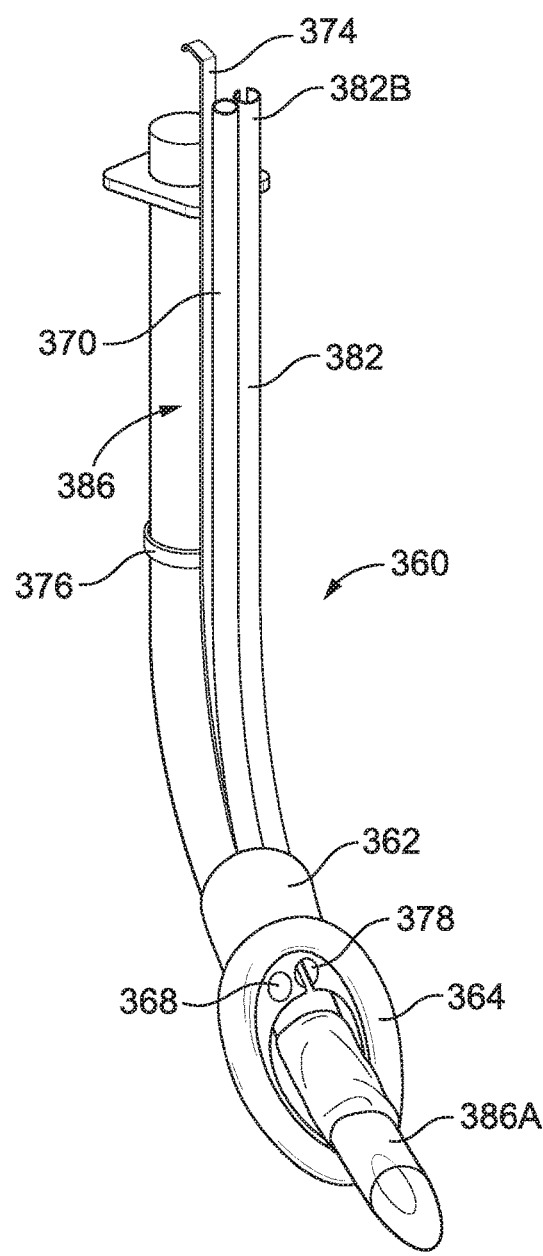
FIG. 17A
FIG. 17B

MEDICAL DEVICES WITH CAMERA AND METHODS OF PLACEMENT

FIELD OF THE INVENTION

The invention provides a set of disposable medical devices, including various intubating devices, which are combined with a disposable camera providing continuous visualization during and after placement in a patient. A sound device, such as a microphone, may be incorporated in many devices and provides continuous monitoring of breath and heart sounds in a patient. The continuous visualization and sound monitoring of the patient are in real time and enable remote monitoring as well. Methods for rapid and accurate placement of a medical device in a patient are provided as well.

BACKGROUND

Various devices are available to stabilize a patient and facilitate his breathing, feeding and medication delivery. Such devices are used in patients during surgical procedures, after certain traumas including spinal cord injuries, and in patients suffering from certain medical conditions including advanced Alzheimer disease. These devices include endotracheal tubes, airway devices, feeding tubes, oral airways, nasal cannulas and the like.

The process of placing a breathing tube in a patient is called intubation. Devices such as laryngoscopes, videolaryngoscopes, fiberoptic scopes, as well as other proprietary videoscopes have been developed. These devices provide accuracy for initial placement, but do not provide continuous visualization or mobility of the image after a medical device has been placed in a patient. Newer devices, such as Vivasight SL or DL endotracheal tubes, provide continuous visualization, but are costly because they depend on a single use of disposable cameras and they are not transferable from one medical device to another. The Totaltrack VLM supraglottic airway has a proprietary reusable camera for only its one device, and it cannot be transferred to other medical devices.

Thus, there remains the need for improved devices which can be easily monitored remotely by a qualified personal during placement and after placement for an adverse reaction. After a medical device has been placed in a patient, the need remains to monitor in real time the patient's possible adverse reactions such as for example, aspiration, airway secretion, apnea, etc.

Certain medical devices which provide continuous visualization are described in U.S. Pat. No. 9,415,179, and Patent Publications US 2016-0038008; US 2016-0038014; and US 2016-0262603. In these devices, a camera is placed inside of a camera tube which is a separate lumen sealed at the distal end. This prevents the camera from coming into a contact with a patient's body and allows for the camera to be reused in various devices and between different patients without the need for sterilization. While these devices may comprise a disposable camera, the devices still comprise a separate camera tube sealed at the distal end.

SUMMARY

The present invention provides a set of medical devices equipped with a disposable camera without a separate sealed camera tube. The camera can be transferred between various devices. Each of the devices can provide continuous visualization during intubation, extubation and while being positioned in the patient's body. The devices do not comprise a camera tube which is sealed at the distal end, thus the camera can be transferred between various devices.

The devices include a medical intubating device comprising a camera combined with a second device comprising an endotracheal tube, oral airway, tracheostomy tube, suction catheter, tubeless intubating device, supraglottic oral airway, truncated supraglottic oral airway, tool tube, ventilation cap, medical examination glove and/or stylet. The camera has a distal end and a proximal end and wherein the second device has a distal end and a proximal end. The distal end of the camera is in near proximity with the distal end of the second device. In some of the devices, the camera is attached to a tube. The camera is combined with the second device by the second device being placed into the tube. The position of the camera on the second medical device can be adjusted by sliding the tube along the proximal-distal axis of the second device.

In some of the devices, the camera is attached to at least one ring which may optionally comprise a clasp. The second device comprises a tubal body. The camera is combined with the second device by the ring being secured around the tubal body.

In some of the devices, the second device comprises a cuff. The camera is combined with the second device by being placed under the cuff such that the distal end of the camera is positioned distally to the cuff.

In some of the devices, the camera is attached to the tool tube and/or the stylet. The tool tube can be a slit wall tube and a bougie is insertable in the slit wall tube.

In some of the devices, the camera is attached to the tool tube and the stylet, and a bougie is placed in the tool tube. The bougie has a proximal end and a distal end, and wherein the distal end of the bougie protrudes distally from the tool tube and wherein the bougie protrudes distally to the distal end of the camera.

The second device can be an endotracheal tube and an inflatable cuff which is wrapped around the endotracheal tube near the distal end of the endotracheal tube, and wherein the camera is sealed externally along the proximal-distal axis of the endotracheal tube.

The second device can be the endotracheal tube with an inflatable cuff which is wrapped around the endotracheal tube near the distal end of the endotracheal tube, and wherein the camera is sealed externally along the proximal-distal axis of the endotracheal tube.

The second device can be the endotracheal tube with an inflatable cuff which is wrapped around the endotracheal tube and the camera near the distal end of the endotracheal tube, and wherein the distal end of the camera collects images distally to the cuff.

The second device can be the endotracheal tube with an inflatable cuff which is wrapped around the endotracheal tube and the camera is positioned near the distal end of the endotracheal tube, and wherein the endotracheal tube comprises a sleeve near the proximal end of the endotracheal tube, and wherein the camera is inserted into the sleeve.

The second device can be the tracheostomy tube comprising a tubal body with a plate and an inflatable cuff wrapped around the tubal body in proximity to the distal end of the tubal body, and wherein the camera is combined with tubal body externally by being inserted into an opening of the plate and being placed under the inflatable cuff.

The second device can be the endotracheal tube, wherein the endotracheal tube is combined with a tool tube externally, wherein the tool tube can optionally comprise a cap, and wherein the endotracheal tube is held in place on the endotracheal tube with at least one ring, wherein the camera slides inside the tool tube and wherein at least one of the following tools is optionally inserted in the tool tube: biopsy forceps, esophageal stethoscope, cuff tube, suction tube, nasogastric tube, stylet and/or bougie.

The second device can be the endotracheal tube, wherein the endotracheal tube is combined with a tool tube externally, wherein the tool tube can optionally comprise a cap, and wherein the endotracheal tube is held in place on the endotracheal tube with a cuff which wraps around the tool tube and endotracheal tube, wherein the camera slides inside the tool tube and wherein at least one of the following tools is optionally inserted in the tool tube: biopsy forceps, esophageal stethoscope, cuff tube, suction tube, nasogastric tube, stylet and/or bougie.

The second device can be the oral airway which comprises a curved tubal body with a proximal end and a distal end, wherein the tubal body has a lumen and comprises a plate at the proximal end of the curved tubal body, and wherein the camera is combined with the tubal body by being inserted through an opening in the plate and then through an opening in the wall of the curved tubal body, the distal end of the camera being inside the lumen and in near proximity with the distal end of the curved tubal body.

The second device can be the oral airway which comprises a hollow curved tubal body with a proximal end and a distal end, wherein the hollow tubal body has a lumen and comprises a plate at the proximal end of the curved tubal body, and wherein the camera is combined with the tubal body by being inserted through an opening in the plate and placed along the hollow curved tubal body externally, wherein the second device further comprises a second hollow tubal body which is aligned with the hollow curved tubal body, and wherein a balloon wraps around the hollow curved tubal body, the second hollow tubal body and the camera.

The second device can be the oral airway device which comprises a two-part tubal body made from an outer cylindrical tube wall and an inner cylindrical tube, wherein the inner cylindrical tube is at least partially inserted into the outer cylindrical tube, wherein the inner cylindrical tube wall is extendable, the camera is combined with the oral airway device by being inserted inside the two-part tubal body through an opening located in proximity to the proximal end of the tubal body, the second device further optionally comprises a bougie.

The second device can be the oral airway device which comprises two hollow tubes, a first hollow tube and a second hollow tube, wherein the first hollow tube is inserted inside the second hollow tube partially, the first hollow tube is longer in length than the second hollow tube, the first hollow tube being insertable and removable from the second hollow tube, the first hollow tube comprising a tapered tongue at the distal end, the second hollow tube comprises a plate at the proximal end, wherein the camera is inserted through an opening in the plate and is combined with the second device by being positioned externally along the second hollow tube, and wherein the oral airway device comprises a tool lumen.

The second device can be the oral airway device which comprises a curved tubal body with a central lumen and a plate at a proximal end of the curved tubal body, wherein the a cuff wraps around the curved tubal body and a handle is attached to the cuff, wherein the cuff is movable from the proximal end on the curved tubal body to the distal end of the curved tubal body with the handle and wherein the camera is combined with the oral airway device by being inserted in an opening in the plate, positioned along the curved tubal body externally and wherein the cuff wraps over the camera such that the distal end of the camera is positioned distally to the cuff.

The second device can be the oral airway device which comprises a curved tubal body with a central lumen, wherein two tubes are inserted in the central lumen, the first hollow tube and a second hollow tube with a slit wall, wherein the first tube and the second tube are each attached to the wall of the oral airway device and wherein a distal end of the first tube and a distal end of the second tube are near a distal end of the curved tubal body, and wherein a camera is insertable in the first tube and a bougie and/or a medical tool is insertable in the second tube. A cuff wraps around the curved tubal body near the distal end of the curved tubal body.

The second device can be the supraglottic oral airway, wherein the supraglottic oral airway comprise a tubal body with a central lumen, wherein a soft cuff wraps around the distal end of the tubal body, wherein the wall of the tubal body comprises a first lumen and a second lumen with a slit, and wherein a camera is insertable in the first lumen and a bougie is insertable in the second lumen, and wherein the slit connects the second lumen with a central lumen of the tubal body. In some embodiments, the tubal body is truncated and the device comprises a handle with a holder, a first tube which connects with the first lumen and a second tube with slit wall which connects with the second lumen with a slit.

Also provided are methods of intubating a patient, in which any of the medical devices are inserted by guiding the insertion with a bougie under the continuous visualization with the camera.

BRIEF DESCRIPTION OF THE DRAWINGS

FIG. 1A is an embodiment in which the camera is positioned proximally to a cuff. FIG. 1B is an embodiment in which the camera is positioned distally to the cuff.

FIG. 4A depicts an endotracheal device in which an endotracheal tube is inserted inside of a tube attached to a camera. FIG. 4B depicts a camera attached to a tube. FIG. 4C is a cross-sectional view of the camera attached to the tube of FIG. 4B.

FIG. 12A is embodiment of a camera assembled with a stylet. In the embodiment of FIG. 12B, the stylet is curved.

FIG. 17A depicts a truncated supraglottic airway device with a camera and slit wall tube. FIG. 17B depicts positioning of an endotracheal tube into the supraglottic airway device of FIG. 17A.

DETAILED DESCRIPTION

The present invention provides medical devices equipped with a camera for intubation, ventilation, feeding and monitoring of a patient. The present invention also provides methods for rapid and accurate placement of a medical device in a patient and remote continuous real-time monitoring of the patient after the placement.

The invention provides a set of medical devices equipped with a disposable camera which can be transferred between the devices as needed. These devices provide continuous visualization of any of the following in a patient in real time: nasopharynx, pharynx/hypo pharynx, supraglottic structures, airway, internal organ anatomy, vocal cords during normal and abnormal ventilation. The devices also allow detection of abnormal anatomy and abnormal vocal cord movements.

A camera in the present devices comprises a digital camera coupled to a power cord. The digital camera may comprise CCD (charge-coupled device) and/or CMOS (complementary metal-oxide semiconductor) sensors. The captured images may be transmitted either with a wire or wirelessly.

Figure 1A:
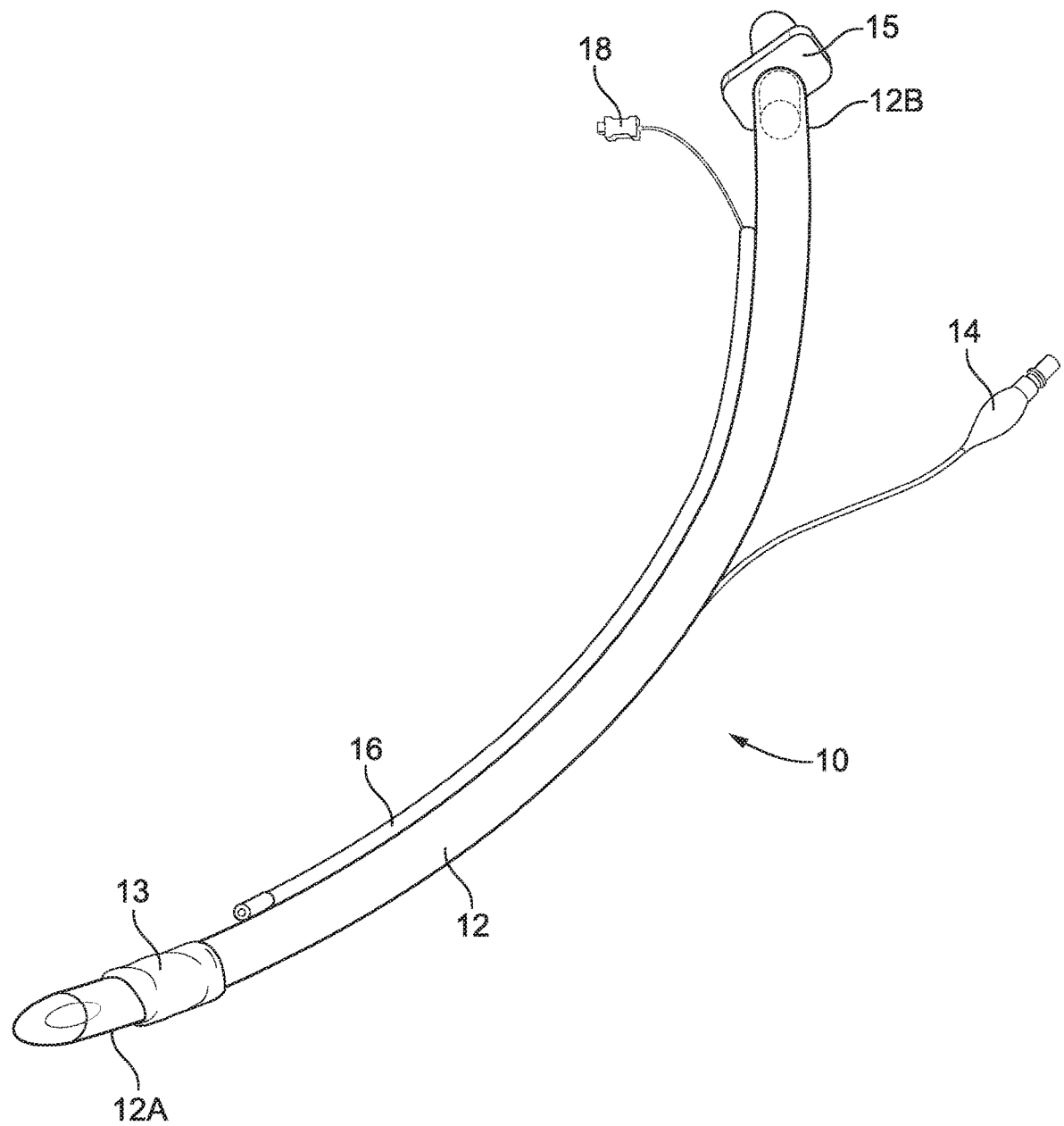
FIGS. 1A and 1B depict two embodiments for an endotracheal device equipped with a camera.

Referring to FIG. 1A, this embodiment provides an endotracheal device, generally 10. The endotracheal device 10 comprises an endotracheal tube 12 with a distal end 12A and a proximal end 12B. The endotracheal tube 12 comprises an inflatable cuff 13 wrapped around the endotracheal tube 12 proximally to the distal end 12A. The cuff 13 can be inflated with means 14 after the endotracheal tube 12 is placed in a patient. The endotracheal tube 12 comprises a plate 15 positioned near the proximal end 12B. The plate 15 is perpendicular to the endotracheal tube 12 and prevents the endotracheal tube 12 from sliding into the patient's body after the device 10 has been placed into the patient.

A camera 16 is sealed externally along the proximal-distal (12B-12A) axis of the endotracheal tube 12. A diameter of the camera 16 is not limited by a diameter of the endotracheal tube 12. The diameter of the camera 16 can be larger or smaller than the diameter of the endotracheal tube 12. This may be particularly beneficial for pediatric patients and patients with abnormal anatomy.

In the embodiment of FIG. 1A, the camera 16 is positioned proximally to the cuff 13. The camera 16 may comprise a battery (not shown), and/or electric wire 18 for connection to an external device such as a computer and monitor (not shown). The camera 16 may also comprise means for transmitting images wirelessly. The camera 16 may further comprise a light source which can be built-in the camera 16.

At least in some applications, the camera 16 is a digital camera equipped with a chip and the camera 16 collects and transmits images continuously. The camera 16 can be connected wirelessly or hard-wired with a computer network (not shown) which collects and analyzes images obtained by the camera 16. This arrangement permits for remote, continuous and real-time monitoring of the endotracheal device 10 during placement and after-placement in a patient. Thus, an accurate and rapid placement of the endotracheal device 10 can be achieved. Further and because the camera 16 continues to acquire images after the endotracheal device 10 is placed inside of a patient, the patient can be monitored in real time for adverse reactions such as bleeding, airway obstruction, shifting or malfunctioning, etc. of the endotracheal device 10 and other reactions. The endotracheal device 10 may continue to transmit images and information for as long as it remains in a patient.

The endotracheal device 10 can be further equipped with a sound-monitoring device (not shown) such as microphone which can monitor heart beats and breathing tones and can be connected by wire or wirelessly to a remote device which collects and monitors patient's vital signals.

In the embodiment of FIG. 1A, the camera 16 is placed proximally to the cuff 13 and externally to the endotracheal tube 12. It will be understood that the endotracheal device 10 can be built with any endotracheal tube 12, including single-lumen and double-lumen tubes. The endotracheal device 10 can be used for either pediatric or adult patients. The endotracheal device 10 can be made in various sizes.

Figure 1B:
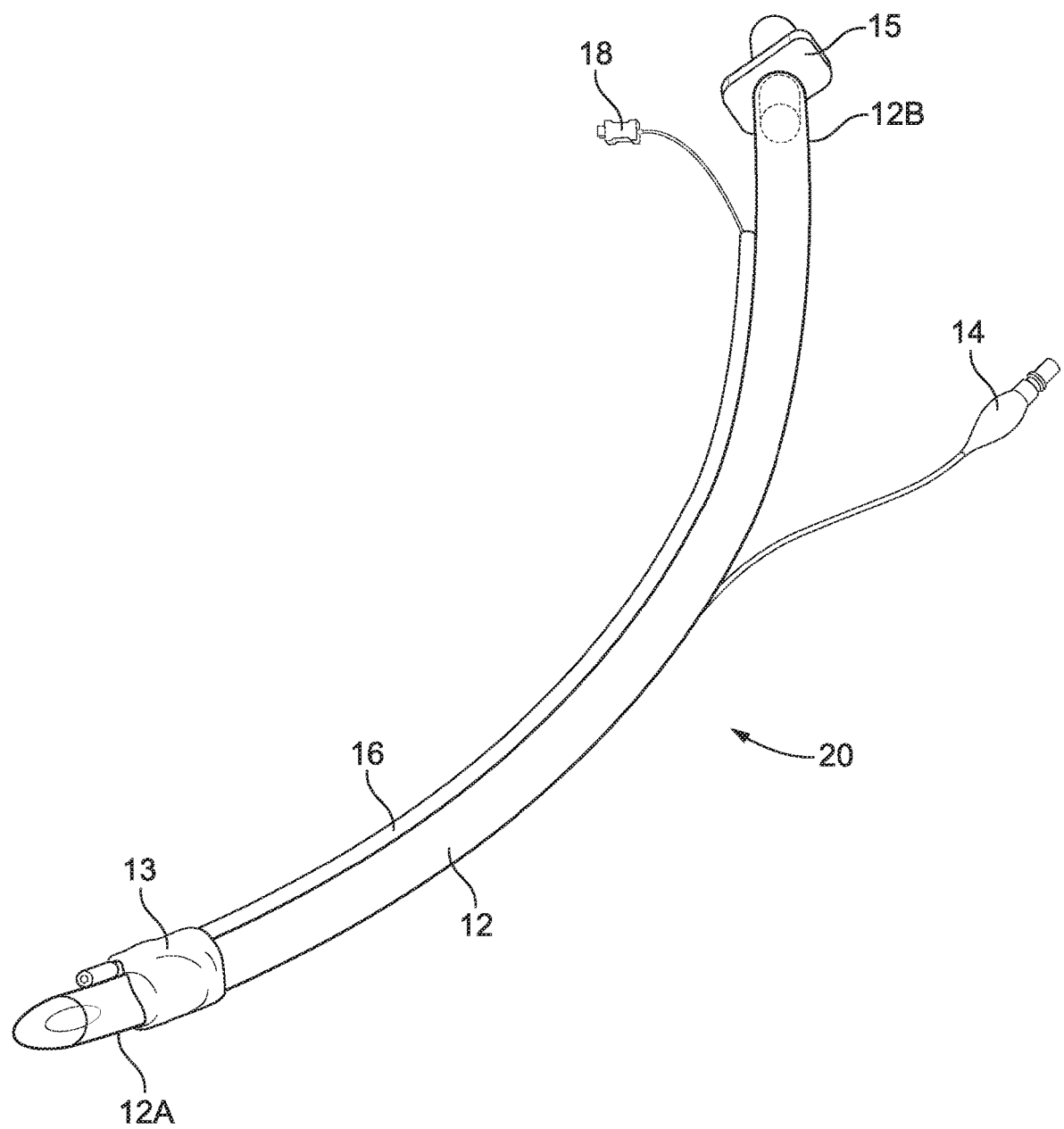

FIG. 1B is another embodiment of an endotracheal device 20 which comprises the endotracheal tube 12 with the cuff 13 and other elements as described in connection with FIG. 1A. In the embodiment of FIG. 1B, the camera 16 is sealed externally to the endotracheal tube 12 along the distal-proximal axis 12A-12B. Unlike the embodiment of FIG. 1A, the camera 16 in the embodiment of FIG. 1B is placed under the cuff 13 and it collects images distally from the cuff 13. It will be understood that the endotracheal device 20 can be built with any endotracheal tube 12, including single-lumen and double-lumen tubes. The endotracheal device 20 can be used for either pediatric or adult patients. The endotracheal device 20 can be made in various sizes.

It will be readily appreciated by a person of skill, that in the embodiments of FIGS. 1A and 1B, the camera 16 is sealed along the endotracheal tube 12. In other embodiments, the camera 16 can be combined with the endotracheal tube 12 such that the camera 16 can slide up and down along the proximal-distal axis 12B-12A of the endotracheal tube 12.

The camera 16 can be combined with the endotracheal tube 12 by being sealed with an adhesive to the endotracheal tube 12. In alternative, the camera 16 can be attached to the endotracheal tube 12 such that the camera 16 can be separated from the endotracheal tube 12 and transferred to another medical device. This reversible attachment can be achieved by clipping the camera 16 to the endotracheal tube 12 with at least one clip or by tying the camera 16 to the camera tube 12 with a rope, thread or and/or by plastic and/or robber band. In alternative, the camera 16 can be equipped with at least one ring which can slide over the endotracheal tube 12 and thereby combine the camera 16 with the endotracheal tube 12 such that the camera 16 can slide along the endotracheal tube 12.

Figures 2A, 2B:
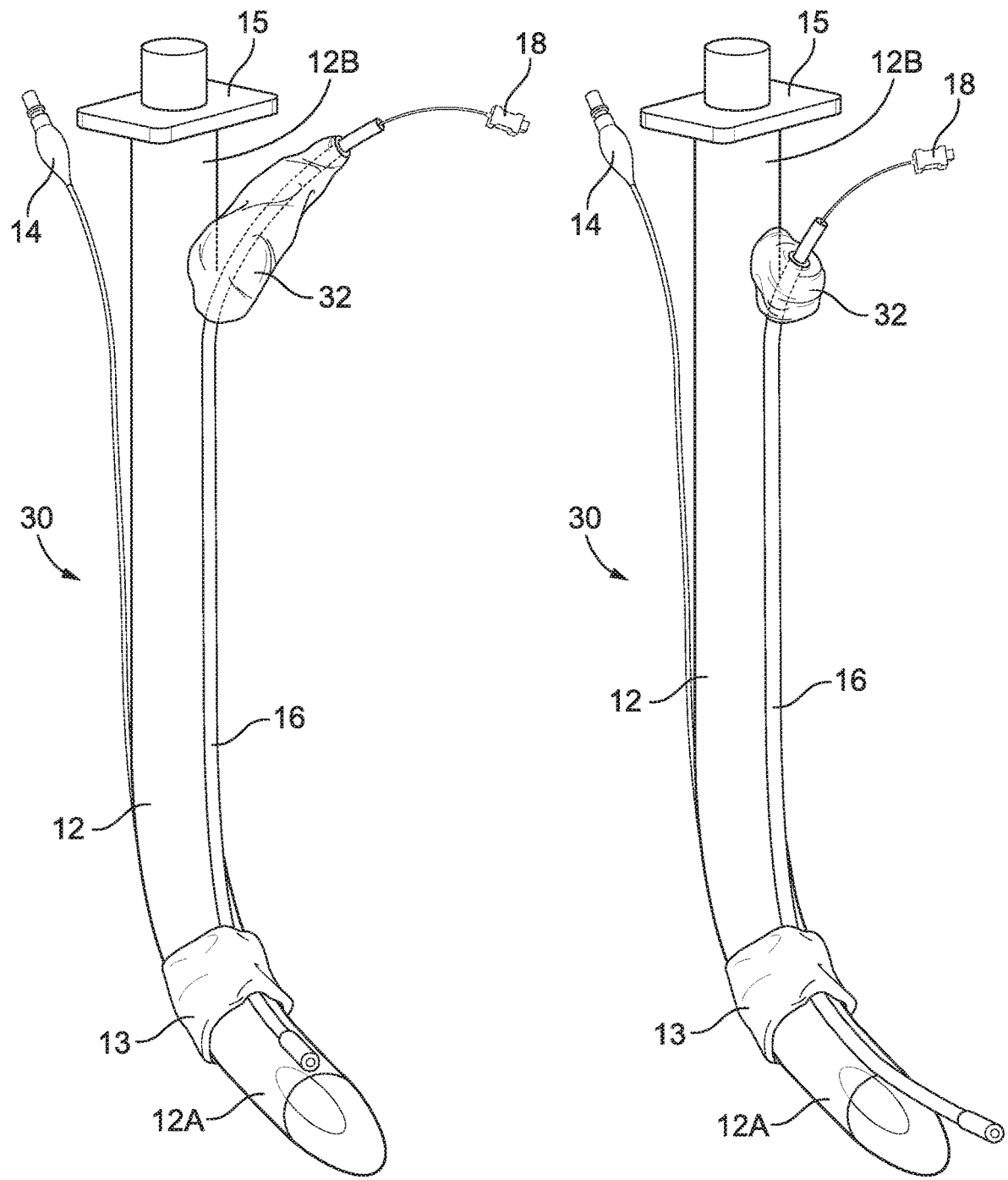
FIGS. 2A and 2B depict side views of an alternative embodiment for an endotracheal device equipped with a camera delivered through a sliding sleeve. A camera can slide along the endotracheal tube.

FIGS. 2A and 2B provide another embodiment for an endotracheal tube 30 equipped with a sleeve 32. In this embodiment, an endotracheal tube 12 comprises a distal end 12A and a proximal end 12B. The sleeve 32 is placed near the proximal end 12B. An inflatable cuff 13 is wrapped around the endotracheal tube 12 near the distal end 12A. The cuff 13 can be inflated with means 14. A camera 16 is combined with the endotracheal tube 12 by being placed through the sleeve 32, along the endotracheal tube 12 and under the cuff 13. The camera 16 can slide along the proximal-distal axis 12B-12A such that the camera 16 can be positioned right at the distal end 12A of the endotracheal tube 12, as shown in FIG. 2A. The camera 16 can also slide further distally under the cuff 13 such that the camera 16 is now positioned distally to the distal end 12A of the endotracheal tube 12 and provides images distally to the distal end 12A of the endotracheal tube 12, as shown in FIG. 2B. The sleeve 32 is made of a flexible material, such as for example plastic or rubber. This allows for sleeve 32 to easily collapse as needed when the camera 16 moves distally along the endotracheal tube 12. Compare the sleeve 32 in FIG. 2B where the sleeve 32 in the collapsed position versus the sleeve 32 in FIG. 32A where the sleeve 32 is in a fully extended position.

At any time, a practitioner can manipulate the positioning of the camera 16 through the sleeve 32, including to move the camera 16 proximally or distally, and/or to remove the camera 16 from the patient while the endotracheal tube 12 still remains in place in the patient. This arrangement allows for transferring the camera 16 between different devices. This arrangement also allows for adjusting the position of the camera 16 in the patient, depending on an area that needs to be monitored. It will be appreciated that the device 30 can comprise more than one camera. In these further embodiments, a second camera can provide additional images from a location proximal or distal to the camera 16.

A particularly important advantage can be obtained by combining the camera 16 with a bougie, flexible stylet or any other tool which can be used for guiding the placement of the endotracheal tube 12 under continuous visualization from the camera 16.

Figures 3A, 3B, 3C:
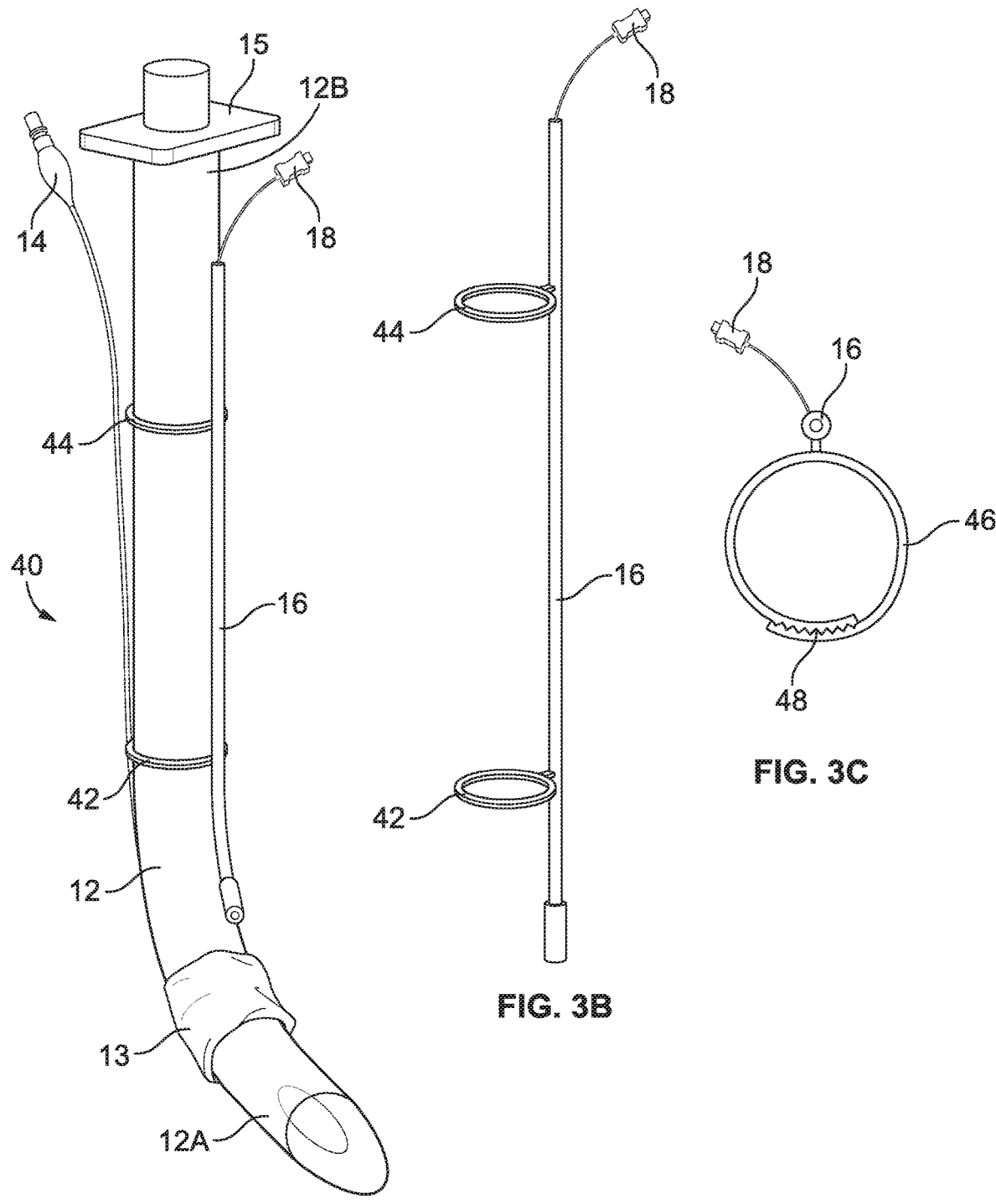
FIG. 3A, depicts an endotracheal device equipped with a camera comprising rings.
FIG. 3B is a side view of the camera comprising two rings.
FIG. 3C is a cross-sectional view through a camera showing an adjustable sliding ring with a clasp attached to the camera.

FIG. 3A provides a further embodiment of an endotracheal device 40 which comprises an endotracheal tube 12 with a distal end 12A and a proximal end 12B and a plate 15 near the proximal end 12B.

The endotracheal tube 12 comprises an inflatable cuff 13 wrapped around the endotracheal tube 12 proximally to the distal end 12A. The cuff 13 can be inflated with means 14 after the endotracheal tube 12 is placed in a patient. The endotracheal device 40 comprises a camera 16 with electric wire 18. In some embodiments, the camera 16 can be wireless.

In the embodiment of FIG. 3A, the camera 16 is attached to the endotracheal tube 12 externally with rings 44 and 42 which wrap around the endotracheal tube 12. The endotracheal tube 12 is combined with the camera 16 by placing the endotracheal tube 12 through the rings 42 and 44. It will be appreciated that the positioning of the camera 16 along the distal-proximal axis (12A-12B) of the endotracheal tube 12 can be easily adjusted by adjusting the positioning of the rings 42 and 44.

The camera 16 comprises two rings 42 and 44 as shown in more detail in FIG. 3B depicting rings 42 and 44 attached to the disposable camera 16. The number of rings can vary between different embodiments. In various embodiments, from one to ten rings can be attached to the camera 16. In some embodiments, rings can have an adjustable diameter. This can be achieved by equipping a ring with a clasp.

At least in some embodiments, a ring 46 has a clasp 48 as shown in FIG. 3C which is a cross-sectional view of the camera 16 to which the ring 46 is attached. The clasp 48 permits secure connection of the camera 16 to tubal devices of various diameters because the diameter of the ring 46 can be adjusted as needed. Thus, the same camera 16 with the ring 46 can be used on a pediatric endotracheal tube and an endotracheal tube of the adult size. It will be appreciated that the camera 16 with the ring 46 can be combined not only with an endotracheal tube, but with any other medical tubal device. For example, the camera 16 can be combined with an endotracheal tube, oral airway and any other devices described in this disclosure.

FIG. 4A provides a further embodiment of an endotracheal device 50 which comprises an endotracheal tube 12 with a distal end 12A and a proximal end 12B. The endotracheal device 50 may comprise a cuff 52 which is wrapped around the endotracheal tube 12 slightly above the distal end 12A, and which can be inflated with means 54. The endotracheal tube 12 can also comprise a plate 55 which is perpendicular to the tubal body 12 and is located near the proximal end 12B. After the intubation, the plate 55 remains outside the patient's body and prevents the endotracheal tube 12 from sliding down into the patient.

As shown in FIG. 4A and more in detail in FIG. 4B, a camera 16 is attached along the body of a tube 56. The diameter of the tube 56 is larger than the diameter of the endotracheal tube 12. The endotracheal tube 12 can be placed inside of the tube 56 such that the camera 16 can be positioned along the endotracheal tube 12. As can be appreciated from FIG. 4A, the tube 56 can slide along the endotracheal tube 12. Accordingly, the camera 16 can be placed closer or further away from the cuff 52. FIG. 4B shows the attachment of the camera 16 to the tube 56. FIG. 4C is a cross-sectional view through the camera 16 and the tube 56 showing that the camera 16 is sealed to the tube 56. In the drawings 4A-4C, the camera 16 comprises a wire 18. Other embodiments include those in which a wireless camera is used. As can be appreciated from FIG. 4A, the tube 56 can rotate around the tube 12. Thus, the camera 16 can provide a 360-degree panoramic view of an area inside the patient's body.

Figure 5A:
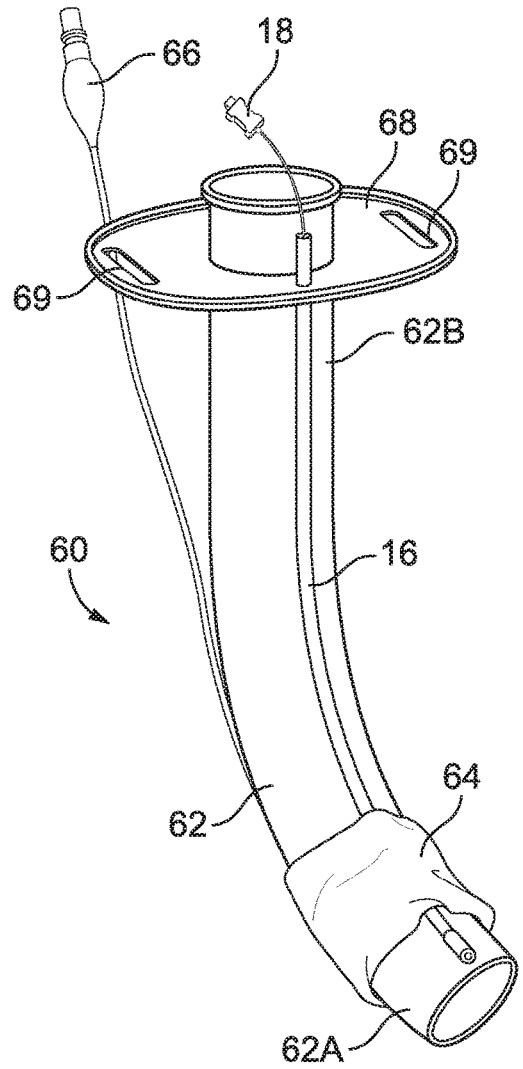
FIG. 5A depicts a tracheostomy tube equipped with a camera externally.

Further embodiments provide various tracheostomy tubes equipped with a camera. FIG. 5A depicts a side view of an embodiment for a tracheostomy device, generally 60. The device 60 comprises a tubal body 62 with a distal end 62A and a proximal end 62B. An inflatable cuff 64 is wrapped around the tubal body 62 in proximity to the distal end 62A, but never at the very distal end 62A. The cuff 64 can be inflated with a device 66 after proper placement of the device 60 in a patient. At the proximal end 62B, the tubal body 62 protrudes through a plastic plate 68 such that some portion of the tubal body 62 is proximal to the plastic plate 68 and will remain outside of a patient's neck after the device 60 is positioned in the patient.

The plastic plate 68 may be oval in shape with the tubal body 62 protruding from the plate 68 in the middle of the oval plastic plate 68. The plastic plate 68 may have two openings 69, one on each side of the plate such that the device 60 can be secured around patient's neck with some bandage by tying the device 60 through the openings 69 around patient's neck.

In the embodiment of FIG. 5A, a camera 16 is sealed or otherwise attached to the tubal body 62 externally. The camera 16 is sealed or otherwise attached externally along the proximal-distal (62B-62A) axis to the tubal body 62. The camera 16 is placed under the cuff 64 such that the cuff 64 wraps over the camera 16 and the camera 16 can capture images near the distal end 62A.

A wire 18 of the camera 16 protrudes through the plastic plate 68 and remains outside of patient's neck. In further embodiments, the camera 16 can be in communication with a monitoring device wirelessly. A light source can be added to camera 16.

Figure 5B:
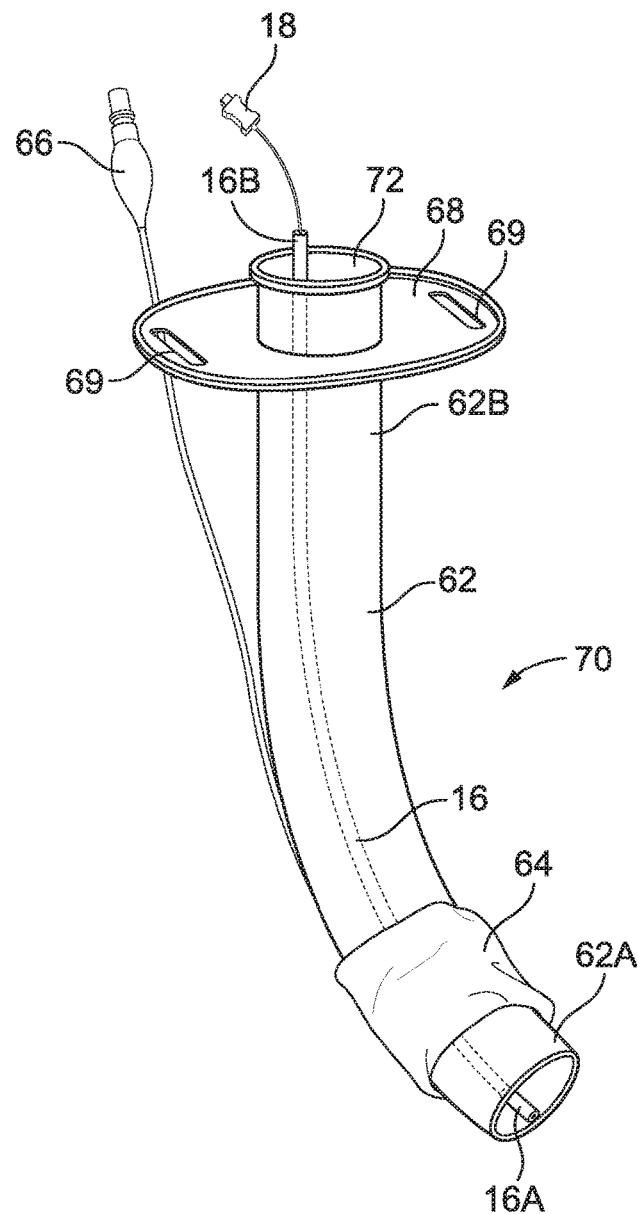
FIG. 5B depicts a tracheostomy tube equipped with a camera placed inside of the tracheostomy tube.

FIG. 5B depicts another embodiment for a tracheostomy device, generally 70. In this embodiment, the device 70 comprises the same tubal body 62, cuff 64, plate 68 and other components as was discussed in connection with the device 60.

However, unlike the device 60, a camera 16 is placed inside of a lumen 72 of the tubal body 62. The camera 16 may be sealed or otherwise attached internally to the tubal body 62 along the proximal-distal (62B-62A) axis such as the distal end 16A of the camera 16 is in close proximity with the distal end 62A of the tubal body 62. A proximate end 16B of the camera 16 remains outside the patient's body. The camera 16 can be connected by electrical wire 18 to a monitoring device (not shown). In other embodiments, the camera 16 communicates with a monitoring device wirelessly. In some embodiments, the camera 16 comprises a light source.

Figure 6A:
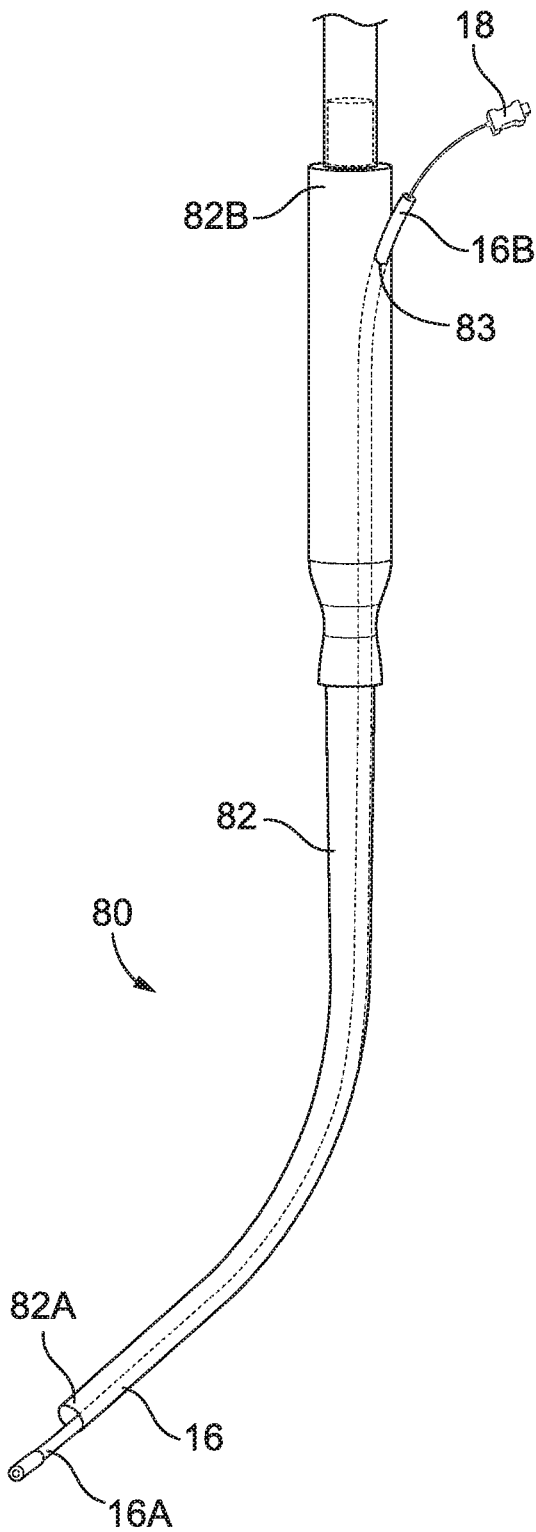
FIG. 6A depicts a suction catheter equipped with a camera internally.

Referring to FIG. 6A, this embodiment provides a suction catheter with a camera, generally 80. The suction catheter 80 comprises a hollow tubal body 82 which is not flexible in the embodiment of FIG. 6A. In other embodiments, a suction catheter can be any suction catheter known in the art. A camera 16 is positioned inside the suction catheter body 82 through an opening 83 which is in near proximity with a proximal end 82B of the suction catheter 82. The camera 16 may comprise wire 18. The distal end 16A of the camera 16 is aligned with the distal end 82A of the suction catheter 82, while the proximal end 16B of the camera 16 protrudes outside the patient's body such that the camera 16 can be pulled out from the patient while the catheter body 82 still remains in the patient.

Figure 6B:
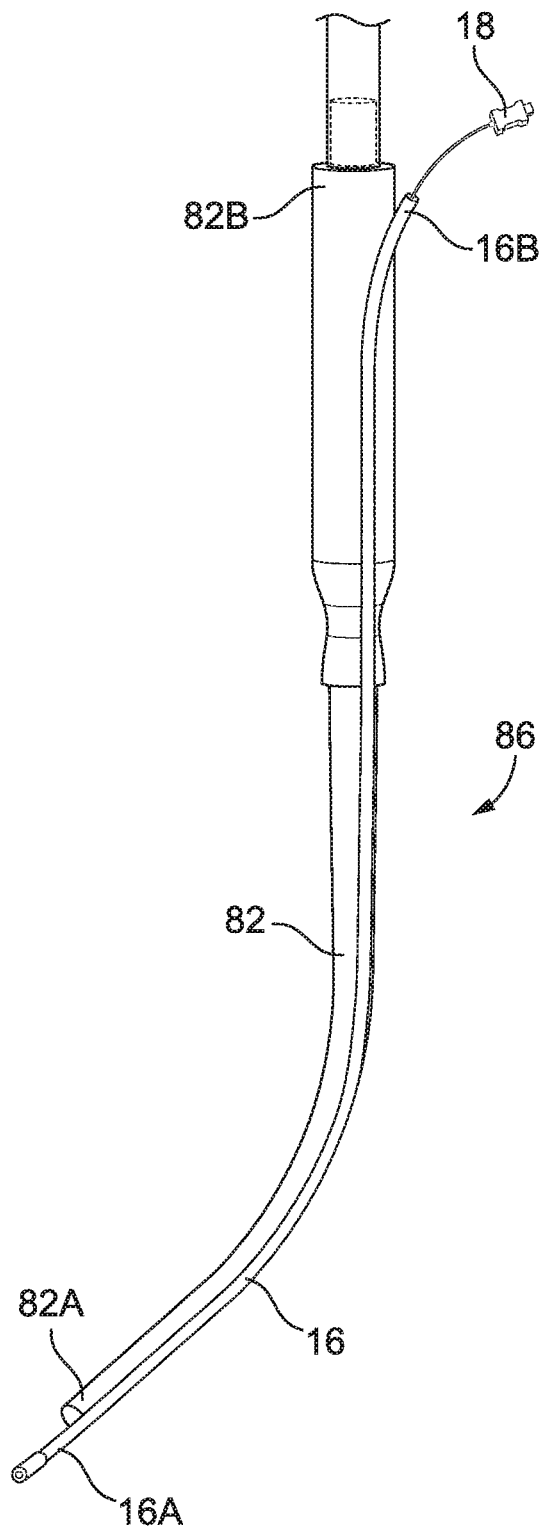
FIG. 6B depicts a suction catheter equipped with a camera externally.

Another embodiment of a suction catheter 86 is shown in FIG. 6B. In this embodiment, the camera 16 is placed externally along the suction tube 82. The camera 16 can be glued or otherwise attached to the body 82 along the proximal-distal axis (82B-82A). The distal end 16A of the camera 16 is distal to the distal end 82A of the suction catheter body 82. The proximal end 16B of the camera 16 is near the proximal end 82B of the suction catheter body 82. The device 86 can work with suction caps.

Figure 7A:
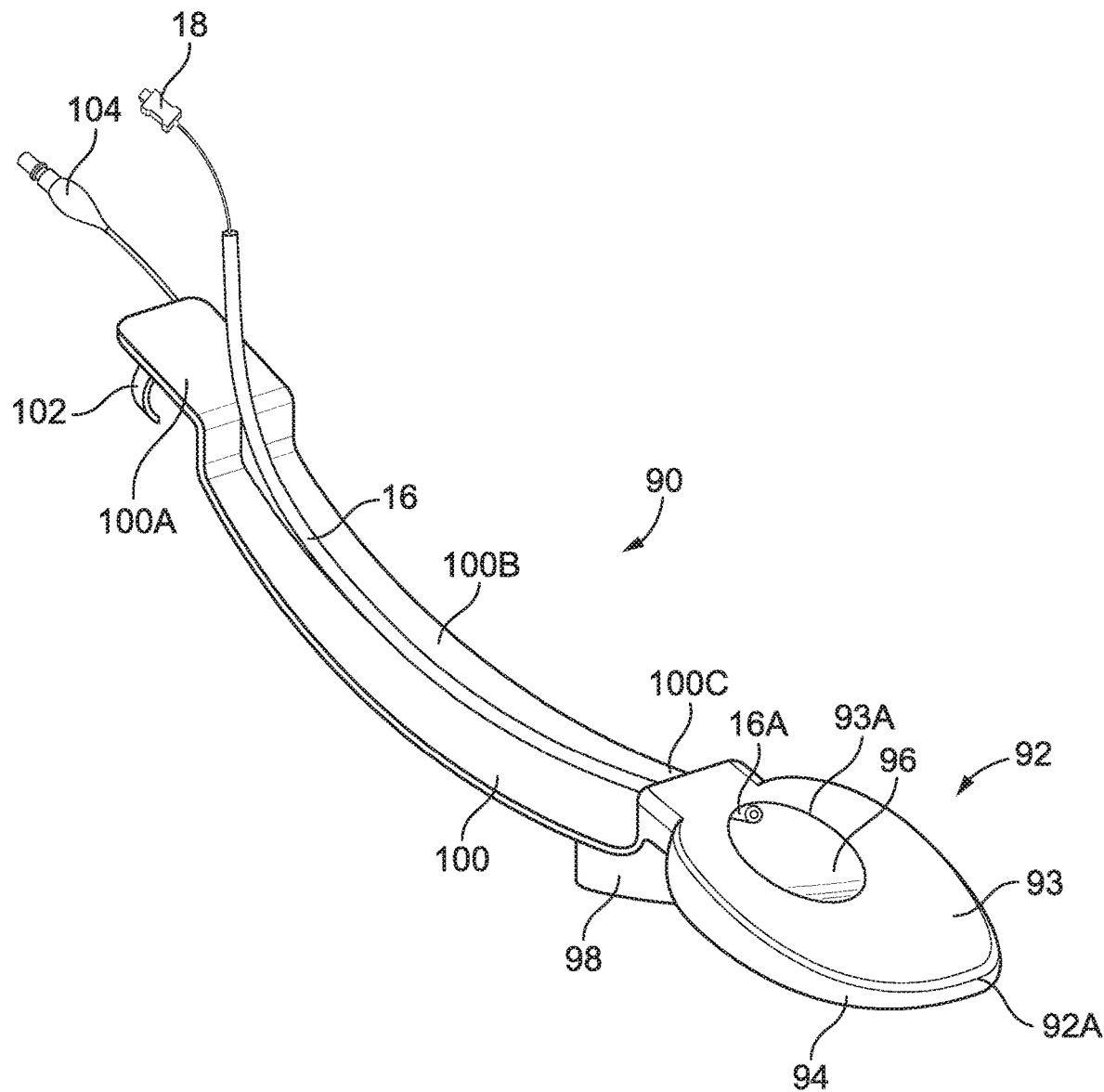
FIG. 7A depicts a tubeless intubating device equipped with a camera.

Further embodiments provide a tubeless intubating device shown in FIGS. 7A-7D, generally 90. The tubeless intubating device 90 comprises an ellipsoid body 92 which has an upper oval surface 93 with a lumen opening 93A on the upper oval surface 93 of the ellipsoid body 92 as shown in FIG. 7A. The upper oval surface 93 is connected to the bottom half-ellipsoid surface 94 as shown in FIG. 7A such that the distal end 92A of the ellipsoid body 92 is tapered because the bottom half-ellipsoid surface 94 is tapered at the distal end 92A. The ellipsoid body 92 encloses a lumen 96 which opens onto the upper oval surface 93 with the lumen opening 93A. The lumen 96 opens on the proximal side of the bottom half-ellipsoid surface 94 with a canal 98 which connects to the bottom half-ellipsoid surface 94 and extends beneath the bottom half-ellipsoid surface 94. The bottom half-ellipsoid surface 94 also connects to a handle 100.

The handle 100 comprises three parts connected together: the proximal part 100A, the middle part 100B and the distal part 100C. The proximal part 100A may be made in flat rectangle shape with a ring-holder 102 attached on the bottom surface of the proximal part 100A. The 100A part bends down at about a 90-degree angle at its distal part where it connects to the middle part 100B. The middle part 100B is also of flat rectangle shape and may vary in length. As can be seen from FIG. 7A, the canal 98 is connected to the bottom surface of the middle part 100B at the distal portion of the middle part 100B. The middle part 100B connects to the distal part 100C at its distal end. The middle part 100B bends up at about a 90-degree angle at the distal part and connects to the distal part 100C. The distal part 100C connects by its distal end to the oval upper surface 93 of the ellipsoid body 92.

A camera tube 16 is attached along the handle 100 on its upper surface such that the camera 16 extends along the handle 100 from its proximal end 100A and all the way into the distal portion 100C. The camera 16 can slide along the proximal-distal axis of the handle 100. The camera 16 may further comprise a light source. In some embodiments, the ellipsoid body 92 can comprise an inflatable cuff (not shown in FIG. 7A) which can be inflated with a means 104.

In some embodiments, the handle 100 can be made of flexible material. In other embodiments, the tubeless intubating device 90 can be designed without the cuff. In some embodiments, the camera 16 is fixed to the handle 100. In other embodiments, the camera 16 can slide along the proximal-distal axis of the handle 100. The distal end 16A of the camera 16 is aligned inside the lumen 96 and can capture images at this location.

The tubeless intubating device 90 can be used for intubating a patient with an endotracheal tube of any size under continuous visualization of the camera 16. The tubeless intubating device 90 can be also used for extubation and for reintubation of a patient. It can also act as a supraglottic device with an endotracheal tube inflated with the cuff.

Figure 7B:
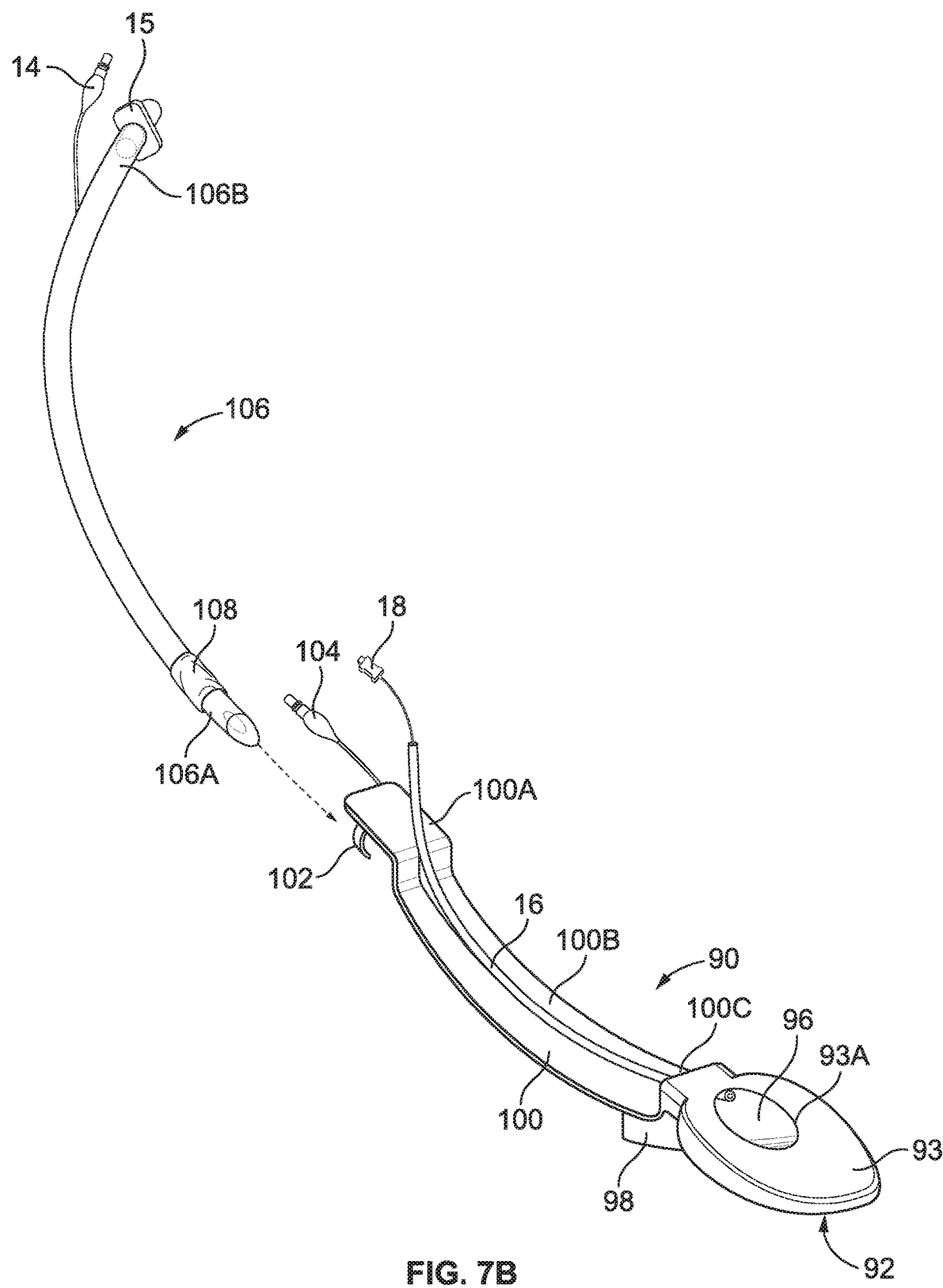
FIG. 7B depicts combining the tubeless intubating device of FIG. 7A with an endotracheal tube.

As shown in FIG. 7B, an endotracheal tube 106 can be loaded onto the tubeless intubating device 90 such that the proximal end 106B of the endotracheal tube 106 is secured on the tubeless intubating device 90 with the ring holder 102. It will be appreciated that any endotracheal tube can be loaded into the device 90 and inserted into a patient.

As can be seen in FIG. 7B, the endotracheal tube 106 in this embodiment is equipped with a cuff 108 in the proximity to the distal end 106A of the endotracheal tube 106. The distal end 106A of the endotracheal tube 106 is then passed through the canal 98 and through the lumen 96 such that the distal end 106A of the endotracheal tube 106 protrudes from the lumen opening 93A on the upper oval surface 93 of the ellipsoid body 92, as shown in FIG. 7B. The endotracheal tube 106 can slide along the proximal-dorsal axis of the tubeless intubating device 90 such that a longer or shorter portion of the endotracheal tube 106 protrudes from the lumen opening 93A. The endotracheal tube cuff 108 can be inflated after it is loaded into the device 90 and secured in place with the ring holder 102.

As can be further appreciated from FIG. 7B, after the tubeless intubating device 90 delivers and assists in placing the endotracheal tube 106 in the patient under direct and continuous visualization, the tubeless intubating device 90 can be easily removed from the patient while the endotracheal tube 106 remains safely in place under continuous vision. Thus, the tubeless device 90 can be used with a standard endotracheal tube to intubate and extubate a patient. The device 90 can be also used as a supraglottic device.

Figure 7C:
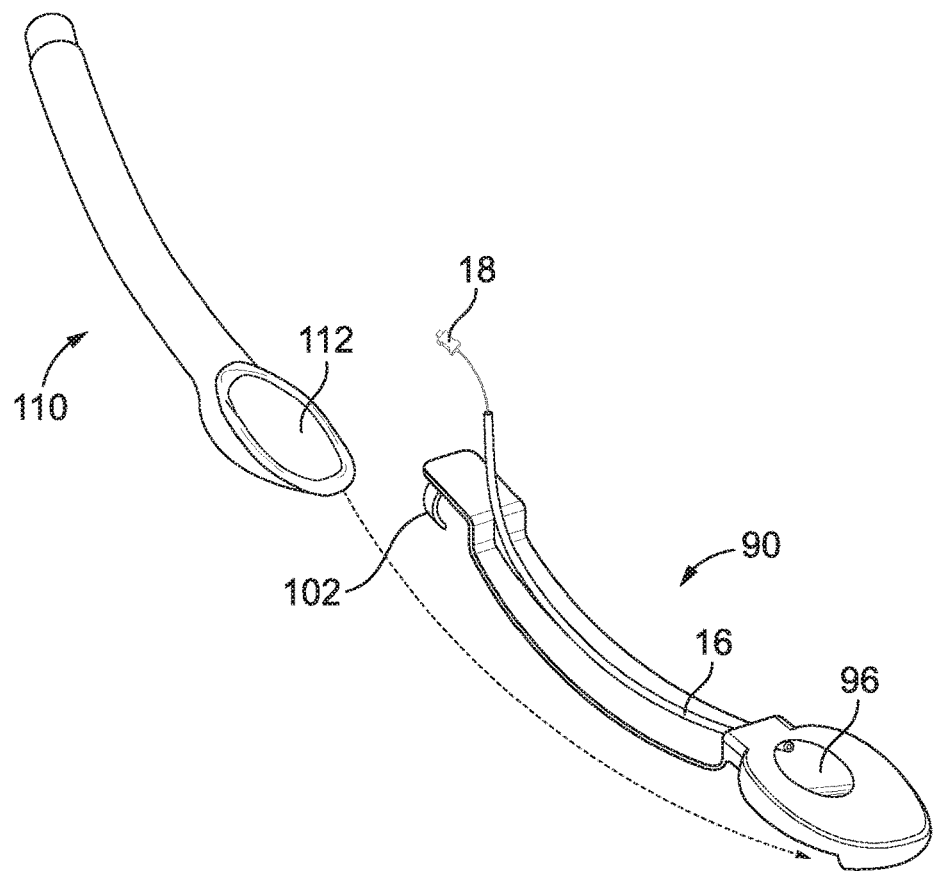
FIG. 7C depicts loading of a supraglottic airway onto the tubeless intubating device of FIG. 7A.
Figure 7D:
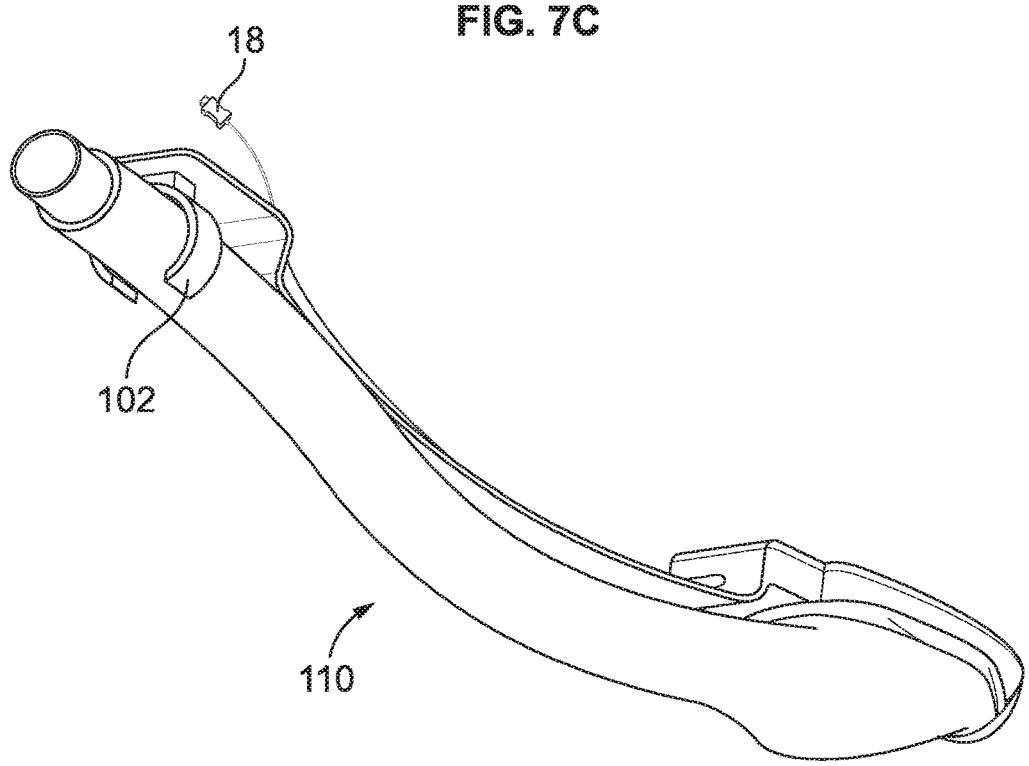
FIG. 7D depicts an assembly of the supraglottic device of FIG. 7C with the tubeless intubating device of FIG. 7A.

As shown in FIGS. 7C and 7D, the tubeless intubating device 90 can be used for intubation and extubation of a patient with a supraglottic airway, generally 110. The device 90 can also be used for placement of a laryngeal mask airway. As shown in FIG. 7D, the supraglottic airway 110 is secured in the device 90 with the ring holder 102 such that the distal end of the device 110 is aligned with the distal end of the device 90 and the lumen 96 of the device 90 is aligned with the lumen 112 of the device 110 and secured. Because the assembly of the devices 90 and 110 is equipped with the camera 16, it provides continuous visualization of patient's supraglottic structure during placement.

Figure 8:
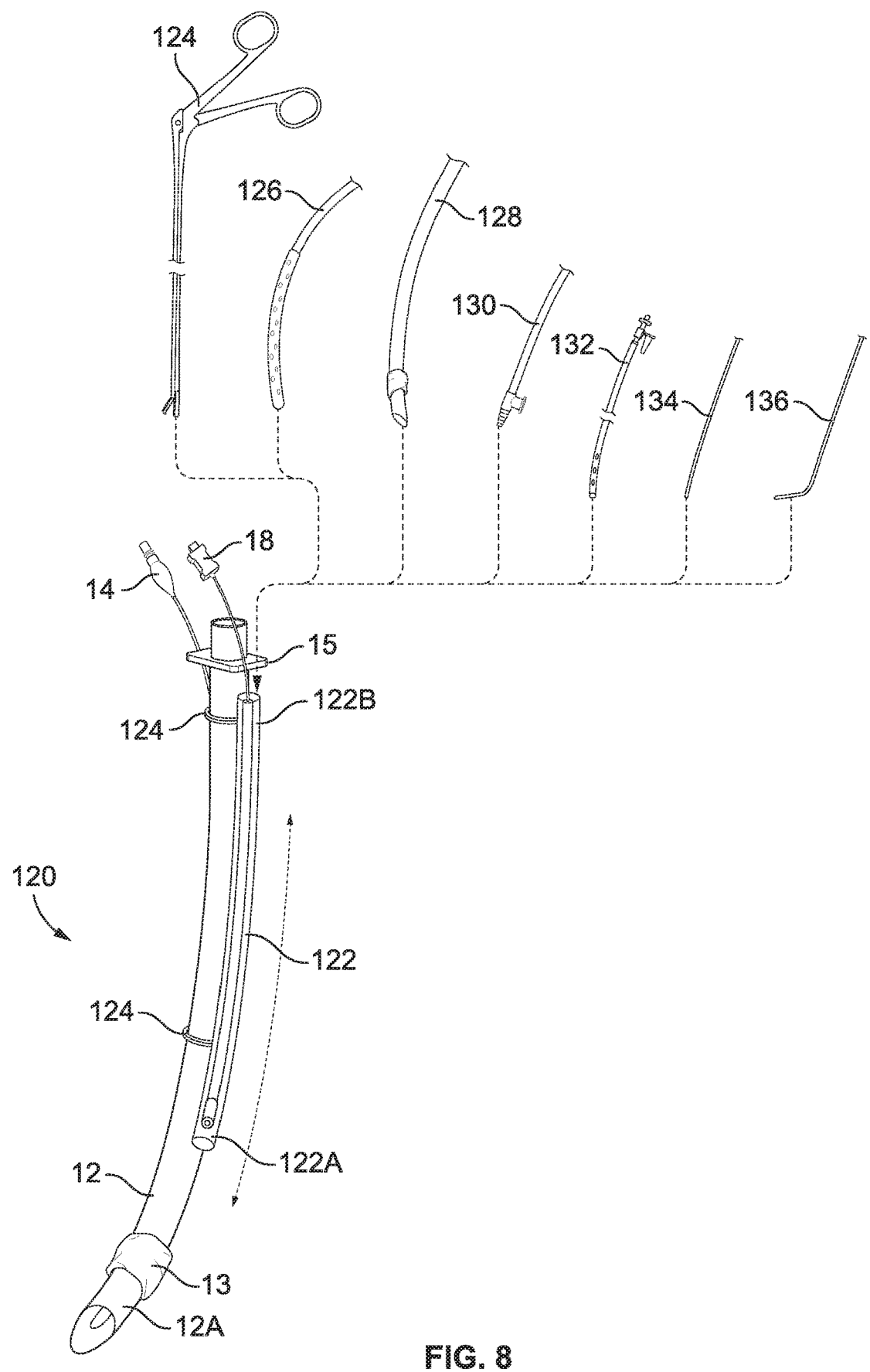
FIG. 8 depicts a tool tube and camera combined with an endotracheal tube by the means of rings.

FIG. 8 provides a further embodiment for an endotracheal device, generally 120. The device 120 comprises an endotracheal tube 12 combined with a tool tube 122. The tool tube 122 is combined with the endotracheal tube 12 externally and is held in place on the endotracheal tube 12 with rings 124. The rings 124 are attached to the tool tube 122. The rings 124 can slide long the endotracheal tube 12 and move the tool tube 122 on the endotracheal tube 12 closer or further away from a cuff 13 located in near proximity to the distal end 12A of the endotracheal tube 12. The tool tube 122 is hollow and a medical tool and/or camera 16 can be placed inside the tool tube 122 through its proximal end 122B. The camera 16 can slide inside the tool tube 122 and may protrude distally from the distal end 122A of the tool tube 122. The camera 16 can be removed from the tool tube 122 while the tool tube 122 is still in place in the patient. A tool, including but not limited to, biopsy forceps 124, esophageal stethoscope 126, cuff tube 128, suction tube 130, nasogastric tube 132, stylet 134 and/or bougie 136 can be inserted in the tool tube 122 through an opening at the proximal end 122B.

Each of the ring holders 124 is attached to the tool tube 122. The ring holder 124 can be a complete ring or a half-ring. It can be also equipped with a clasp. It is understood that the tool tube 122 can be attached with the ring holder 124 to any tubal medical device. The tool tube 122 can then slide on the tubal medical device or endotracheal tube 12 proximally or distally. The tool tube 122 can also rotate about the tubal medical device or endotracheal tube 12. In other embodiments, the tool tube 122 can be placed internally into an endotracheal tube or supraglottic airway lumen. It will be appreciated that in the FIG. 8, the tool tube 122 is equipped with two rings 124 attached to the tool tube 122. In further embodiments, the tool tube 122 can be equipped with only one ring or at least 3 rings. The positioning of the rings 124 on the tool tube 122 can vary. It will be further appreciated from FIG. 8, that the positioning of the tool tube 122 along the body of the endotracheal tube 124 can be adjusted such that the tool tube 122 can brought in near proximity with the cuff 13. A tool, such as the bougie 136 can protrude distally from the tool tube 122, including protruding distally from the distal end 12A of the endotracheal tube 12. The bougie 136 can then guide an insertion of the endotracheal tube 12 or any other tubal medical device to which the tool tube 122 is attached in the patient's body.

Figure 9A:
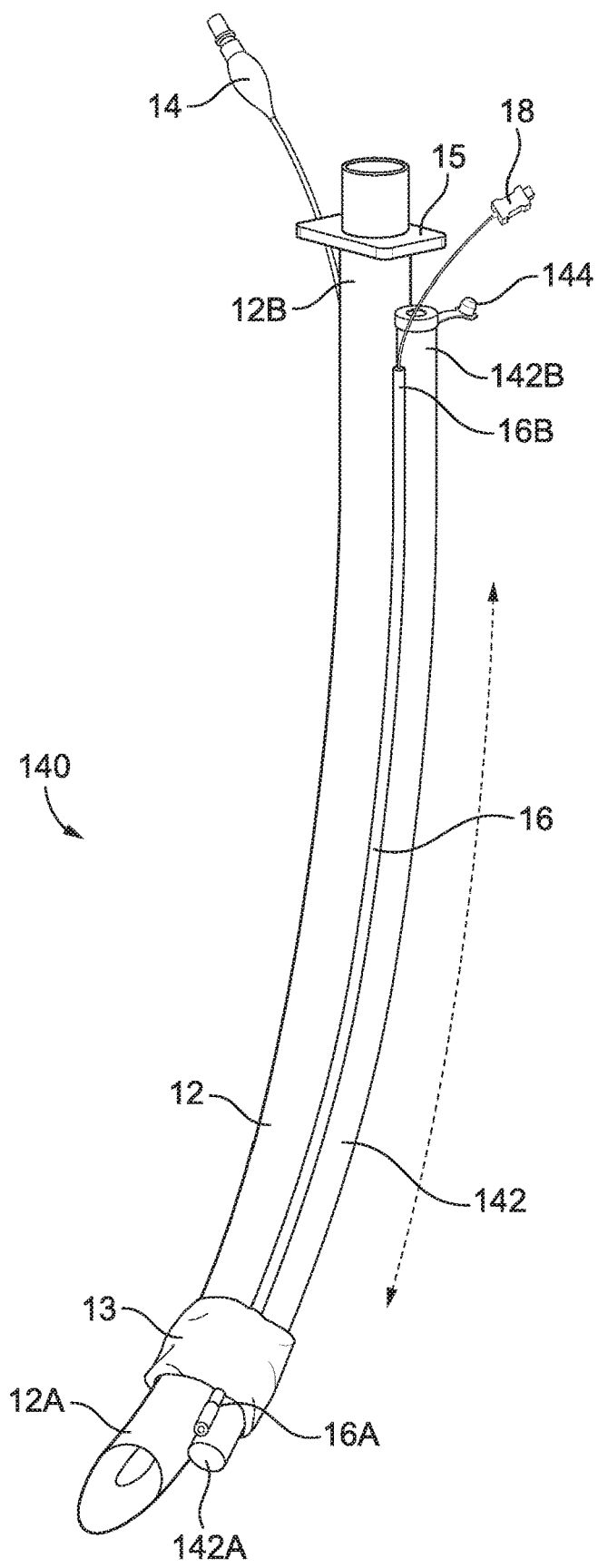
FIG. 9A depicts an assembly of a camera with a tool tube and further assembled with an endotracheal tube.

FIG. 9A provides another embodiment for an endotracheal device, generally 140. In this embodiment, an endotracheal tube 12 is combined with a camera 16 which is attached to a hollow tool tube 142 externally. The tool tube 142 has a distal end 142A and a proximal end 142B. The distal end 16A of the camera 16 is aligned with the distal end 142A of the tool tube 142. The proximal end 16B of the camera 16 is aligned with the proximal end 142B of the tool tube 142. As can be seen from the embodiment in FIG. 9A, the distal end 142A of the tool tube 142 protrudes distally from the distal end 16A of the camera 16. When a tool, such as any of the tools described in connection with FIG. 8, is placed inside the tool tube 142, the tool can protrude from the distal end 142A of the tool tube 142. The tool, such as for example bougie, can then be manipulated under continuous visualization by camera 16.

The endotracheal tube 12 is equipped with a cuff 13 and means 14 for inflating the cuff 13, as was discussed in detail in connection with FIG. 1A. The tool tube 142 is hollow and has an opening at the distal end 142A and an opening at the proximal end 142B. The tool tube 142 can be capped with a cap 144 at the proximal end 142B, if needed. The distal end 16A of the camera 16 is aligned right above the distal end 142A of the tool tube 142. The tool tube 142 is combined with the endotracheal tube 12 by being inserted under the cuff 13. Accordingly, the distal end 142A of the tool tube 142 can be distal to the cuff 13. This allows to insert tools and conduct needed procedures distally to the cuff 13 under the continuous visualization from the camera 16.

The tool tube 142 together with the camera 16 can slide along the proximal-distal (12B-12A) axis of the endotracheal tube 12. The tool tube 142 together with the attached camera 16 can be removed from the patient while the endotracheal tube 12 remains inserted.

Figure 9B:
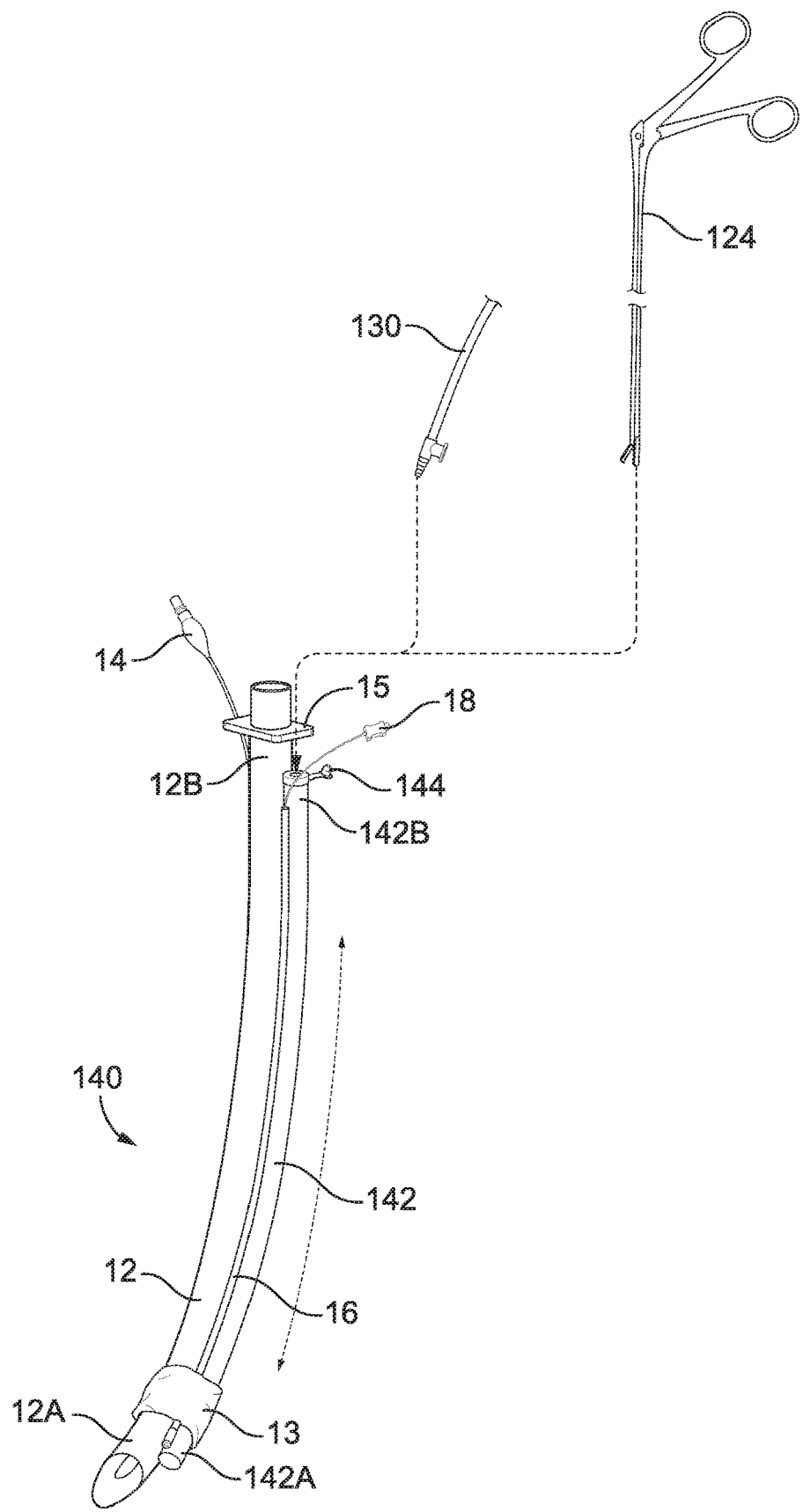
FIG. 9B depicts various medical devices to be inserted into the tool tube of the FIG. 9A.

FIG. 9B depicts various tools, including, but not limited to, biopsy forceps 124 or the suction tube 130, that can be inserted into the tool tube 142. The tool tube 142 can be also used for insertion a bougie (not shown). A bougie either alone or in combination with any other tools can be inserted into the tool tube 142. The bougie can be positioned distally to the distal end 12A of the endotracheal tube 12. The bougie can be then used for guiding placement in a patient of the endotracheal tube 12 under the continuous visualization of the camera 16.

When the tool tube 142 is not in use, the proximal opening of the tool tube 142 can be closed with the cap 144. This allows to establish a closed system for ventilation through the endotracheal tube 12 while the tool tube 142 still inserted in the patient.

Figure 10A:
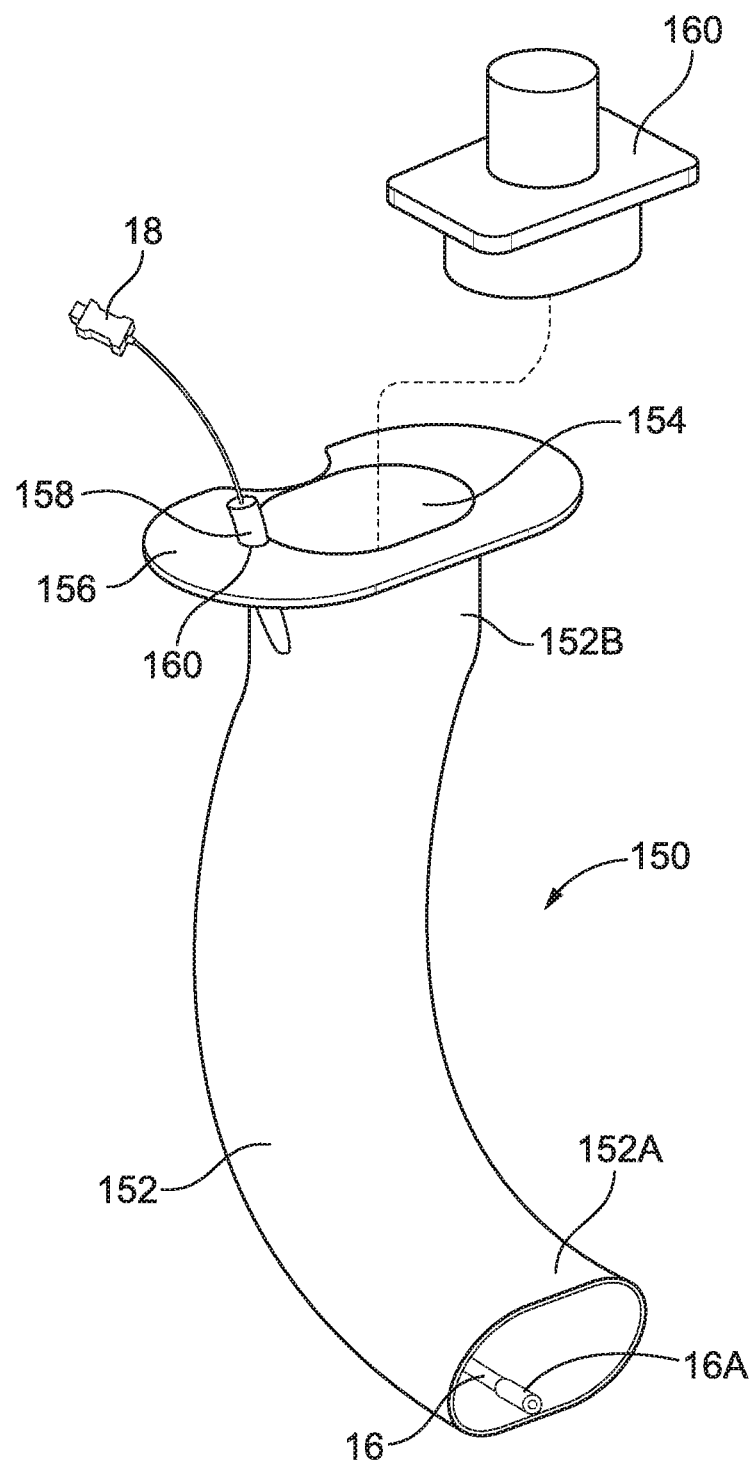
FIG. 10A depicts an oral airway device equipped with a camera inserted through a channel.

FIGS. 10A-10F are further embodiments of an oral airway device, generally 150. As shown in FIG. 10A, the device 150 comprises a hollow tubal body 152 with a lumen 154 into which the endotracheal tube 12 or any other medical device can be inserted.

The tubal body 152 has a proximal end 152B and a distal end 152A. The tubal body 152 ends with a plate 156 at the proximal end 152B. The plate 156 is perpendicular to the tubal body 152 and keeps the device 150 in place from sliding into the patient's body. The tubal body 152 is slightly curved to follow the curvature of the patient's tongue. In the embodiment of FIG. 10A, a camera 16 is combined with the tubal body 152 by being inserted through a channel 158. The channel 158 opens on the proximal side of the plate 156 and then goes through an opening 160 in the plate 156. The channel 158 then continues through the wall of the tubal body 152 and opens inside the lumen 154. The camera 16 is inserted through the channel 158 into the lumen 154. In other embodiments, the opening 160 does not connect to a channel, instead the camera is inserted directly through the opening 160 and then through an opening in the wall of the tubal body 152 in the lumen 154.

The camera 16 is inserted into the tubal body 152 through the channel 158 or in other embodiments, the camera 16 is inserted directly through the wall of the tubal body 152 without the channel. The distal end 16A of camera 16 can be aligned with the distal end 152A of the tubal body 152. The camera 16 can slide up and down along the tubal body 152. The camera 16 can be removed from the tubal body 152, while the tubal body 152 remains inserted in the patient.

In the embodiment of FIG. 10A, the camera 16 is equipped with a wire 18. In other embodiments, the camera 16 can be wireless. The opening 154 of the tubal body 152 can be closed with a ventilation cap 160 at the proximal end 152B. This allows ventilation while the camera 16 is in place and continued visualization and monitoring of the patient.

Figure 10B:
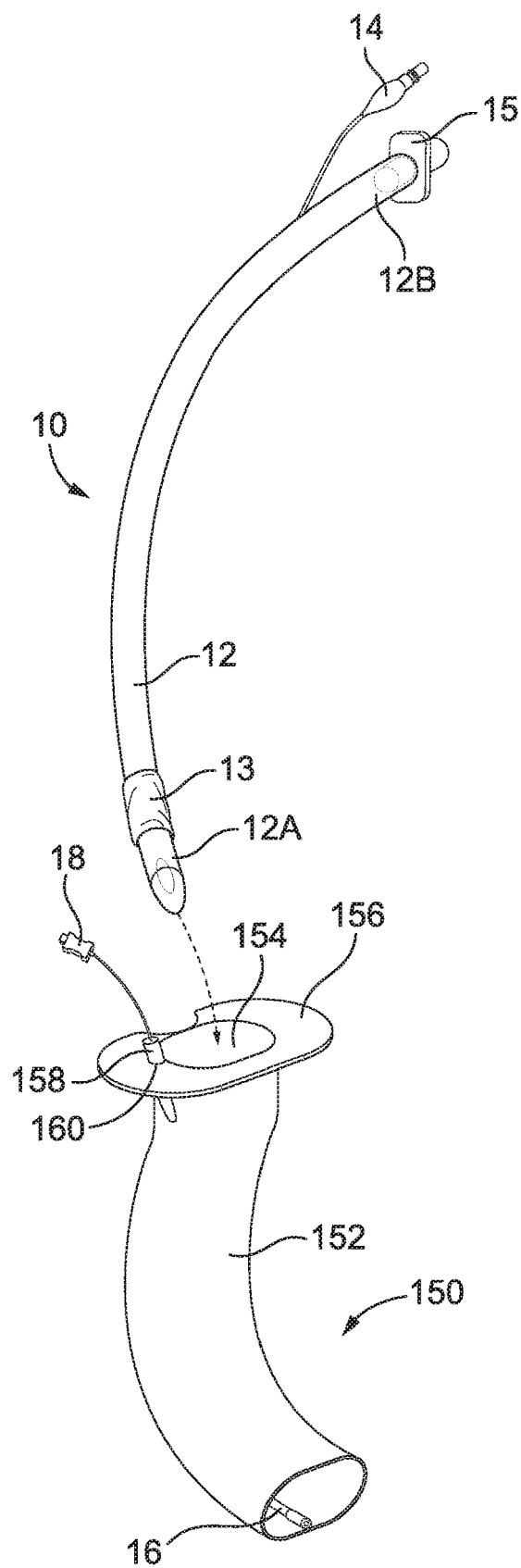
FIG. 10B depicts inserting an endotracheal tube into the oral airway device of FIG. 10A.
Figure 10C:
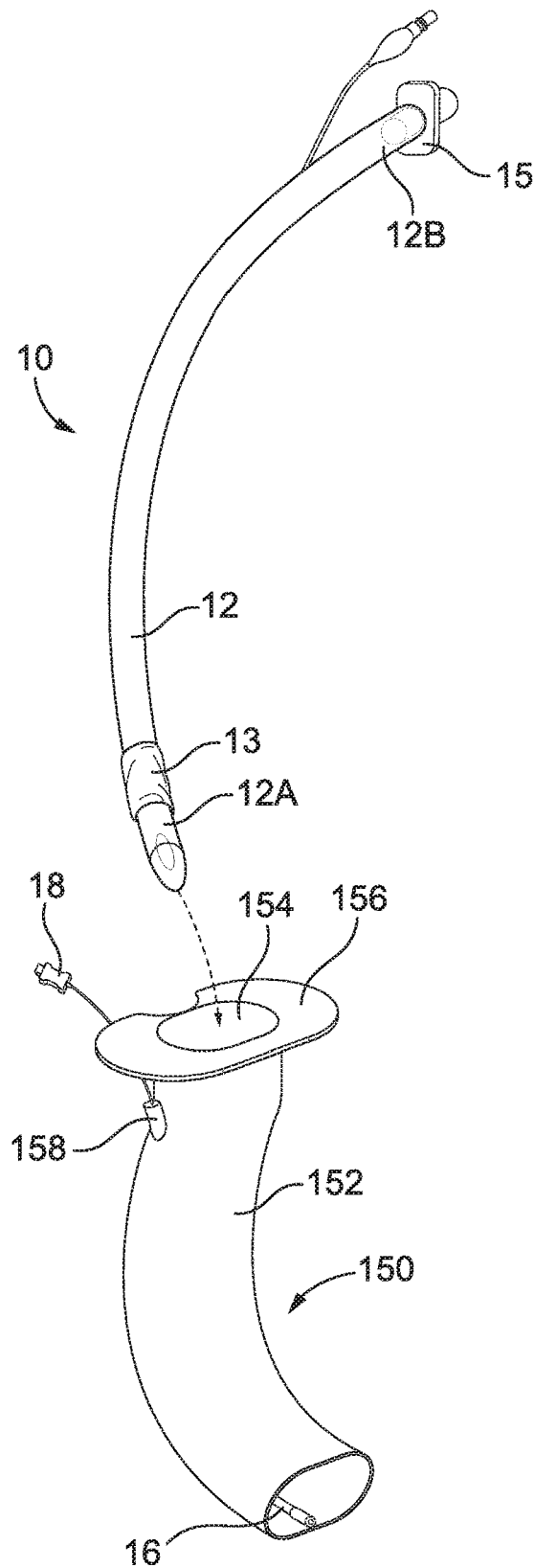
FIG. 10C depicts a further embodiment with an alternative positioning of the channel on the oral airway device body.

As shown in FIGS. 10B and 10C, the oral airway device 150 can be used for inserting an endotracheal tube 10 into a patient. In the embodiment of FIG. 10B, the channel 158 enters the tubal body 152 through the opening 160 as was discussed in connection with the embodiment of FIG. 10A. In the embodiment of FIG. 10C, the channel 158 enters the tubal body 152 distally to the plate 156. Thus, the plate 156 in the embodiment of FIG. 10C does not comprise an opening for the channel 158.

Figure 10D:
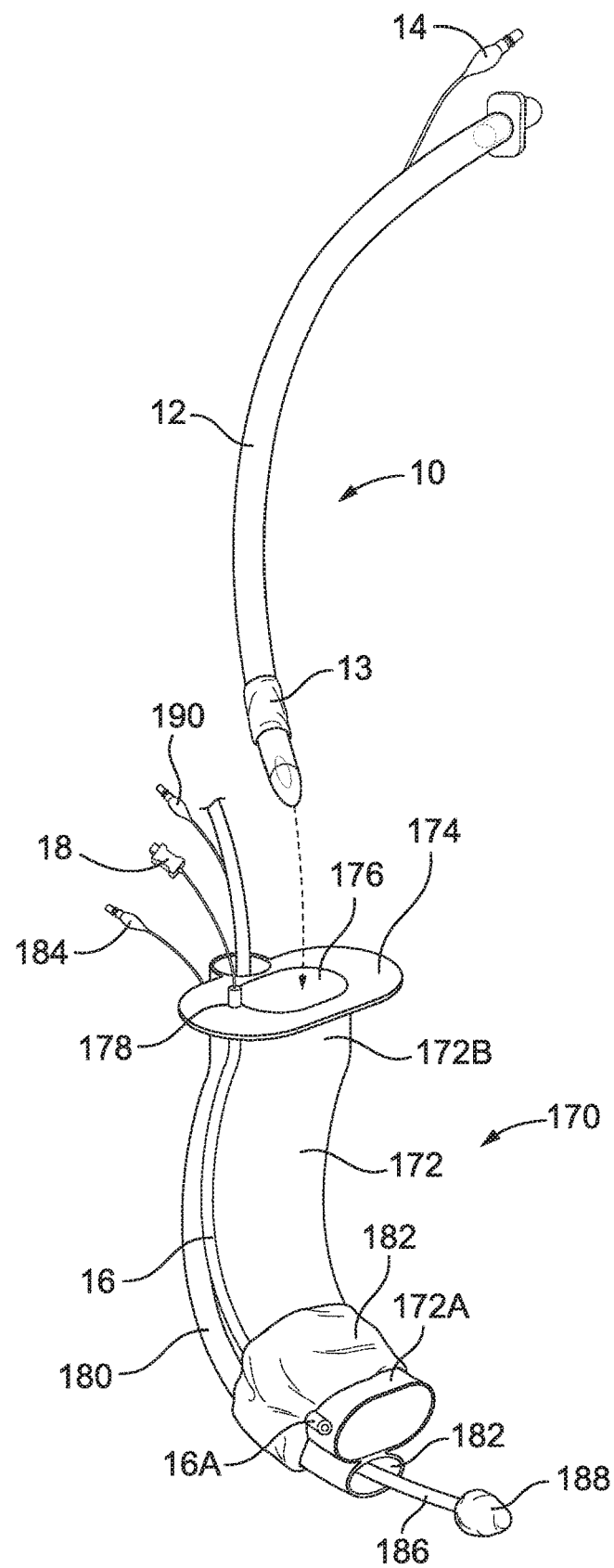
FIG. 10D is a further embodiment of an oral airway device comprising two balloons and a camera.

FIG. 10D is a further embodiment of an oral airway device, generally 170. The device 170 comprises a hollow curved tubal body 172. The curve of the tubal body 172 matches the curve of a patient's tongue for secure placement. The tubal body 172 has a distal end 172A and a proximal end 172B. The tubal body 172 ends with a plate 174 at the proximal end 172B. The plate 174 is perpendicular to the tubal body 172. The tubal body 172 is hollow and it comprises a central lumen 176 through which the endotracheal tube 10 or any other device can be inserted into a patient. A camera 16 is inserted through an opening 178 in the plate 174 and is aligned along the proximal-distal axis (172B-172A) of the tubal body 172 such that the distal end 16A of the camera 16 can be aligned with the distal end 172A of the tubal body 172. The camera 16 can comprise wire 18 or the camera 16 can be wireless.

The device 170 further comprises a second hollow tubal body 180 which is aligned with the tubal body 172. A balloon 182 wraps around the tubal body 172 and the tubal body 180 in a near proximity to the distal end 172A. Thus, the two tubal bodies, 172 and 180, are held together by the balloon 182. The distal end 16A of the camera 16 is inserted under the balloon 182. Accordingly, the camera 16 can take images distally to the balloon 182. The camera 16 can be removed from the patient, while the device 170 remains in place in the patient. The balloon 182 can be inflated with a means 184.

The second tubal body 180 comprises a lumen 182. The tubal body 180 is attached along the proximal-distal axis of the tubal body 172. This additional tubal body 180 can be used for positioning an esophageal blocker 186 which can be then placed in the patient's esophagus under direct visualization with the camera 16. The esophageal blocker 186 is equipped with a balloon 188 at the distal end. The balloon 188 can be inflated with a means 190 and seal the patient's upper esophagus. In addition, the device 170 is equipped with a second balloon 182 which is circumferential and wraps around the bodies 172 and 180, and located proximally to the balloon 188. The balloon 182 can be used to inflate with the means 184. The balloon 182 used for sealing the upper pharynx. Thus, the device 170 may act as a supraglottic airway with the endotracheal tube 10 pulled back proximally in the device 170 with the endotracheal tube 12 inflated.

Figures 10E, 10F:
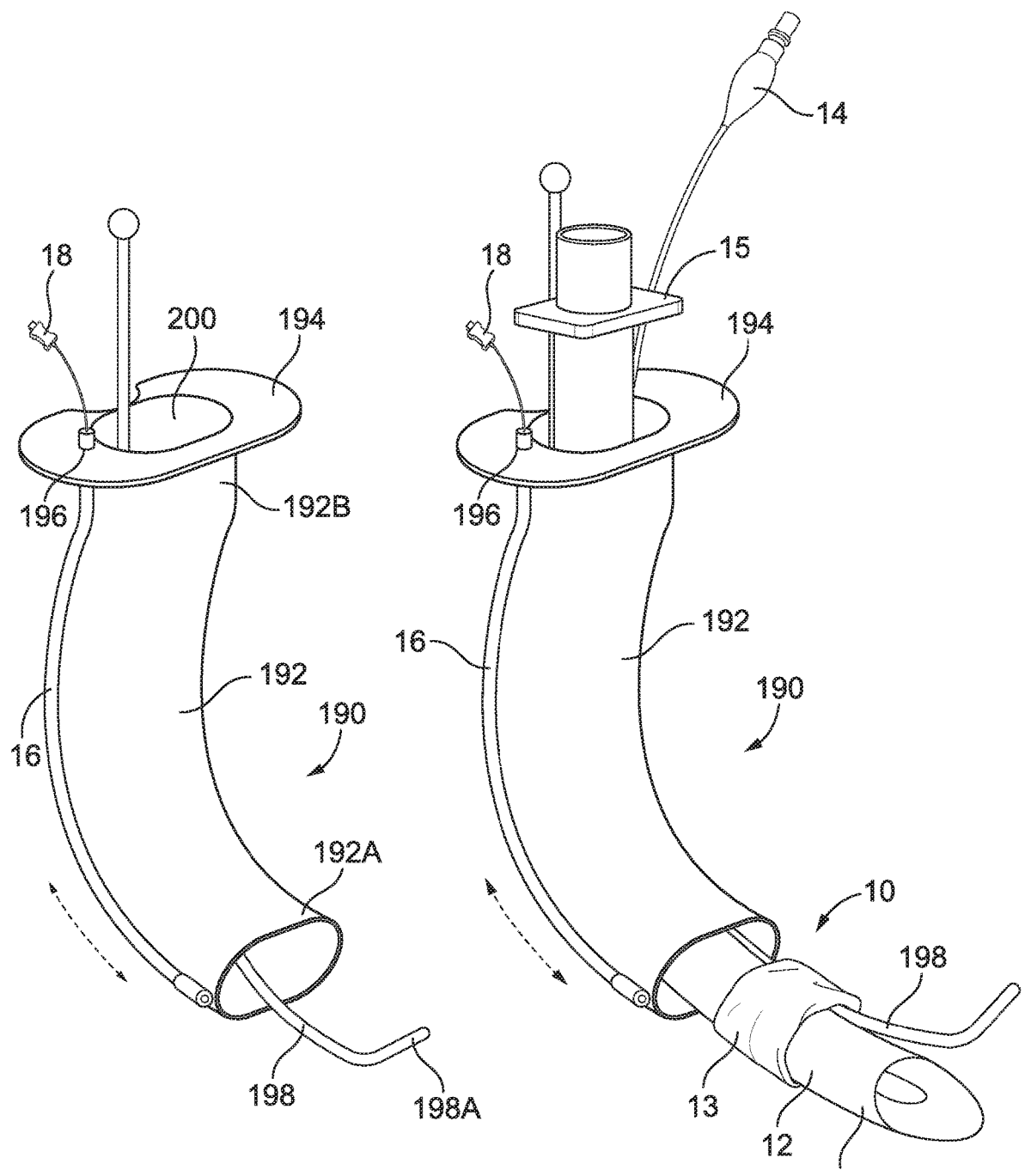
FIG. 10E depicts an oral airway device combined with a bougie.
FIG. 10F depicts the oral airway device of FIG. 10E assembled with an endotracheal tube.

FIG. 10E provides a further embodiment of an oral airway device, generally 190. The device 190 comprises a curved tubal hollow body 192 with a distal end 192A and a proximal end 192B. The tubal body 192 ends with a plate 194 at the proximal end 192B. The plate 194 is perpendicular to the tubal body 192. A camera 16 is inserted through an opening 196 in the plate 194. The camera 16 then runs along the proximal-distal axis (192B-192A) of the tubal body 192 such that a distal end 16A of the camera tube 16 can be aligned with the distal end 192A of the tubal body 192.

A bougie 198 or any other tool can be inserted into a central lumen 200 of the tubal body 192. The distal end 198A of the bougie 198 can protrude from the lumen 200 distally. The patient's tissues can be manipulated with the bougie 198 under the continuous visualization by the camera 16. As the camera 16 can slide along the tubal body 192, images can be taken at different locations with respect to the distal end 192A of the tubal body 192. The camera 16 can be easily removed from the patient, while the tubal body 192 remains in place.

In the embodiment of FIG. 10F, the oral airway device 190 of FIG. 10E is assembled with the endotracheal tube 10. In this embodiment, the bougie 198 is inserted under the cuff 13 of the endotracheal tube 12. This allows for an insertion of the endotracheal tube 10 under the continued visualization from the camera 16. The insertion can be guided with the bougie 198. After the insertion has been completed, the bougie 198, the camera 16 and/or the tubal body 192 can be removed, while the endotracheal tube 12 still remains inserted in the patient as needed.

Figure 11A:
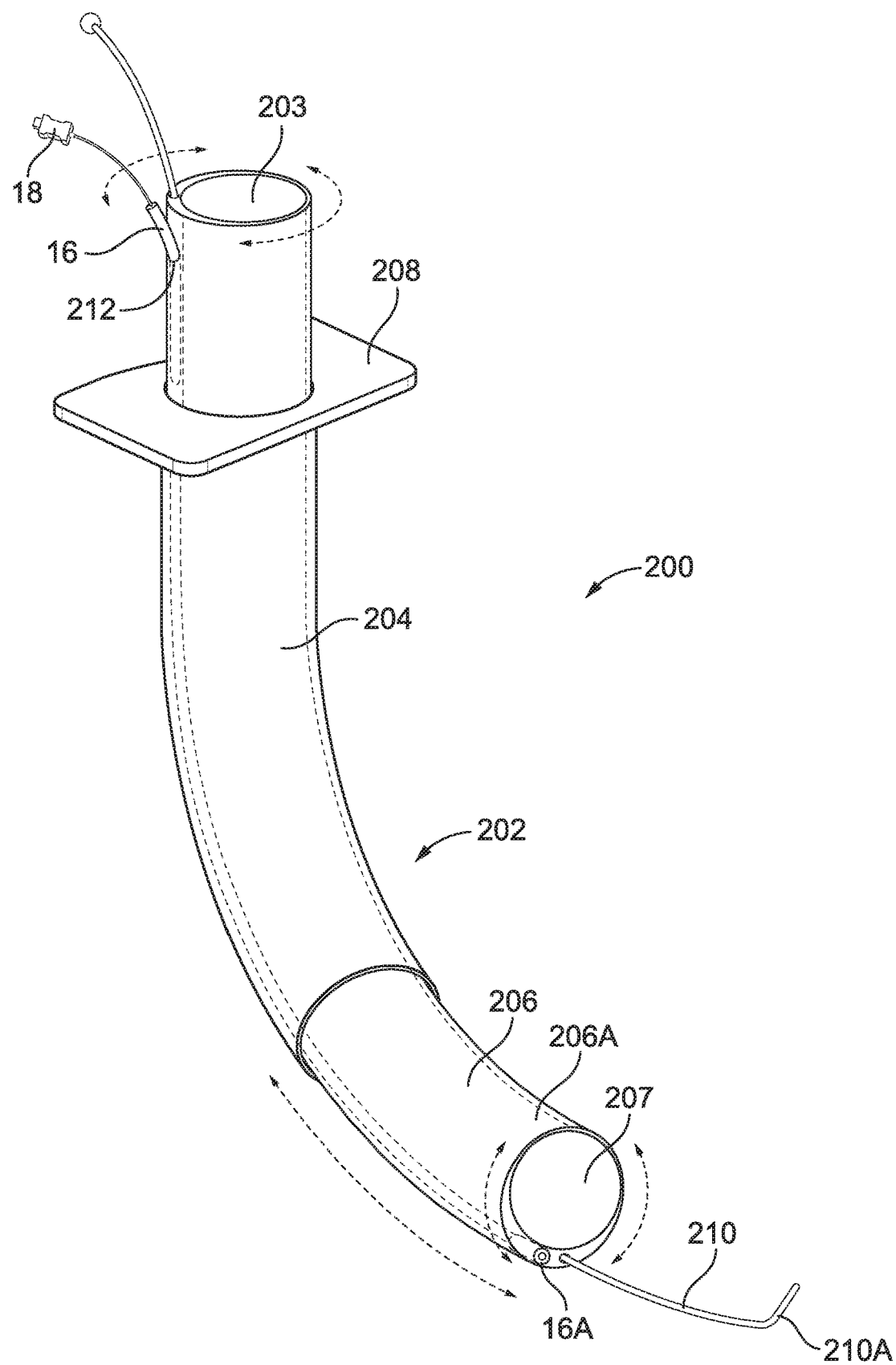
FIG. 11A depicts an oral airway device of adjustable length.

FIG. 11A depicts a further embodiment of an oral airway device with adjustable length for ventilation, continual visualization, and intubation, generally 200. The device 200 comprises a two-part tubal body 202 with a lumen 203 and with open proximal and distal ends. The length of the two-part tubal body 202 can be adjusted because the two-part tubal body 202 is made from an outer cylindrical tube wall 204 and an inner cylindrical tube 206, wherein the inner cylindrical tube 206 is at least partially inserted into the outer cylindrical tube 204. The inner cylindrical tube 206 can be extended from the outer cylindrical tube 204, thus increasing the length of the two-part tubal body 202, as needed.

The inner cylindrical tube 206 can be also retracted back inside of the outer cylindrical tube 204, thus decreasing the length of the two-part tubal body 202, as needed. The diameter of the outer cylindrical tube 204 is larger than the diameter of the inner cylindrical tube 206. Thus, the lumen 203 of the outer cylindrical tube 204 has a diameter larger than the lumen 207 of the inner cylindrical tube 206.

The inner cylindrical tube 206 is at least partially inserted inside of the larger outer cylindrical tube 204. The inner cylindrical tube 206 can rotate around inside the outer cylindrical tube 204. The inner cylindrical tube 206 can also move distally and it can be extended distally from the outer cylindrical tube 204, thus the length of the tubal body 202 can be elongated or shorten, as may be needed. In some embodiments, the cylindrical tube 206 can be completely separated and removed from the cylindrical tube 204. The tube 204 comprises a plate 208 near its proximal end. The plate 208 is perpendicular to the cylindrical tube 204. After the insertion into a patient, the plate 208 prevents sliding of the device 200 into the patient's oral cavity.

At least one of or both cylindrical tubes 204 and 206 are curved to fit the curvature of the patient's tongue and prevent the tongue from rolling back and obstructing the patient's airways. In alternative embodiments, the cylindrical tubes 204 and 206 are not curved, but they can be made of a plastic or some other flexible material which permits bending the tubal body 202 as may be needed.

The device 200 may comprise a bougie 210 which may be inserted into the lumen 203 such that the distal end 210A of the bougie 210 can protrude from the lumen 207. In some embodiments, the lumen 203 is a complete lumen fully separated from the central lumen 203. In other embodiments, the lumen 203 is a semi-lumen which opens into the central lumen 203.

The bougie 210 can be inserted and removed from the tubal body 202 at any time even as the tubal body 202 remains inserted in the patient. In further embodiment, at least one of the cylindrical tubes 204 or 206 can be removed from the patient's oral cavity, while the other cylindrical tube remains inserted in the patient. In some embodiments, the cylindrical tube 206 is removed. In other embodiments, the cylindrical tube 204 is removed.

The device 200 comprises a camera 16 which may further comprise a wire 18. The camera 16 is inserted inside of the cylindrical tube 204 through an opening 212 located in proximity to the proximal end of the cylindrical tube 204. The opening 212 is located proximally to the plate 208. The distal end 16A of the camera 16 can be aligned with a distal end 206A of the cylindrical tube 206 and in near proximity to the distal end 210A of the bougie 210. Accordingly, the bougie 210 can be operated under the continuous visualization from the camera 16.

Figure 11B:
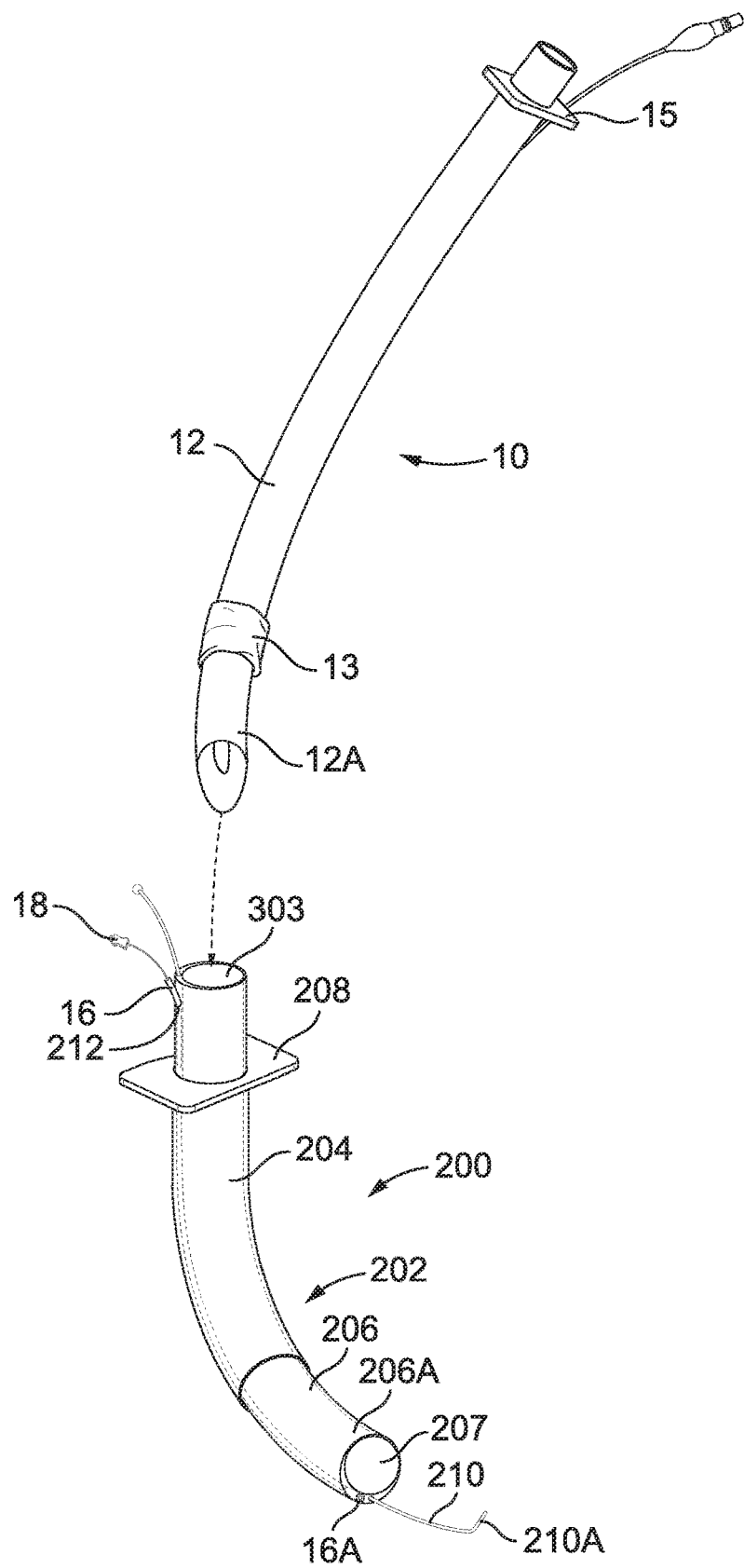
FIG. 11B depicts the device of FIG. 11A assembled with an endotracheal tube.

FIG. 11B depicts an embodiment in which the device 200 is further assembled with the endotracheal tube 10 described in embodiment of FIG. 1A. It will be appreciated by a person of skill, that any other endotracheal tube can be also used.

Figure 11C:
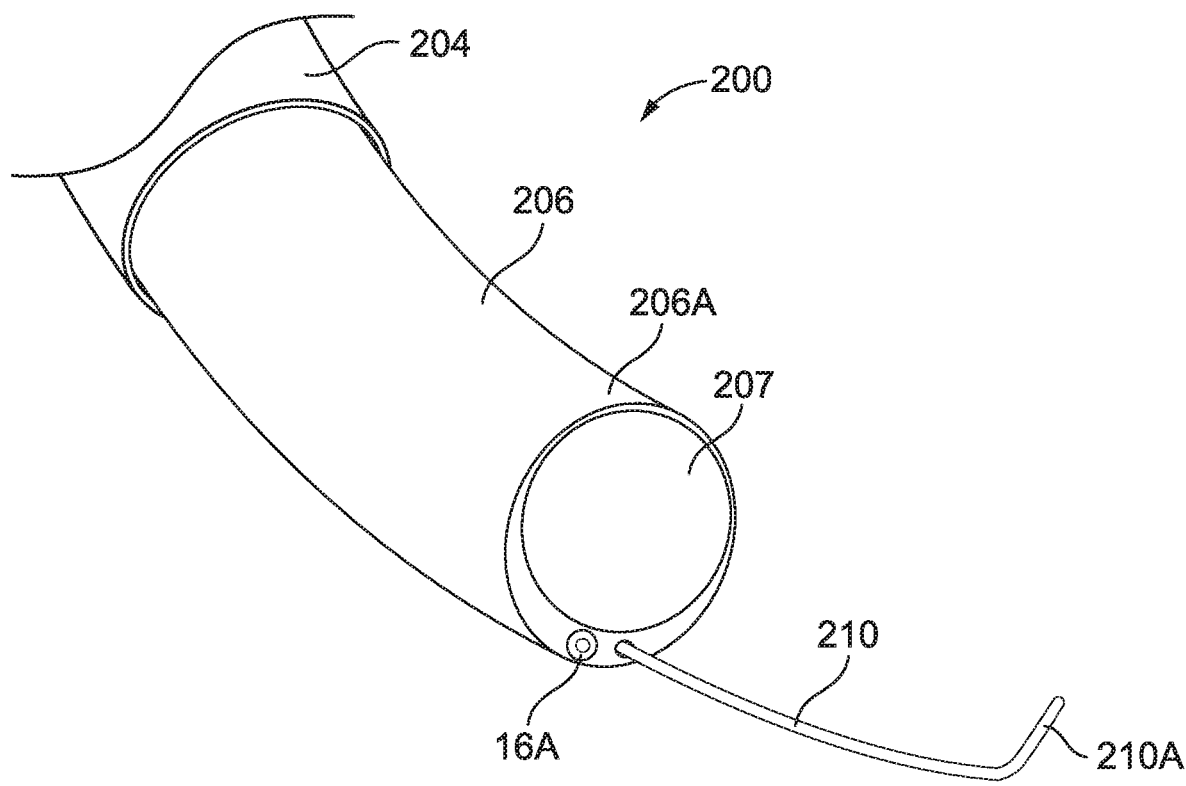
FIG. 11C is an enlarged view of the distal portion of the device of FIG. 11A with a camera immobilized in the oral airway tube.
Figure 11D:
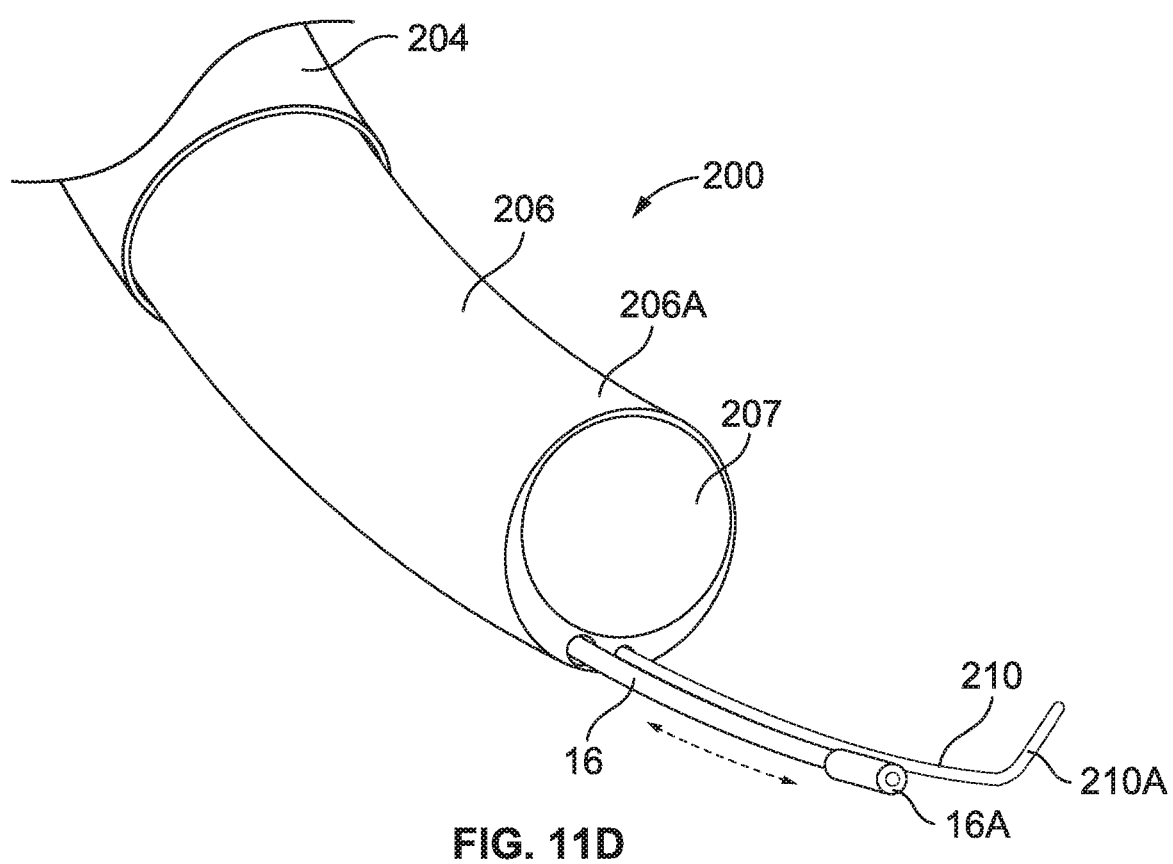
FIG. 11D is an enlarged view of the distal portion of the device of FIG. 11A with a camera being mobile and able to slide in and out from the oral airway tube.

FIGS. 11C and 11D are an enlarged view of a distal portion of the device 200 from FIG. 11A. In the embodiment of FIG. 11C, the camera 16 is inserted into a wall of the cylindrical tube 206 and the distal end 16A of the camera 16 remains at the distal end 206A of the cylindrical tube 206.

Figure 11E:
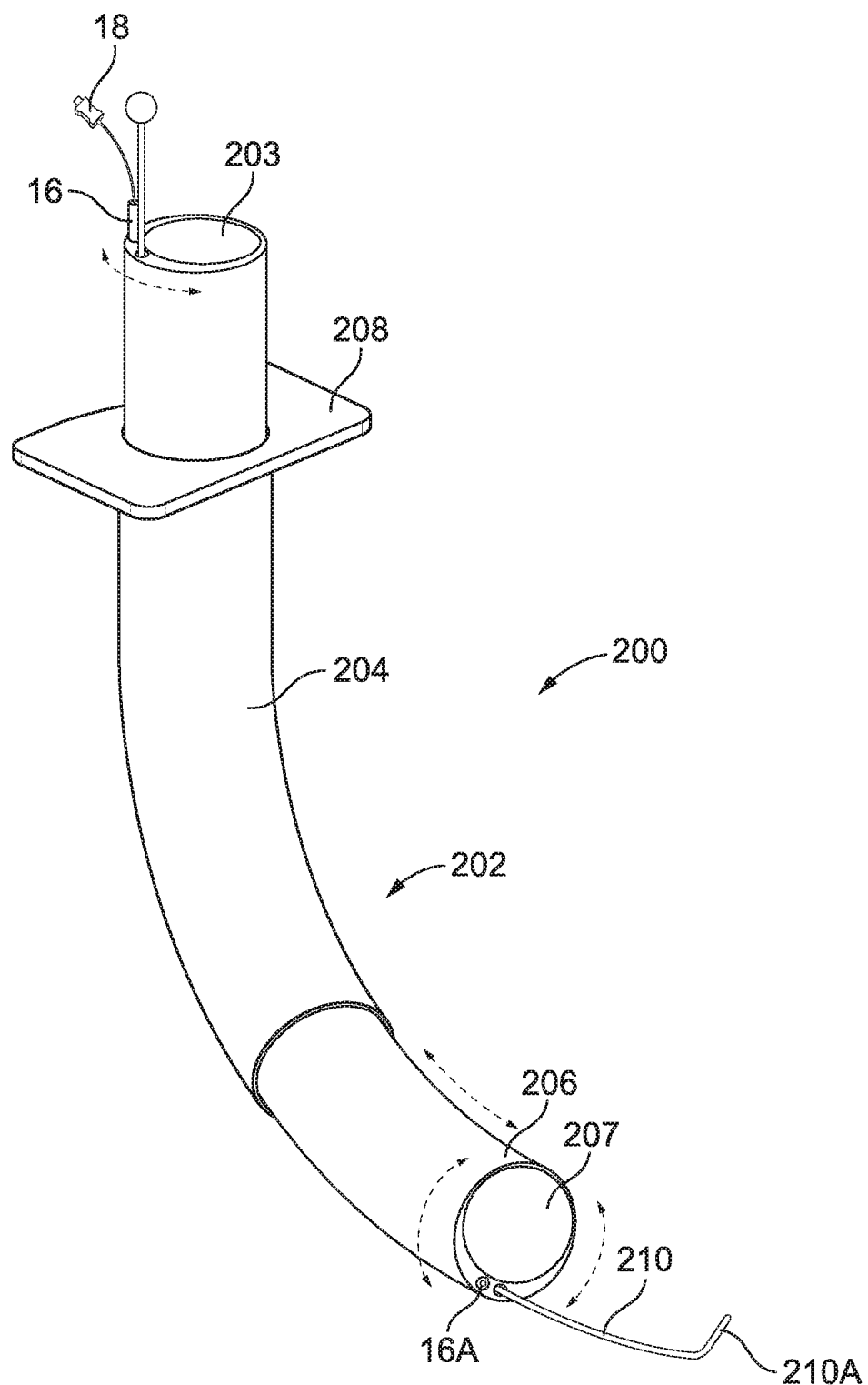
FIG. 11E is another embodiment of an oral airway device of adjustable length.

In the embodiment of FIG. 11D, the camera 16 can slide distally from the distal end 206A of the cylindrical tube 206. In this embodiment, the camera 16 can protrude outside the distal end 206A. The camera 16 can be retracted back into the wall of cylindrical tube 206. FIG. 11E provides a further embodiment of the device 200. In this embodiment, there is no separate opening for the camera 16 on the side of the cylindrical tube 204. Instead, the camera 16 is integrated in the wall of the cylindrical tube 206.

FIGS. 12A and 12B provide a further embodiment of a device, generally 220. The device 220 comprises a camera 16 combined with a stylet 222 which provides a backbone and shape to the otherwise flexible camera 16. As can be seen in the embodiment of FIG. 12B, the stylet 222 can be curved. The camera 16 can comprise a wire 18. The camera 16 is further combined with a hollow tube 224. Various tools, such as for example a bougie 226 can be inserted through the tube 224. Because the tube 224 has an open distal end 224A, the bougie 226 can protrude from the tool tube 224 distally to the distal end 16A of the camera 16. Accordingly, the bougie 226 can be manipulated under the continuous visualization of the camera 16. The device 220 can be used in combination with any other medical devices. The device 220 can be used for guiding a placement of a medical device, such for example an endotracheal tube. The placement of this medical device can be guided by the bougie 226 which can be used to move tissues away from the medical device passage under the continuous visualization from the camera 16. The stylet 22 can be made from a material (such as plastic for example) which can be bent into a particular shape as needed.

Figure 13:
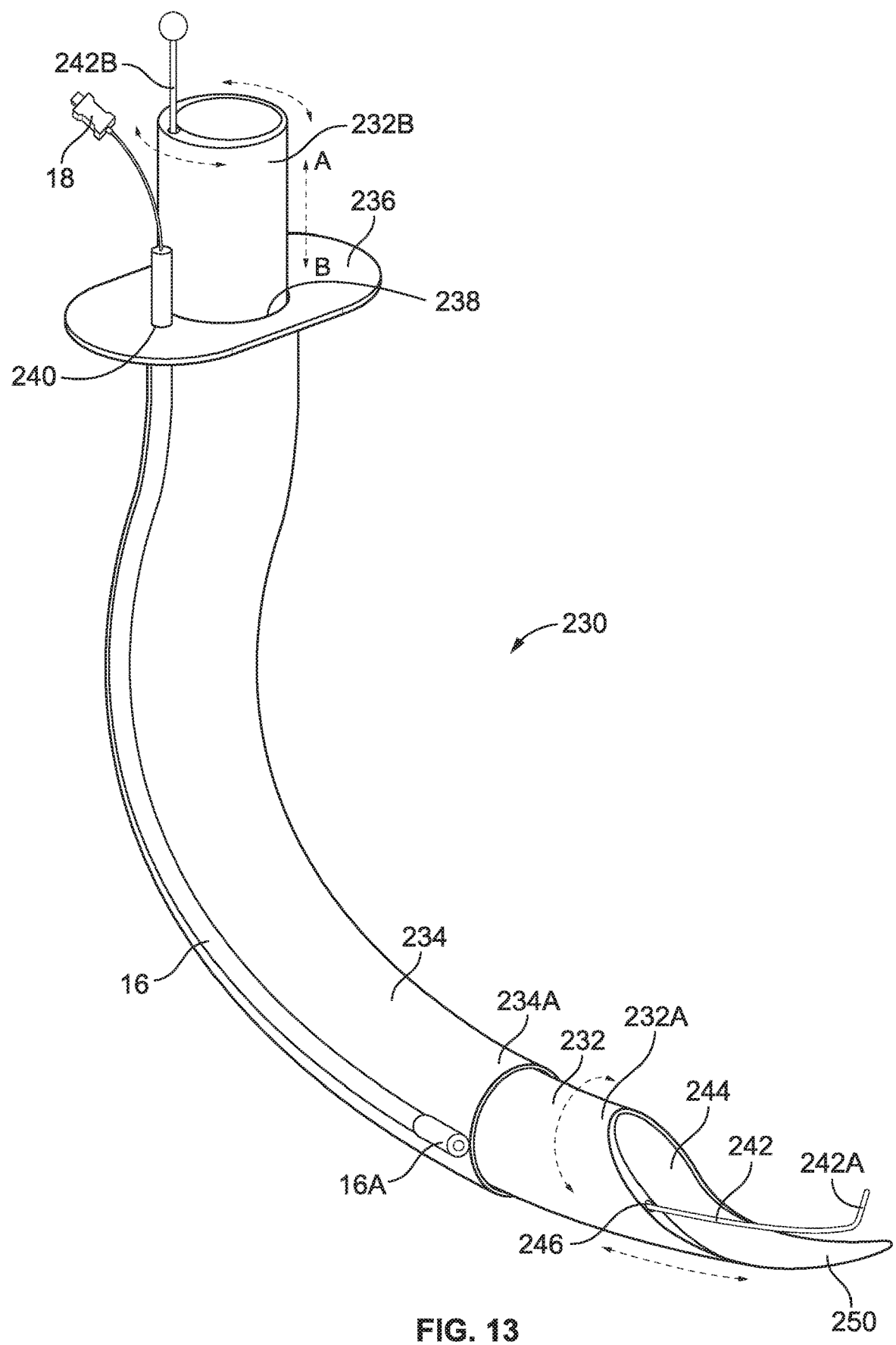
FIG. 13 depicts an oral airway device comprising two tubes with a bougie and a camera.

FIG. 13 provides a further embodiment for an oral airway device, generally 230. It comprises two hollow tubes. A first hollow tube 232 is inserted inside of a second hollow tube 234. The assembly of the two hollow tubes 232 and 234 is flexible such that the first hollow tube 232 can rotate around inside the second hollow tube 234. The second hollow tube 234 can also rotate around the first hollow tube 232.

At least the second hollow tube 234 or both hollow tubes 232 and 234 are curved such that the oral airway device 230 follows the contour of the roof of a patient's mouth. After it is inserted into a patient, the oral airway device 230 curves over and rests on top of the patient's tongue and therefore, it prevents the patient's tongue from obstructing the patient's airway.

The first hollow tube 232 is longer in length than the second hollow tube 234. The first hollow tube 232 can slide along the proximal-distal axis A-B in and out from the second hollow tube 234. A distal end 232A of the first hollow tube 232 can extend outside the second hollow tube 234 and retract back inside the second hollow tube 234. Thus, the length of the device 230 can be increased or decreased, and otherwise can be adjusted as needed. This adjustable size of the oral airway 230 provides a significant technical advantage and can avoid complications such as a failure to hold the tongue in place if an oral airway is too short or unintentionally pressing the tongue back into the airway if an oral airway is too long.

After the placement in the patient is completed, the first hollow tube 232 can be removed from the patient, while the second hollow tube 234 remains in place. In alternative, the second hollow tube 234 may remain in the patient, while the first hollow tube 232 is removed from the patient. This allows for easy cleaning and replacement of either of the two tubes 232 and 234 if needed.

A camera 16 is attached to the second hollow tube 234 externally in the embodiment of FIG. 13. A distal end 16A of the camera 16 is in near proximity with the distal end 234A of the second hollow tube 234. The second hollow tube 234 ends with a plate 236. The plate 236 has an oval shape with no sharp edges. The purpose of the plate 236 is to stay around the patient's lips while the hollow tubal body 234 is inserted in the patient. Thus, the plate 236 keeps the device 230 from sliding into the patient's pharynx after the device 230 has been placed. The plate 236 has two openings, 238 and 240.

The opening 238 is positioned in the center of the plate 236 and is used for insertion of the first hollow tube 232 into the second hollow tube 234. The first hollow tube 232 is inserted into the second hollow tube 234 through the opening 238 such that the proximal end 232B is proximal to the plate 236. The proximal end 232B remains outside the patient's body.

The opening 240 is positioned on the plate 236 such that the distal end 16A of the camera 16 is inserted through the opening 240. The distal end 16A of the camera 16 is then aligned with the distal end 234A of the second hollow tube 234.

The first hollow tube 232 may be used in combination with a bougie 242. The first hollow tube 232 comprises a central lumen 244. The wall of the first hollow tube 232 may comprise an additional tool lumen 246 for insertion of the bougie 242 or other tools. It will be readily appreciated that the tool lumen 246 can be a full lumen completely separated from the central lumen 244 in some embodiments. In other embodiments, the tool lumen 246 can be a semi-lumen connected to the central lumen 244. At least in some other embodiments, the tube 232 does not comprise the tool lumen 246, and tools are inserted into the central lumen 244 instead.

A distal end 242A of the bougie 242 protrudes from the distal end 232A of the first hollow tube 232. A proximal end 242B of the bougie 242 protrudes proximally to the oral airway device 230 and will remain outside the patient's body for easy manipulation.

In the embodiment of FIG. 13, the first hollow tube 232 ends with a tapered tongue 250 at the distal end 232A. The first hollow tube 232 can rotate inside the second hollow tube 234, such that the distal end 242A of the bougie 242 comes under a direct view of the camera 16. The bougie 242 is positioned above the tapered tongue 250 of the first hollow tube 232.

The first hollow tube 232 and the second hollow tube 234 can move independently of each other, including rotating in relation to each other.

Figure 14A:
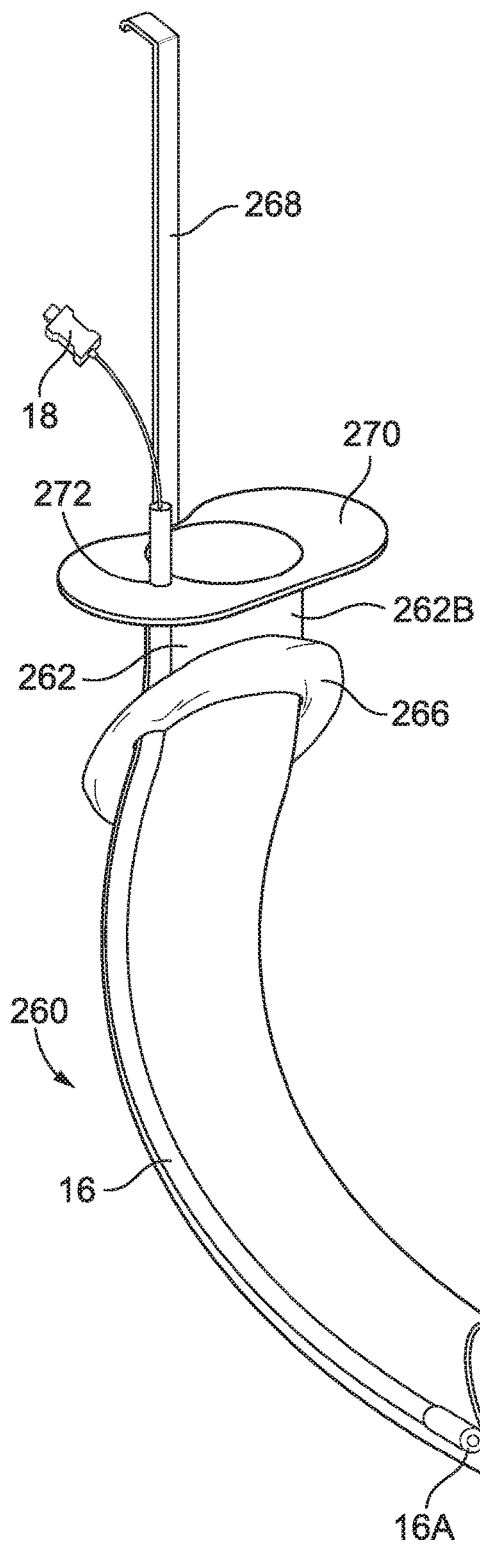
FIG. 14A depicts an oral airway device with a cuff operated by a handle.

Referring to FIG. 14A, provided is an oral airway device, generally 260, which comprises a curved tubal body 262 with a central lumen 264 which can be used for insertion of various devices such as for example, and endotracheal tube (not shown). Thus, the curved tubal body 262 is hollow. The device 260 can be used for preventing the tongue from covering the epiglottis. Thus, the device 260 can be used for opening and maintaining the patient's airway open. The curved tubal body 262 is curved in the way which conforms the curved tubal body 262 to the shape of the roof of the patient's mouth. The curved tubal body 262 will rest over the patient's tongue and prevent the tongue from obstructing the patient's airway.

A cuff 266 wraps around the curved tubal body 262 in FIG. 14A. A handle 268 is attached to the cuff 266. A camera 16 with a wire 18 runs along the curved tubal body 262 externally. The distal end 16A of the camera 16 is aligned with the distal end 262A of the curved tubal body 262. At the proximal end 262B, the curved tubal body 262 ends with a plate 270 which is positioned horizontally over the proximal end 262B positioned vertically. The plate 270 has a central opening which leads into the lumen 264. The plate 270 has another opening 272 which is used for insertion of the camera 16.

Figure 14B:
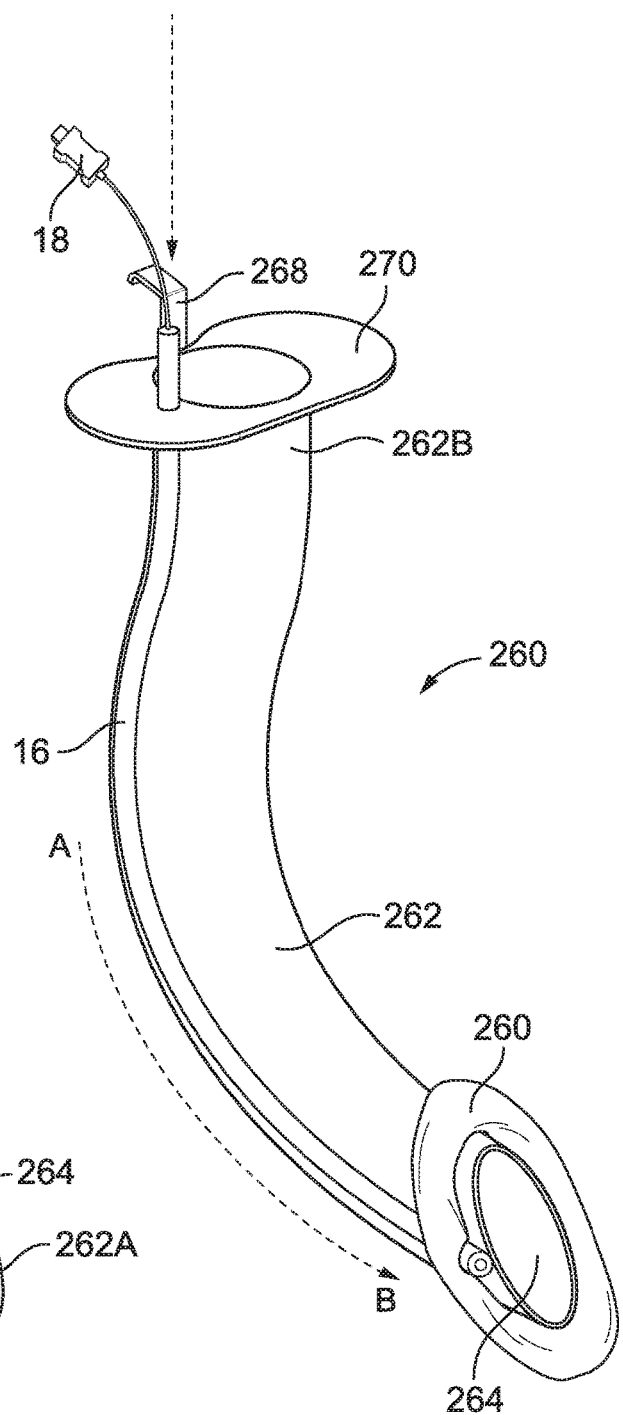
FIG. 14B depicts the device of FIG. 14A with the cuff being moved distally.

As shown in FIG. 14B, the handle 268 can be pushed distally such that the cuff 266 is moved along the proximal-distal axis A-B of the curved tubal body 262. The cuff 266 can be a tube made of a soft material or a balloon which can be inflated to occlude the upper esophagus. Importantly, the cuff 266 wraps over the camera 16. Thus, when the cuff 266 is moved distally along the curved tubal body 262, the camera 16 can still obtain images distally to the cuff 262.

Figure 15A:
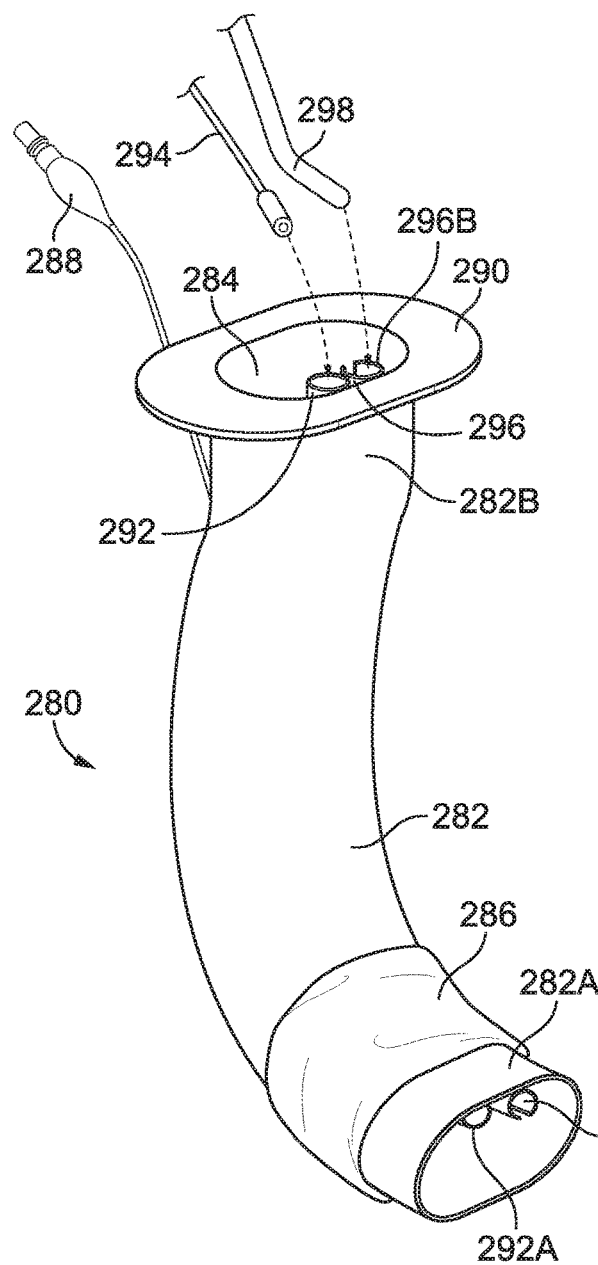
FIG. 15A depicts an oral airway device equipped with a camera and a slit wall tube, both positioned internally in the oral airway device.

FIG. 15A provides a further embodiment for an oral airway device equipped with a camera, generally 280. The oral airway device 280 comprises a hollow tubal body 282 with a central lumen 284. The tubal body 282 is a curved wall. The curvature of the tubal body 282 follows the curvature of a patient's tongue such that the device 280 can be placed over the patient's tongue and prevent the tongue from rolling over.

The tubal body 282 has a distal end 282A and a proximal end 282B. An inflatable cuff 286 wraps around the tubal body 282 near the distal end 282A. The cuff 286 can be inflated with the means 288 after the oral airway device 280 has been positioned in the patient. The tubal body 282 ends with a plate 290 at the proximal end 282B. The plate 290 is perpendicular to the tubal body 282 and remains outside the patient's body. The plate 290 prevents the device 280 from sliding into the patient. The tubal body 282 with the plate 290 comprises the central lumen 284. A hollow tube 292 is positioned inside the central lumen 284. The hollow tube 292 runs along the wall of the tubal body 282 from its distal end 282B to its proximal end 282A. The hollow tube 292 is glued or otherwise attached to the wall of the tubal body 282. A camera 294 can be inserted into the hollow tube 292.

Next to the hollow tube 292 is a slit wall tube 296 inside the central lumen 284. The slit wall tube 296 is glued or otherwise attached along the wall of the tubal body 282 such that a distal end 296A of the slit wall tube 296 is aligned with the distal end 282A of the tubal body 282. The distal end 296A of the slit wall tube 296 is in near proximity with a distal end of the tube 292. The slit wall tube 296 can host a bougie 298 which can be inserted into the slit wall tube 296 through a proximal end 296B. Because the camera 294 is in near proximity with the bougie 298 when the bougie 298 is inserted in the slit wall tube 296, the bougie 298 can be used for guiding the insertion of a medical device positioned in the central lumen 284 under the contentious visualization from the camera 294. The slit wall tube 296 can be also used for insertion of other tools in addition or instead of the bougie 298. The bougie 298 can be removed from the slit wall tube 296 and re-inserted as needed.

While the embodiment of FIG. 15A provides a slit wall tool tube for an oral airway device, it will be appreciated that a slit wall tool tube can be also used in other embodiments of this disclosure, including a tool tube in endotracheal devices in FIG. 8, FIGS. 9A and 9B, an oral airway device of FIGS. 11A, 11B, 11C, 11D and 11E and any other devices in which a tool tube is used for delivering a bougie and/or any other tool.

Figure 15B:
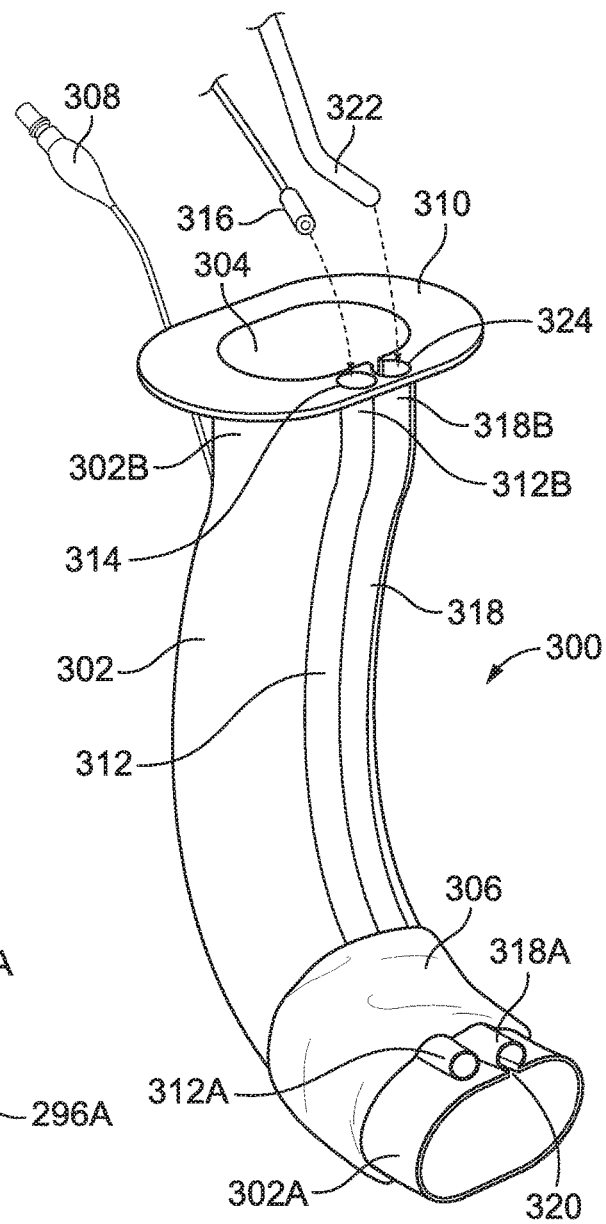
FIG. 15B depicts another embodiment for an oral airway device equipped with a camera and a slit wall tube.

Another embodiment of an oral airway device, generally 300 is depicted in FIG. 15B. In this embodiment, the oral airway device 300 comprises a hollow tubal body 302. The hollow tubal body 302 comprises a central lumen 304. The hollow tubal body 302 is a curved wall which follows the curvature of a patient's tongue. The hollow tubal body 302 comprises a distal end 302A and a proximal end 302B. A cuff 306 wraps around the tubal body 302 near the distal end 302A.

The cuff 306 can be inflated with the means 308 located proximally to the proximal end 302B of the tubal body 302. The tubal body 302 ends with a plate 310 at the proximal end 302B. The plate 310 is perpendicular to the tubal body 302 and remains outside the patient's body after the device 300 has been inserted into the patient. The plate 310 prevents the device 300 from sliding into the patient. The wall of the tubal body 302 together with the plate 310 create a central lumen 304.

A hollow tube 312 runs along the tubal body 302 externally, along the distal-proximal (302A-302B) axis of the tubal body 302. A distal end 312A of the tube 312 is aligned with the distal end 302A. The tube 312 runs under the cuff 306. Thus, the cuff 306 wraps around the tube 312 and tubal body 302. The cuff 306 keeps the tube 312 positioned on the tubal body 302 at the distal end 302A. A proximal end 312B of the tube 312 is inserted through an opening 314 in the plate 310. A camera 316 is inserted through the proximal end 312B of the tube 312. Because the distal end 312A is not sealed, the camera 316 can protrude from the tube 312 distally. The camera 316 can be removed from the tube 312 if no longer needed.

A slit wall tube 318 runs along the tubal body 302. A slit 320 of the slit wall tube 318 is aligned with the lumen 304 of the tubal body 302. Thus, the lumen 304 of the tubal body 302 and the slit wall tube 318 are connected by slit 320. A bougie 322 can be inserted into the slit wall tube 318. The cuff 306 wraps around the slit wall tube 318 and tubal body 302. The cuff 306 keeps the slit wall tube 318 positioned on the tubal body 302 at the distal end 302A. A proximal end 318B of the slit wall tube 318 is inserted through an opening 324 of the plate 310. While only the bougie 322 is shown in FIG. 15B, it will be appreciated that the slit wall tube 318 can be used for any other tools, such as for example, biopsy forceps or a suction tube. A distal end 318A of the slit wall tube 318 is in near proximity with the distal end 312A of the tube 312. Thus, the bougie 322 can be operated under the continuous visualization by the camera 316.

It will be appreciated that while the embodiment of FIGS. 15A and 15B provide a slit wall tube in connection with an oral airway device, the slit wall tube can be used in any of other devices described in this application. The slit wall tube can be used instead of or in addition to a tool tube in any of the devices in which the tool tube is used.

Figure 16A:
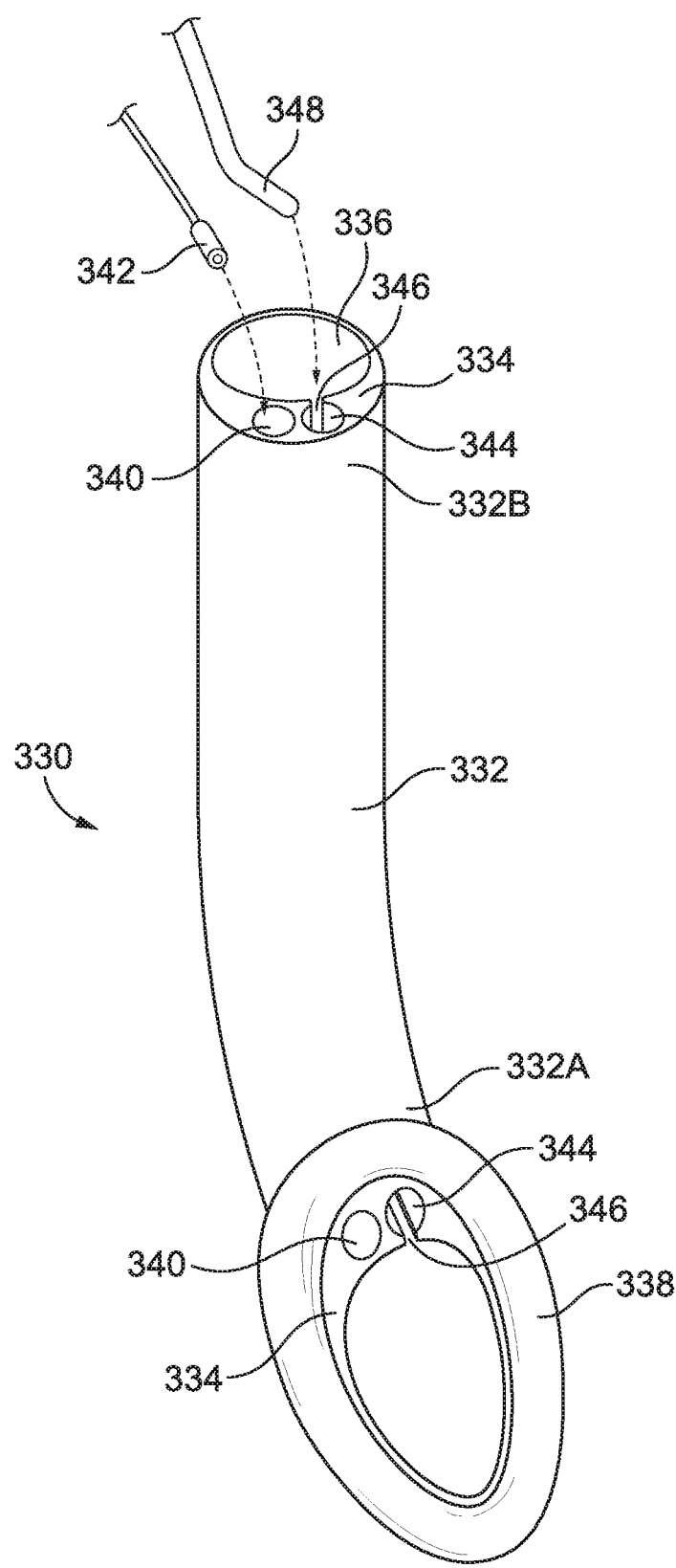
FIG. 16A depicts a supraglottic airway device with a camera and slit wall tube.

FIG. 16A depicts an embodiment of a supraglottic airway device, generally 330. The device 330 comprises a hollow tubal body 332, the wall 334 of the hollow tubal body 332 creates a central lumen 336. At a distal end 332A, the tubal body 332 ends with a soft cuff 338. The cuff 338 cannot be inflated. In other embodiments (not shown), the device 330 can comprise an inflatable cuff instead of the cuff 338. The wall 334 of the tubal body 332 comprises a lumen 340 which begins at the proximal end 332B of the tubal body 332 and runs all the way to the distal end 332A of the tubal body 332. A camera 342 can be inserted through the lumen 340 and provide images distally to the device 330. The lumen 340 is not sealed. Thus, the camera 342 can protrude distally from the lumen 340. The wall 334 also comprises a semi-lumen 344 which opens with a slit 346 into the central lumen 336. The semi-lumen 344 begins at the proximal end 332B of the tubal body 332. The semi-lumen 344 runs all the way to the distal end 332A of the tubal body 332. A bougie 348 can be inserted through the semi-lumen 334. The bougie 348 can protrude distally from the device 330 when inserted in the semi-lumen 334. The semi-lumen 334 is in near proximity with the lumen 340. Accordingly, the bougie 348 can be manipulated under the continuous visualization from the camera 342. This allows for guiding the placement of the device 330 with the bougie 348 under the continuous visualization from the camera 342. Because the bougie 348 can be also brought into the main lumen 336 through the slit 346, the bougie 348 can also assist in guiding a placement of any other device, such as for example an endotracheal tube, when the endotracheal tube is inserted in the central lumen 336.

Figure 16B:
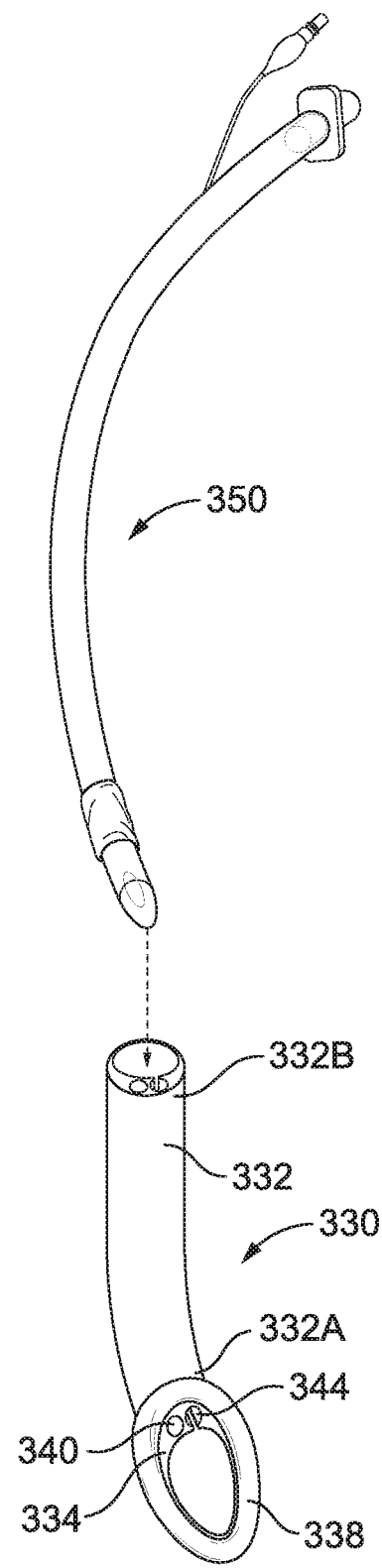
FIG. 16B depicts positioning of an endotracheal tube into the supraglottic airway device of FIG. 16A.

FIG. 16B depicts insertion of an endotracheal tube 350 into the device 330. Any endotracheal tube described in this application or generally known in the field can be used in the assembly with the device 330.

A further embodiment of a device, generally 360, is shown in FIG. 17A. The device 360 can be characterized as a truncated supraglottic device because the device 360 has a truncated tubal body 362 which ends with a soft cuff 364 at a distal end 362A of the truncated tubal body 362. The wall 366 of the truncated tubal body 362 comprises a lumen 368. The lumen 368 extends proximally from the tubal body 362 as a tube 370. The length of the tube 370 is such that a proximal end 370B may extend outside the patient's body, while the truncated tubal body 362 is fully inserted in the patient. A camera 372 is inserted into the tube 370 through the proximal end 370B of the tube 370. The camera 372 can protrude distally from the lumen 368 and take images distally to the device 360. The device 360 is equipped with a handle 374 which runs along the tube 370. The handle 374 comprises at least one semi-ring 376 for holding in place an endotracheal tube or any other tubal device when combined with the device 360. While in the embodiment of FIG. 17A, the holder is a semi-ring, other options may include a ring, including a ring with a clasp.

In addition to the lumen 368, the wall 366 also comprises a semi-lumen 378 which opens with a slit 380 into a main lumen 382 of the truncated tubal body 362. Just like the lumen 368 which extends proximally via the tube 370 from the truncated tubal body 362, the semi-lumen 378 also extends proximally via a slit wall tube 382. A proximal end 382B of the slit wall tube 382 remains outside the patient's body after the device 360 is inserted into the patient. A bougie 384 is inserted through the proximal end 382B of the slit wall tube 382. The bougie 384 can protrude distally from the semi-lumen 378. The semi-lumen 378 is in near proximity with the lumen 368 such that the bougie 384 can be monitored with the camera 372. Thus, the bougie 384 guides placement of the device 360 and any other tubal device, such as for example an endotracheal tube, under the continuous visualization by the camera 372.

FIG. 17B depicts an endotracheal tube 386 combined with the device 360. The endotracheal tube 386 is held in place on the device 360 with the semi-ring 376. The endotracheal tube 386 is inserted into the lumen 382 of the truncated tubal body 362. The distal end 386A of the endotracheal tube 386 can protrude distally from the device 360. A placement of the device 360 can be guided by manipulating the handle 374. The bougie 384 and camera 372 are not shown in FIG. 17B, but will be positioned as described in connection with FIG. 17A.

Figure 18A:
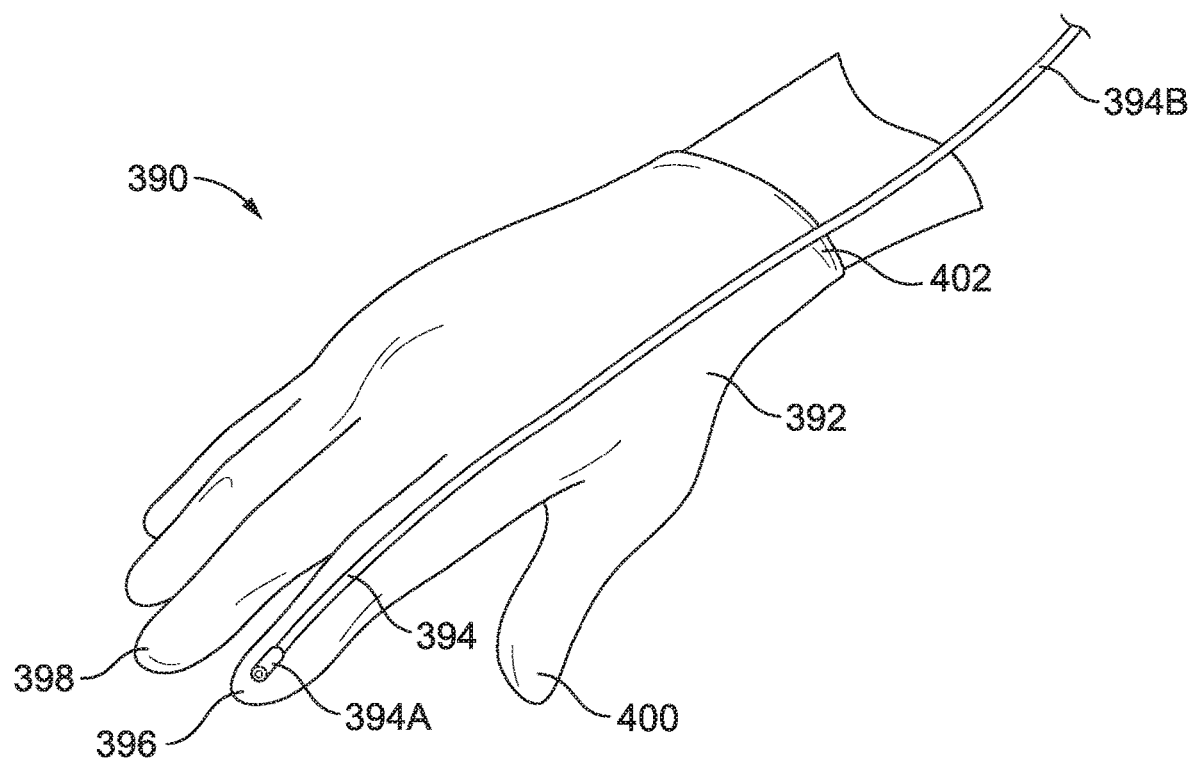
FIG. 18A depicts a medical examination glove equipped with a camera.

Referring to FIG. 18A, provided is a medical glove equipped with a camera, generally 390. The medical glove 390 has the dorsal side 392 which covers the dorsal side of a human hand. As also typical for medical gloves, the medical glove 390 comprises five fingers—one for each finger of the human hand. A practitioner can wear the glove 390 over his/her hand. In the embodiment of FIG. 18A, a right-hand glove is shown. It will be appreciated by a person of skill that in alternative embodiments, a left-hand glove can also be equipped with a camera.

In the embodiment of FIG. 18A, a camera 394 comprises a distal end 394A and a proximal end 394B. The distal end 394A of the camera 394 is aligned over the tip of the index finger 396. This allows continuous visualization distally to the medical glove 390 by the camera 394. The camera 394 is then sealed or otherwise attached to the dorsal side 392 of the glove 392. The proximal end 394B of the camera 394 extends over the gloved hand and can be connected to a computer or any other device by a wire. In some embodiments, the camera 394 can transmit images wirelessly.

It will be appreciated that in other embodiments, the camera 394 can be positioned over the middle finger 398 of the glove 390 or any other finger. The camera 394 can be attached to any part of the medical glove, any of the medical glove fingers, including the thumb 400, and a hand and/or wrist 402. The glove 390 can be further equipped with a tool tube (not shown) which can be used for insertion of tools such as for example, a bougie. The camera 394 can be also positioned over the palm of the hand instead of or in addition to the dorsal side of the glove.

Figure 18B:
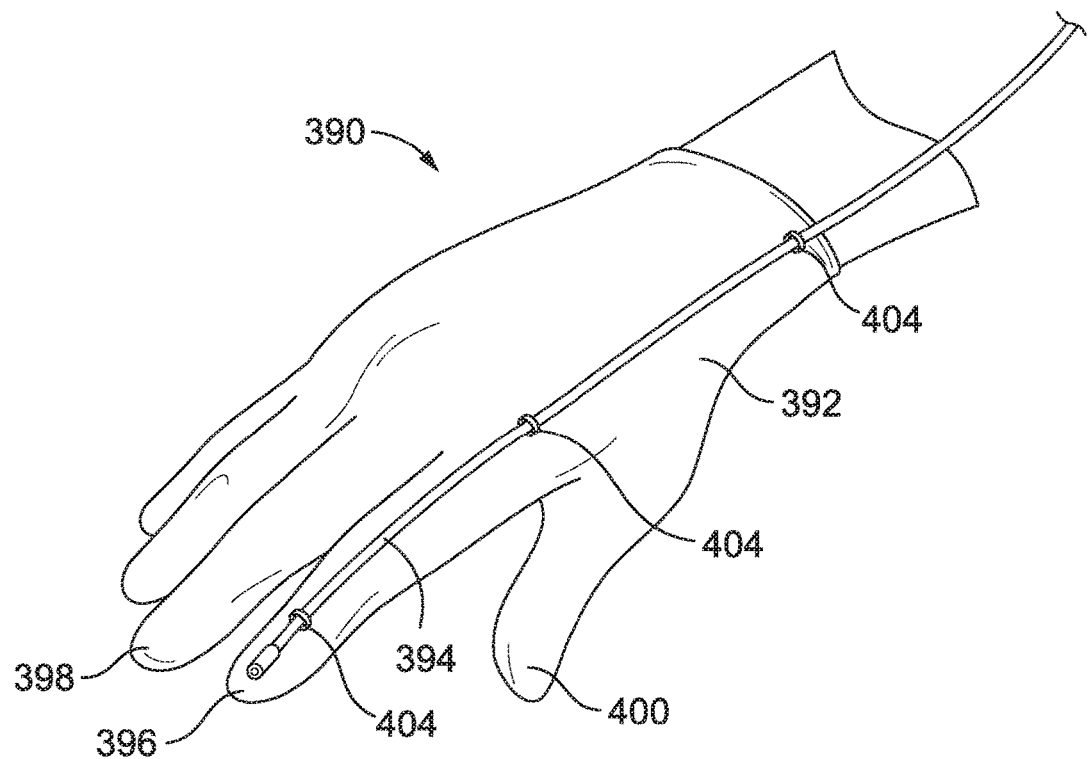
FIG. 18B is an alternative embodiment of a medical examination glove equipped with a camera.

A further embodiment of the glove 390 is shown in FIG. 18B where the glove 390 is equipped with a set of at least three rings, 404s. In other embodiments, the number of rings can vary from 1 to 20. At least some of the rings 404 are positioned over at least one finger. In the drawings of FIG. 18B, the ring 404 is positioned over the index finger. The camera 394 can be securely attached to the glove 390 with the rings 404. The camera 394 can be removed from the glove 390 when visualization is no longer needed. If additional rings 404 are positioned over middle finger 398 and/or any other fingers, the camera 394 can be easily moved between different fingers as may be needed.

Figure 19A:
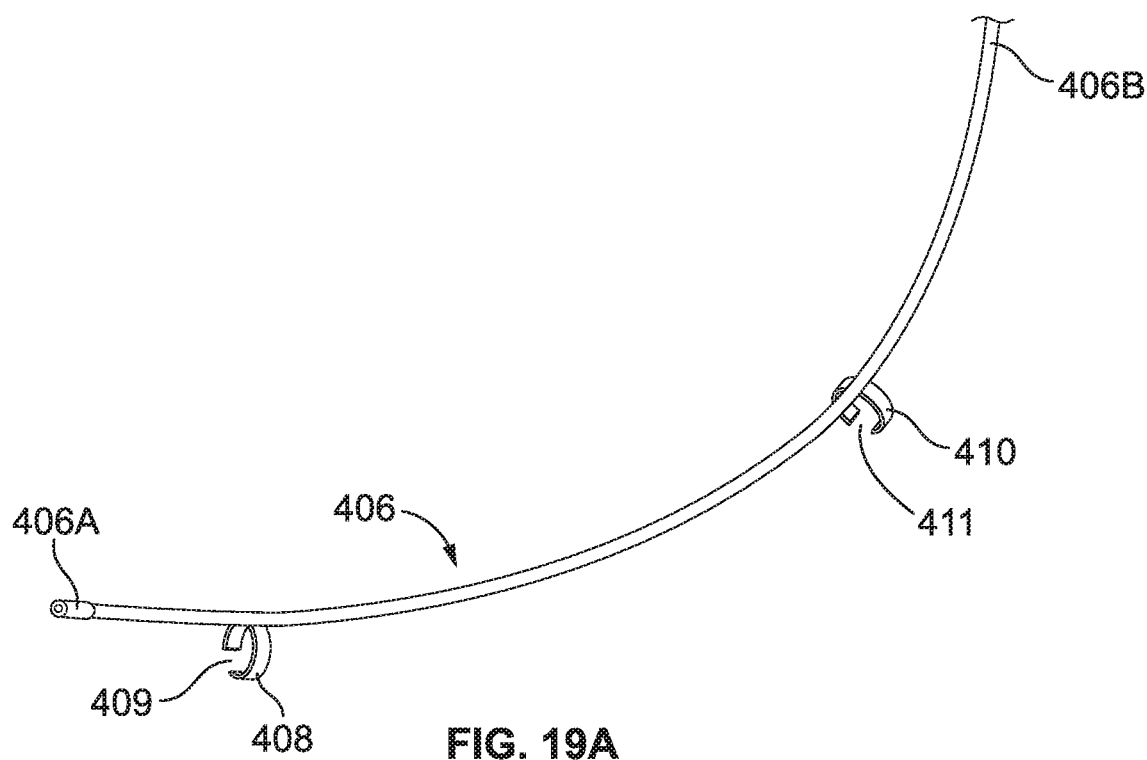
FIG. 19A depicts a camera equipped with two holders.
Figure 19B:
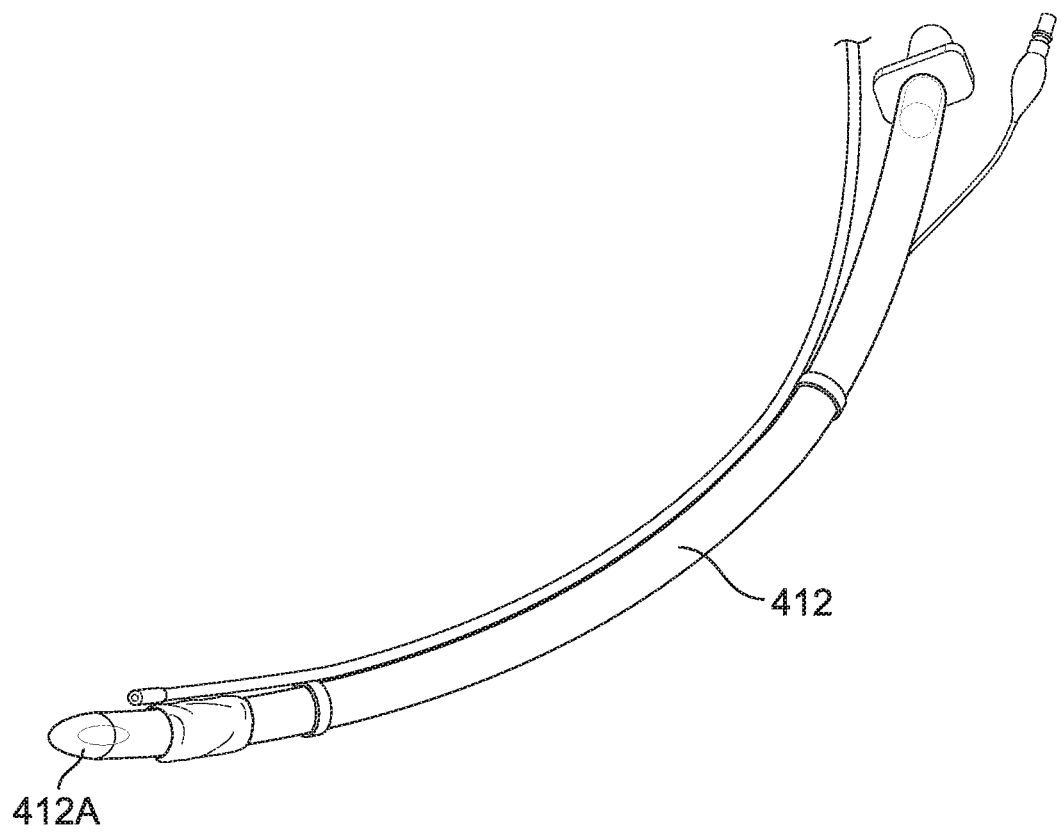
FIG. 19B depicts an assembly of the camera of FIG. 19A with an endotracheal tube.

Referring to FIG. 19A, it provides a camera 406 comprising two holders 408 and 410 for attaching the camera 406 to an endotracheal tube 412 as shown in FIG. 19B. The camera 406 has a distal end 406A and a proximal end 406B. The distal end collects images.

The holders 408 and 410 are attached to the camera 394 with an adhesive. In some embodiments two holders are used. In other embodiments from one to 10 holders can be used. The holder 408 is round in shape and has a slit 409. The diameter of the holder 408 is designed such that the endotracheal tube 412 can be pushed through the slit 409 into the holder 408. The holder 410 is also round and comprises a slit 411 through which the endotracheal tube 412 can fit. Thus, the camera 406 can be secured with the holders 408 and 410 on the body of the endotracheal tube 412 such that the distal end 406A of the camera 406 can be moved along the endotracheal tube 412 closer or further way from a distal end 412A of the endotracheal tube 412. While in the embodiments 19A and 19B, holders 408 and 410 are round with a slit, other embodiments may include those in which at least one of the holders is a ring and/or a ring with a clasp. The camera 406 can be combined not only with an endotracheal tube, but with any other device that comprise a tubal body, including an oral airway.

Figure 20:
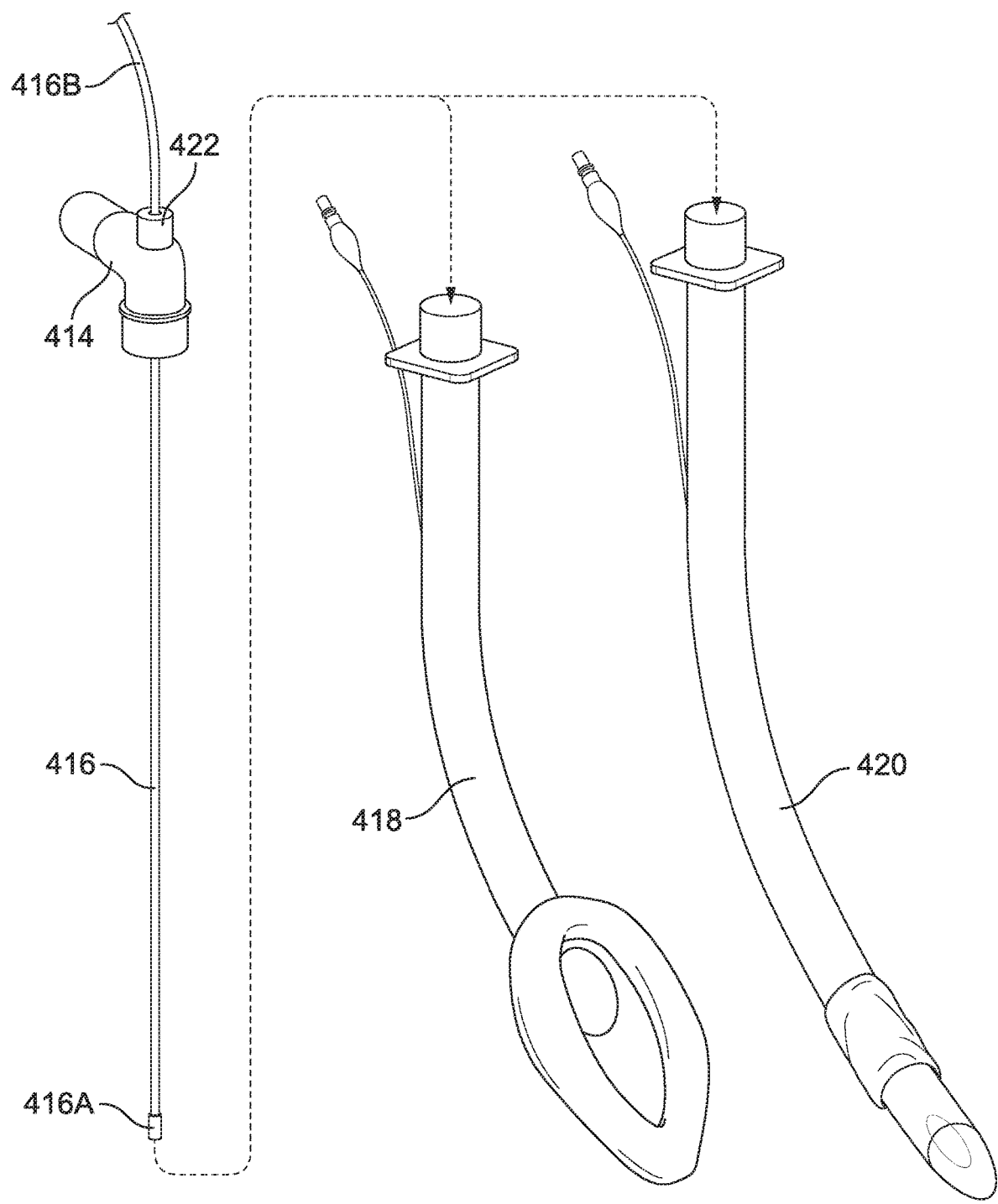
FIG. 20 depicts a ventilation cap equipped with a camera and the use of the ventilation cap in a supraglottic airway device or endotracheal tube.

Referring to FIG. 20, it provides a ventilation cap 414 with a camera 416. The ventilation cap 414 can be positioned over a supraglottic airway 418 or endotracheal tube 420 or any other device with a tubal body. The camera 416 can be inserted through an opening 422 in the cap 414 such that a distal end 416A of the camera 416 can protrude distally from the device 418 or 420 or any other tubal device into which the camera 416 is inserted. Combining the ventilation cap 414 with the device 418 or 420 allows to establish a close system and permits ventilation of a patient. This can be accomplished under the continuous visualization by the camera 416. A proximal end 416B of the camera 416 protrudes proximally to the ventilation cap 414. The proximal end 416B remains outside the patient body. The proximal end 416B can be connected to a computer and/or monitor. The camera 416 can be removed from the patient's body through the opening 422 while the ventilation cap 414 still remains in place in the patient. The ventilation cap 414 can be used with any supraglottic device, including those described in this application. The ventilation cap 414 can be used in combination with any endotracheal tube, including any of the endotracheal tubes described in this application.

Figure 21:
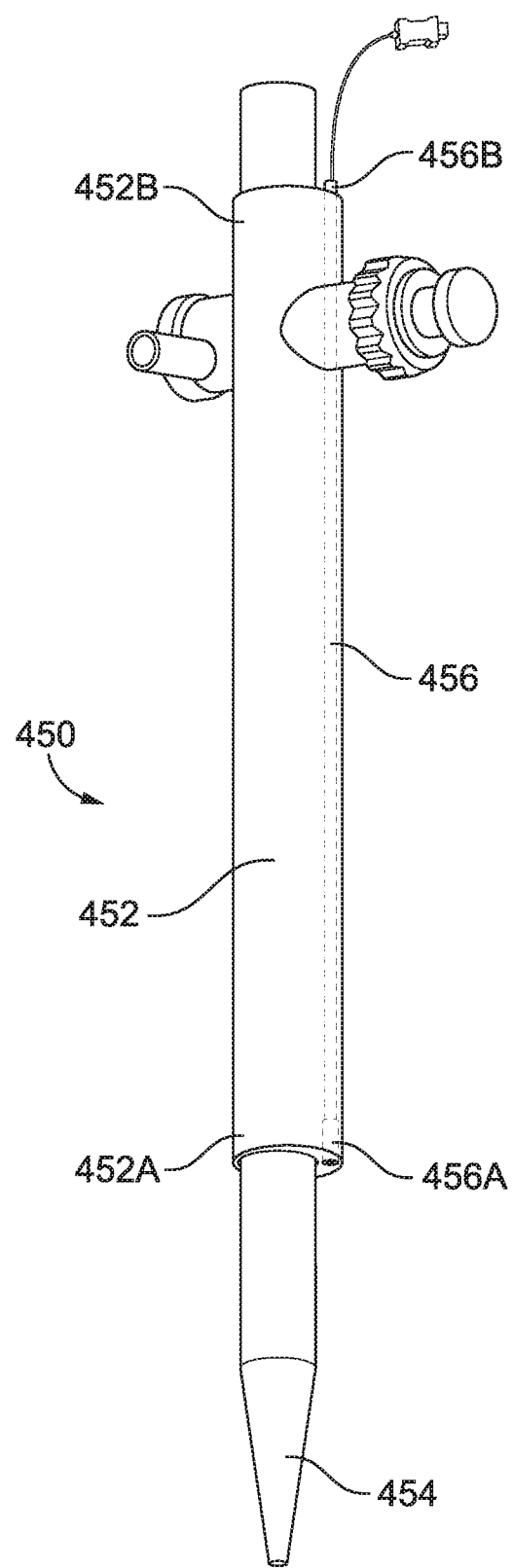
FIG. 21 depicts a laparoscopic trocar equipped with a camera.

Referring to FIG. 21, it depicts a trocar equipped with a camera, generally 450. The trocar 450 has a hollow tubal body 452 which can be either flexible or rigid with a distal end 452A and a proximal end 452B. A sharp piercing conical stylus 454 is protruding from the distal end 452A of the hollow tubal body 452 which comprises a lumen or a semi-lumen in its wall through which a camera 456 is inserted.

A distal end 456A of the camera 456 is positioned near the distal end 452A of the hollow tubal body 452. The proximal end 456B of the camera 456 remains outside the patient body. The camera 456 can provide visualization of the stylus 454.

The device 450 can be used during a laparoscopic surgery to create an opening into the patient's body with the stylus 454 under the continuous visualization by the camera 456. After the opening in the body has been created, the stylus 454 can be retracted from the hollow tubal body 452, and various instruments, i.e. a laparoscope, needed to complete a surgery can be inserted through the hollow tubal body 452. It will be appreciated that the camera 456 can be combined with any laparoscopic trocars, including robotic trocars.

While certain medical devices are described above, a person of skill would appreciate that this invention also includes embodiments with various obvious modifications as would be easily apparent to a person of skill.

What is claimed is:

1. A medical intubating device comprising a camera combined with a second device, wherein the second device is a tubeless intubating device which comprises an ellipsoid body connected to a handle, wherein the ellipsoid body comprises an upper oval surface, wherein the ellipsoid body encloses a lumen with a lumen opening which opens onto the upper oval surface; wherein the camera has a distal end and a proximal end and wherein the second device has a distal end and a proximal end, and wherein the distal end of the camera is in near proximity with the distal end of the second device; and wherein the medical intubating device does not comprise a separate sealed camera tube for placing the camera and wherein the camera is not separated from coming into contact with a patient's body when the medical intubating device is placed in the patient.

2. The medical intubating device of claim 1, wherein the upper oval surface of the ellipsoid body is connected to a bottom half-ellipsoid body surface.

3. The medical intubating device of claim 2, wherein the lumen further opens on a proximal side of the bottom half-ellipsoid surface with a canal through which an endotracheal tube can be inserted into the lumen.

4. The medical intubating device of claim 1, wherein the handle comprises a proximal part, a middle part and a distal part, and wherein a ring-holder is attached on the bottom surface of the proximal part of the handle, wherein the ring-holder is capable of holding a proximal end of an endotracheal tube or a supraglottic airway such that the tubeless intubating device is assembled with the endotracheal tube or the supraglottic airway.

5. The medical intubating device of claim 1, wherein the camera is attached slidably to the handle along the proximal-distal axis of the handle and the distal end of the camera is aligned inside the lumen.

6. The medical intubating device of claim 1, wherein the ellipsoid body comprises an inflatable cuff.

7. A method of intubating a patient, the method comprising inserting the medical device of claim 1 by guiding the insertion with a bougie under the continuous visualization with the camera.

* * * * *